US012590127B2

(12) United States Patent     (10) Patent No.:   US 12,590,127 B2

Gautier et al.     (45) Date of Patent:    Mar. 31, 2026

(54) SPLIT PHOTOACTIVE YELLOW PROTEIN COMPLEMENTATION SYSTEM AND USES THEREOF

(71) Applicants: PARIS SCIENCES ET LETTRES, Paris (FR); CENTRE NATIONAL DE LA RECHERCHE SCIENTIFIQUE, Paris (FR); SORBONNE UNIVERSITÉ, Paris (FR)

(72) Inventors: Arnaud Gautier, Paris (FR); Alison Tebo, Paris (FR)

(73) Assignees: PARIS SCIENCES ET LETTRES, Paris (FR); CENTRE NATIONAL DE LA RECHERCHE SCIENTIFIQUE, Paris (FR); SORBONNE UNIVERSITÉ, Paris (FR)

( * ) Notice: Subject to any disclaimer, the term of this patent is extended or adjusted under 35 U.S.C. 154(b) by 1062 days.

(21) Appl. No.: 17/600,329

(22) PCT Filed: Apr. 3, 2020

(86) PCT No.: PCT/EP2020/059635

§ 371 (c)(1),
(2) Date: Sep. 30, 2021

(87) PCT Pub. No.: WO2020/201538

PCT Pub. Date: Oct. 8, 2020

(65) Prior Publication Data

US 2022/0169682 A1     Jun. 2, 2022

(30) Foreign Application Priority Data

Apr. 5, 2019   (EP) .................................... 19305449

(51) Int. Cl.
    *C07K 14/195*     (2006.01)
    *C07D 277/36*     (2006.01)
          (Continued)

(52) U.S. Cl.
    CPC .......... *C07K 14/195* (2013.01); *C07D 277/36* (2013.01); *C07K 7/06* (2013.01);
          (Continued)

(58) Field of Classification Search
    CPC ........ C07K 14/195; C07K 7/06; C07K 19/00; C07K 2319/60; C07D 277/36; C07D 277/34; G01N 33/582; G01N 33/6845
          (Continued)

(56) References Cited

U.S. PATENT DOCUMENTS

2017/0137473 A1*   5/2017   Gautier ................ C07K 14/195

FOREIGN PATENT DOCUMENTS

WO     2016001437 A2     1/2016
WO     2018211090 A1     11/2018

OTHER PUBLICATIONS

Kerppola TK. Bimolecular fluorescence complementation (BiFC) analysis as a probe of protein interactions in living cells. Annu Rev Biophys. 2008;37:465-87. doi: 10.1146/annurev.biophys.37.032807. 125842. PMID: 18573091; PMCID: PMC2829326. (Year: 2008).*

(Continued)

*Primary Examiner* — Robert B Mondesi

(74) *Attorney, Agent, or Firm* — Maier & Maier, PLLC

(57) ABSTRACT

A complementation system including two fragments of photoactive yellow protein (PYP), or truncated fragments thereof, and its use with a fluorogenic hydroxybenzylidene rhodanine (HBR) analog for detecting interactions between biological molecules of interest, in particular between proteins of interest. Especially, a complementation system including a first PYP fragment having an amino acid sequence having at least about 70% identity with the amino acid sequence of SEQ ID NO: 23, or a truncated fragment thereof including at least 89 consecutive amino acids from the C-terminal end of the amino acid sequence; and a second (Continued)

PYP fragment having an amino acid sequence having at least about 70% identity with the amino acid sequence of SEQ ID NO: 34, or a truncated fragment thereof including at least 8 consecutive amino acids of the amino acid sequence, preferably 8 consecutive amino acids from the N-terminal end of the amino acid sequence.

19 Claims, 19 Drawing Sheets

Specification includes a Sequence Listing.

(51) Int. Cl.
| | |
|---|---|
| *C07K 7/06* | (2006.01) |
| *C07K 19/00* | (2006.01) |
| *G01N 33/58* | (2006.01) |
| *G01N 33/68* | (2006.01) |

(52) U.S. Cl.
CPC ........... *C07K 19/00* (2013.01); *G01N 33/582* (2013.01); *G01N 33/6845* (2013.01); *C07K 2319/60* (2013.01)

(58) Field of Classification Search
USPC ......................................................... 530/350
See application file for complete search history.

(56) References Cited

OTHER PUBLICATIONS

Sadowski MI, Jones DT. The sequence-structure relationship and protein function prediction. Curr Opin Struct Biol. Jun. 2009; 19(3): 357-62. doi: 10.1016/j.sbi.2009.03.008. Epub May 4, 2009. PMID: 19406632. (Year: 2009).*

Seffernick JL, de Souza ML, Sadowsky MJ, Wackett LP. Melamine deaminase and atrazine chlorohydrolase: 98 percent identical but functionally different. J Bacteriol. Apr. 2001;183(8):2405-10. doi: 10.1128/JB.183.8.2405-2410.2001. PMID: 11274097; PMCID: PMC95154. (Year: 2001).*

Tang S, Edwards EA. Identification of Dehalobacter reductive dehalogenases that catalyse dechlorination of chloroform, 1,1,1-trichloroethane and 1,1-dichloroethane. Philos Trans R Soc Lond B Biol Sci. Mar. 11, 2013;368(1616):20120318. doi: 10.1098/rstb. 2012.0318. PMID: 23479748; PMCID: PMC3638459. (Year: 2013).*

International Search Report on Patentability issued on Jul. 7, 2020, in corresponding International Application No. PCT/EP2020/ 059635, 6 pages.

Plamont et al., "Small Fluorescence-Activating and Absorption-Shifting Tag for Tunable Protein Imaging In Vivo", PNAS, The National Academy of Sciences of the USA, Jan. 19, 2016, vol. 113, No. 3, pp. 497-502.

Tebo et al., "Improved Chemical-Genetic Fluorescent Markers for Live Cell Microscopy", Biochemistry, American Chemical Society, ACS Publications, Oct. 2, 2018; No. 57, pp. 5648-5653.

Demidov et al., "Fast Complementation of Split Fluorescent Protein Triggered by DNA Hybridization", PNAS, The National Academy of Sciences of the USA, Feb. 14, 2006, vol. 103, No. 7, pp. 2052-2056.

Piston et al., "Fluorescent Protein FRET: The Good, The Bad and The Ugly", TRENDS in Biochemical Sciences, ScienceDirect, Elsevier Ltd., Sep. 2007, vol. 32, No. 9, pp. 407-414.

Magliery et al., "Detecting Protein-Protein Interactions with a Green Fuorescent Protein Fragment Reassembly Trap: Scope and Mechanism", J. Am. Chem. Soc., American Chemical Society, Jan. 12, 2005, vol. 127, No. 1, pp. 146-157.

Filonov et al., "A Near-Infrared BiFC Reporter for In Vivo Imaging of Protein-Protein Interactions", Chemistry & Biology Resource, Elsevier Ltd, Aug. 22, 2013, vol. 20, No. 8, pp. 1078-1086.

Mihara et al., "Functional Expression and Site-Directed Mutagenesis of Photoactive Yellow Protein" J. Biochem., May 1997, vol. 121, No. 5, pp. 876-880.

Chosrowjan et al., "Environmental Effects on the Femtosecond-Picosecond Fluorescence Dynamics of Photoactive Yellow Protein: Chromophores in Aqueous Solutions and in Protein Nanospaces Modified by Site-Directed Mutagenesis", J. Phys. Chem. B, American Chemical Society, Sep. 10, 1998, vol. 102, No. 40, pp. 7695-7698.

Kyndt et al., "Rhodobacter Capsulatus Photoactive Yellow Protein: Genetic Context, Spectral and Kinetics Characterization, and Mutagenesis", Biochemistry, American Chemical Society, Jan. 30, 2004, vol. 43, No. 7, pp. 1809-1820.

Borucki et al., "Effect of Salt and pH on the Activation of Photoactive Yellow Protein and Gateway Mutants Y98Q and Y98F", Biochemistry, American Chemical Society, Sep. 27, 2005, vol. 44, No. 42, pp. 13650-13663.

Hospes et al., "Tryptophan Fluorescence as a Reporter for Structural Changes in Photoactive Yellow Protein Elicited by Photo-Activation", Photochemical & Photobiological Sciences, The Royal Society of Chemistry and Owner Societies, RSC Publishing, Mar. 2013, vol. 12, No. 3, pp. 479-488.

Hospes et al., "Tryptophan Fluorescence as a Reporter for Structural Changes in Photoactive Yellow Protein Elicited by Photo-Activation", Photochemical & Photobiological Sciences, The Royal Society of Chemistry and Owner Societies, RSC Publishing, Mar. 2013, vol. 12, No. 3, pp. 479-488, Electronic Supplementary Information.

Hospes, "Light Responses of Bacteria: Site-Directed Mutagenesis Study of PYP & Photo-Inactivation of *E. coli* and *B. bubtilis*", Swammerdam Institute for Life Sciences (SILS), University of Amsterdam, ISBN: 978-90-5335-599-2, 2012, 161 pages.

Van Der Horst, "Structure/Function Relations in Photoactive Yellow Protein", Swammerdam Institute for Life Sciences, Section Micro-biology, University of Amsterdam, XP55214186A, Apr. 27, 2004, 140 pages.

Kyndt et al., "Structural Role of Tyrosine 98 in Photoactive Yellow Protein: Effects on Fluorescence, Gateway, and Photocycle Recovery", Biochemistry, American Chemical Society, Jan. 2, 2007, vol. 46, No. 1, pp. 95-105.

Khodair, "A Convenient Synthesis of 2-Arylidene-5H-thiazolo [2,3-b]quinazo-line-3,5[2H]-diones and their Benzoquinazoline Derivatives", Journal of Heterocyclic Chemistry, Chemistry Department, Tanta University, Nov.-Dec. 2002, vol. 39, 4 pages.

Tebo et al., "Circularly Permuted Fluorogenic Proteins for the Design of Modular Biosensors", ACS Chemical Biology, American Chemical Society, ACS Publications, Aug. 8, 2018, vol. 13, No. 9, pp. 2392-2397.

* cited by examiner

E3-CFAST(65-125) + NFAST(1-64)-K3 count fluorescence

E3-CFAST(115-125) + NFAST(1-114)-K3 count

+HMBR fluorescence

-HMBR
+HMBR

K3-NFAST(1-64) + CFAST(65-125)-E3 count fluorescence

K3-NFAST(1-114) + CFAST(115-125)-E3 count

+HMBR fluorescence

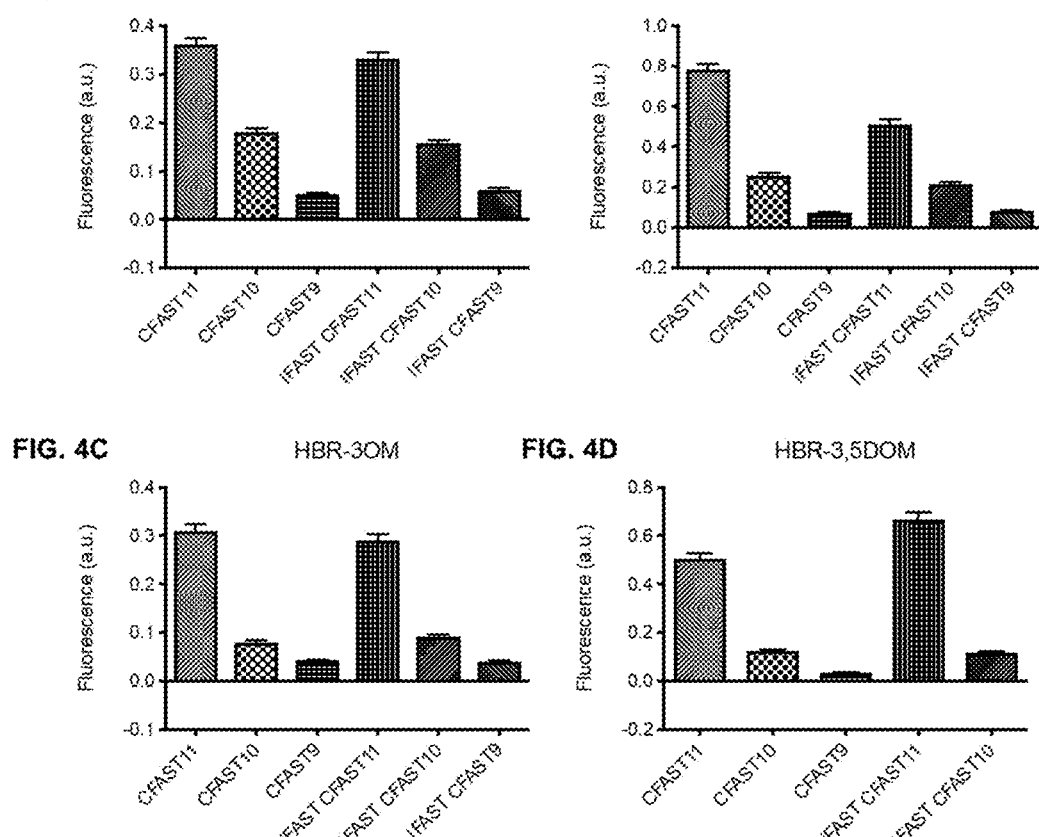

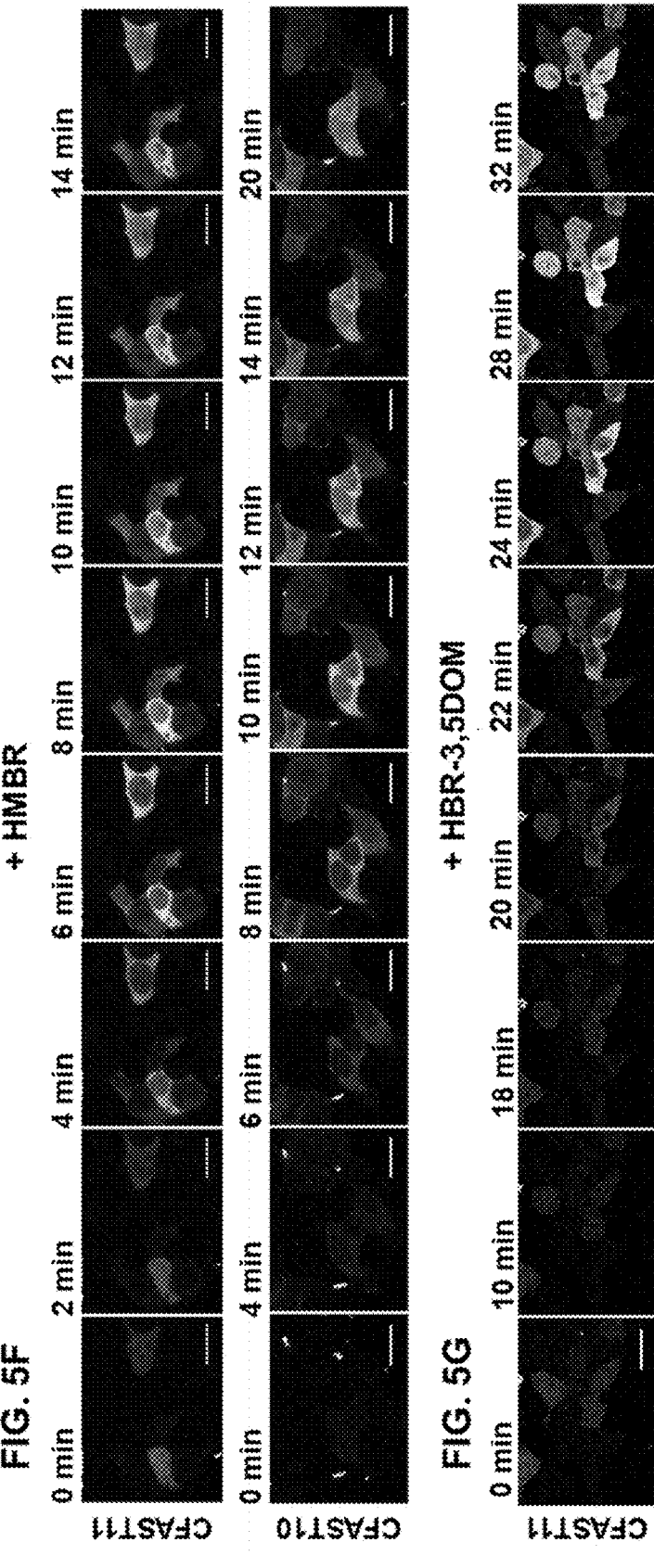

FIG. 6A

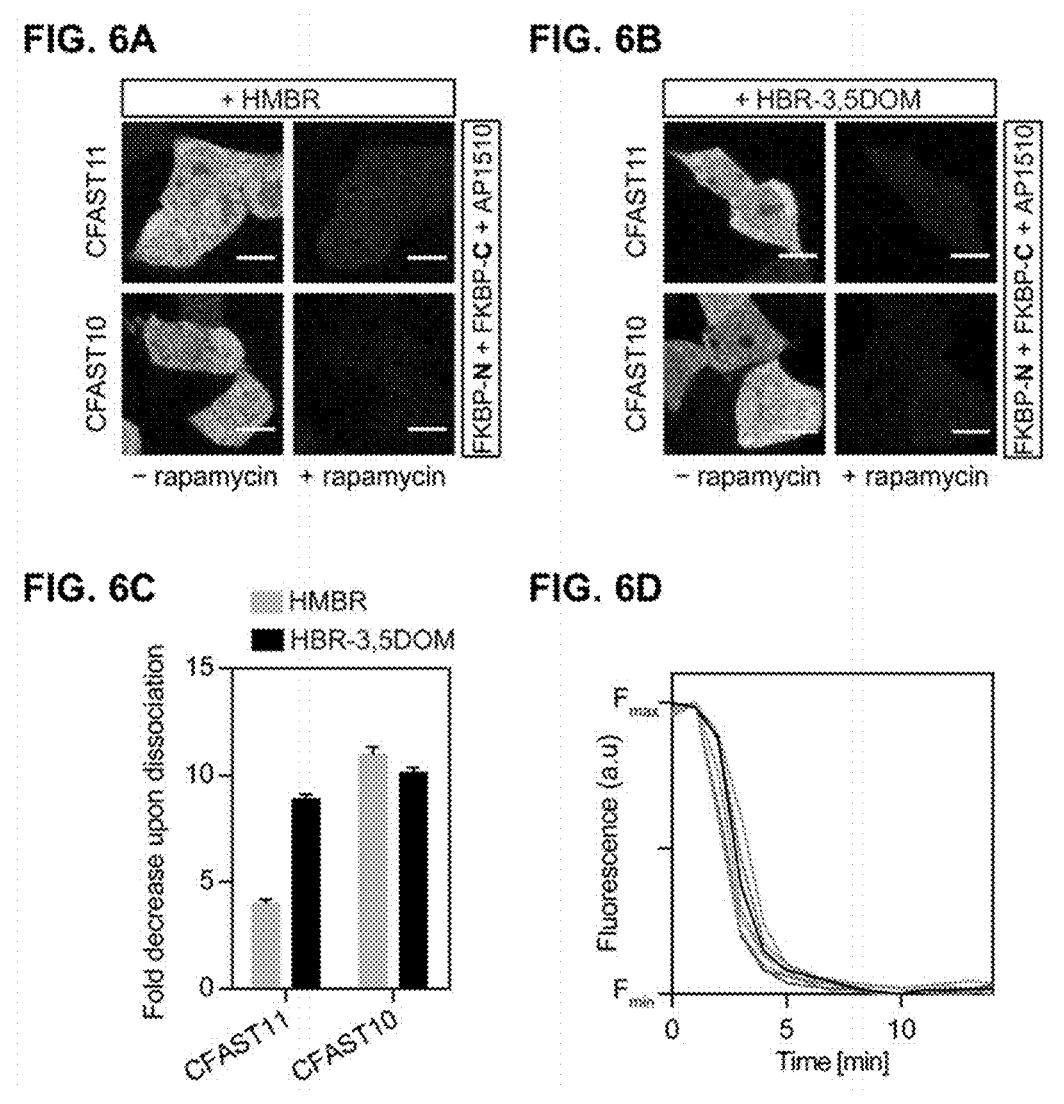

+ HMBR

CFAST11

CFAST10

FKBP-N + FKBP-C + AP1510

− rapamycin   + rapamycin

FIG. 6B

+ HBR-3,5DOM

CFAST11

CFAST10

FKBP-N + FKBP-C + AP1510

− rapamycin   + rapamycin

FIG. 6C

HMBR
HBR-3,5DOM

Fold decrease upon dissociation

15

10

5

0

CFAST11   CFAST10

FIG. 6D

$F_{max}$ $F_{min}$

Fluorescence (a.u)

0   5   10

Time [min]

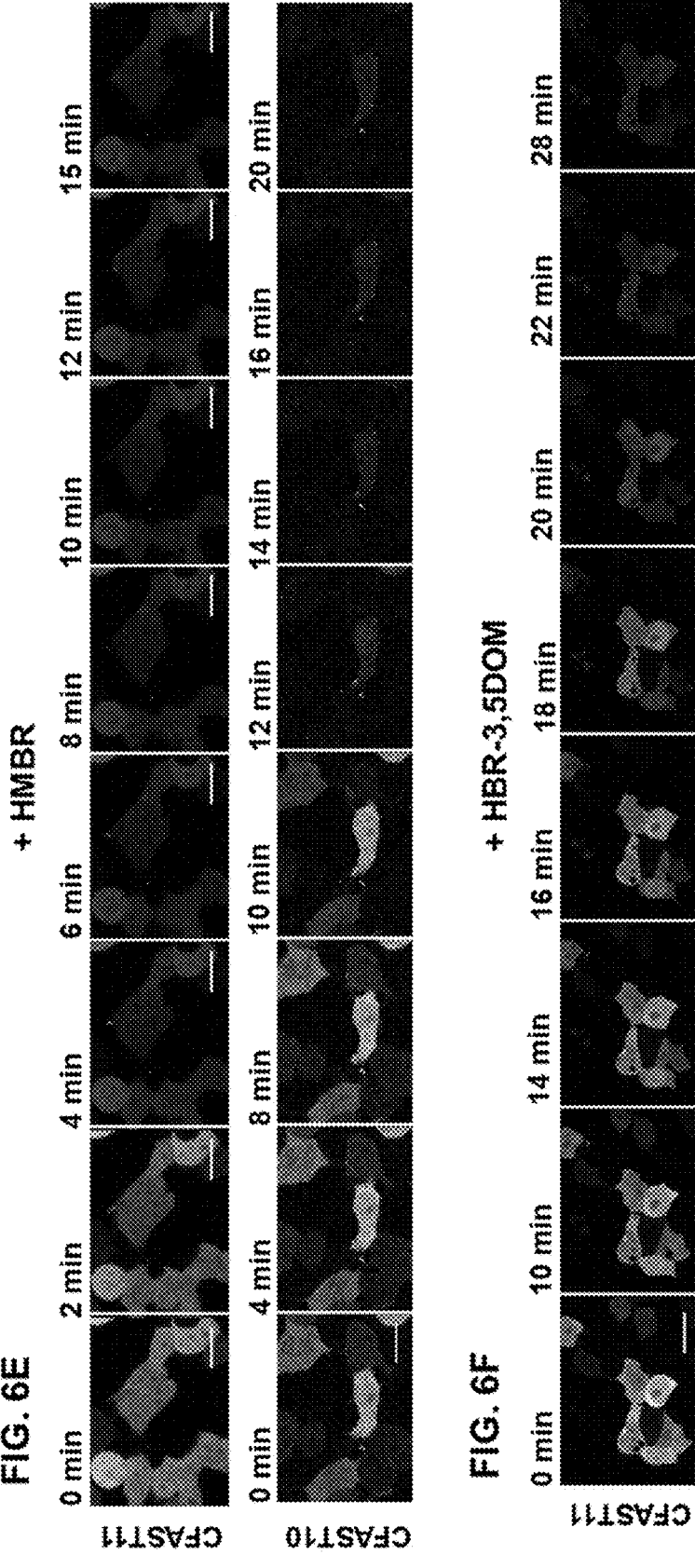

FIG. 8A

+HMBR

CFAST11

CFAST10

Lyn11-FRB-N + FKBP-C

− rapamycin　　+ rapamycin

FIG. 8B

$F_{max}$ $F_{min}$

Fluorescence (a.u)

0　　10　　20　　30　　40

Time [min]

FIG. 9A
NFAST-K-Ras + Raf1-CFAST-mCherry
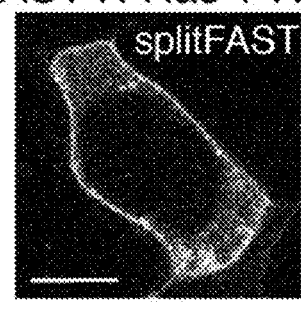 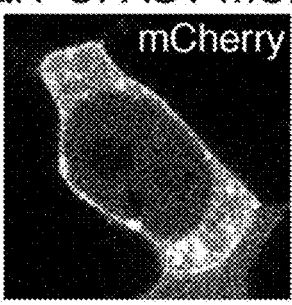
FIG. 9B
MEK1-NFAST + mCherry-ERK2-CFAST
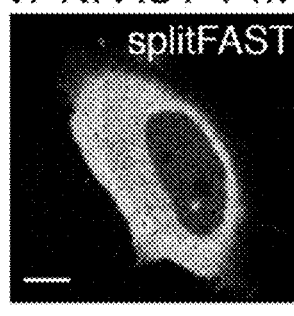 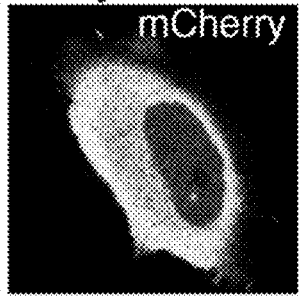
FIG. 9C
NFAST-MKP1 + mCherry-ERK2-CFAST
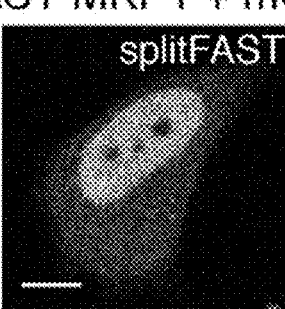 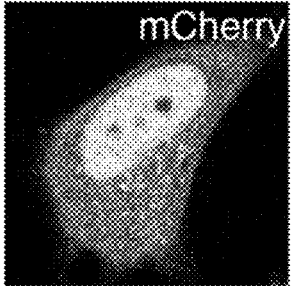

SEQUENCE LISTING

<160> NUMBER OF SEQ ID NOS: 109

<210> SEQ ID NO 1
<211> LENGTH: 125
<212> TYPE: PRT
<213> ORGANISM: Halorhodospira halophila

<400> SEQUENCE: 1

```
Met Glu His Val Ala Phe Gly Ser Glu Asp Ile Glu Asn Thr Leu Ala
1               5                   10                  15

Lys Met Asp Asp Gly Gln Leu Asp Gly Leu Ala Phe Gly Ala Ile Gln
            20                  25                  30

Leu Asp Gly Asp Gly Asn Ile Leu Gln Tyr Asn Ala Ala Glu Gly Asp
            35                  40                  45

Ile Thr Gly Arg Asp Pro Lys Gln Val Ile Gly Lys Asn Phe Phe Lys
    50                  55                  60

Asp Val Ala Pro Cys Thr Asp Ser Pro Glu Phe Tyr Gly Lys Phe Lys
65                  70                  75                  80

Glu Gly Val Ala Ser Gly Asn Leu Asn Thr Met Phe Glu Tyr Thr Phe
                85                  90                  95

Asp Tyr Gln Met Thr Pro Thr Lys Val Lys Val His Met Lys Lys Ala
                100                 105                 110

Leu Ser Gly Asp Ser Tyr Trp Val Phe Val Lys Arg Val
            115                 120                 125
```

<210> SEQ ID NO 2
<211> LENGTH: 125
<212> TYPE: PRT
<213> ORGANISM: Halomonas boliviensis LC1

<400> SEQUENCE: 2

```
Met Glu Thr Val Arg Phe Gly Gly Asp Asp Ile Glu Asn Ser Leu Ala
```

-continued

```
1               5                    10                    15

Lys Met Asp Asp Lys Lys Leu Asp Glu Leu Ala Phe Gly Ala Ile Gln
            20                  25              30

Leu Asp Ala Asn Gly Lys Ile Ile Gln Tyr Asn Ala Ala Glu Gly Gly
            35                  40                  45

Ile Thr Gly Arg Asp Pro Lys Ser Val Ile Gly Lys Asn Phe Phe Thr
            50                  55                  60

Glu Val Ala Pro Cys Thr Gln Ser Lys Glu Phe Gln Gly Arg Phe Lys
65                      70                  75                  80

Glu Gly Val Ser Ser Gly Glu Leu Asn Thr Met Phe Glu Tyr Val Phe
                    85                  90                  95

Asp Tyr Gln Met Thr Pro Thr Lys Val Lys Val His Met Lys Lys Ala
                100                 105                 110

Ile Ser Gly Asp Thr Tyr Trp Ile Phe Val Lys Arg Leu
            115                 120                 125
```

<210> SEQ ID NO 3
<211> LENGTH: 125
<212> TYPE: PRT
<213> ORGANISM: Halomonas sp. GFAJ-1

<400> SEQUENCE: 3

```
Met Glu Thr Val Arg Phe Gly Gly Asp Asp Ile Glu Asn Ala Leu Ala
1               5                    10                    15

Asn Met Asp Asp Lys Lys Leu Asp Thr Leu Ala Phe Gly Ala Ile Gln
            20                  25              30

Leu Asp Ala Asn Gly Lys Ile Ile Gln Tyr Asn Ala Ala Glu Gly Gly
            35                  40                  45

Ile Thr Gly Arg Asp Pro Lys Ser Val Ile Gly Lys Asn Phe Phe Thr
            50                  55                  60

Asp Val Ala Pro Cys Thr Gln Ser Lys Glu Phe Gln Gly Arg Phe Lys
65                      70                  75                  80

Glu Gly Val Lys Asn Gly Asp Leu Asn Thr Met Phe Glu Tyr Val Phe
                    85                  90                  95

Asp Tyr Gln Met Thr Pro Thr Lys Val Lys Val His Met Lys Lys Ala
                100                 105                 110

Leu Ser Gly Asp Thr Phe Trp Ile Phe Val Lys Arg Leu
            115                 120                 125
```

<210> SEQ ID NO 4
<211> LENGTH: 125
<212> TYPE: PRT
<213> ORGANISM: Rheinheimera sp. A13L

<400> SEQUENCE: 4

```
Met Glu Thr Val Arg Phe Gly Gly Asp Asp Ile Glu Asn Ser Leu Ala
1               5                    10                    15

Lys Met Asp Asp Lys Ala Leu Asp Lys Leu Ala Phe Gly Ala Ile Gln
            20                  25              30

Leu Asp Gly Asn Gly Lys Ile Ile His Tyr Asn Ala Ala Glu Gly Thr
            35                  40                  45

Ile Thr Gly Arg Asp Pro Lys Thr Val Ile Gly Lys Asn Phe Phe Thr
            50                  55                  60

Asp Val Ala Pro Cys Thr Gln Ser Lys Glu Phe Gln Gly Arg Phe Lys
65                      70                  75                  80

Glu Gly Val Gln Lys Gly Asp Leu Asn Thr Met Phe Glu Tyr Val Phe
```

```
                           85                    90                    95

Asp Tyr Gln Met Lys Pro Thr Lys Val Lys Val His Met Lys Lys Ala
                100                    105                    110

Met Thr Gly Asp Ser Phe Trp Ile Phe Val Lys Arg Leu
                115                    120                    125

<210> SEQ ID NO 5
<211> LENGTH: 125
<212> TYPE: PRT
<213> ORGANISM: Idiomarina loihiensis

<400> SEQUENCE: 5

Met Glu Ile Val Gln Phe Gly Ser Asp Asp Ile Glu Asn Thr Leu Ser
1                    5                    10                    15

Lys Met Ser Asp Asp Lys Leu Asn Asp Ile Ala Phe Gly Ala Ile Gln
                20                    25                    30

Leu Asp Ala Ser Gly Lys Ile Ile Gln Tyr Asn Ala Ala Glu Gly Asp
            35                    40                    45

Ile Thr Gly Arg Asp Pro Gly Ala Val Val Gly Lys Asn Phe Phe Asn
        50                    55                    60

Glu Val Ala Pro Cys Thr Asn Ser Pro Glu Phe Lys Gly Arg Phe Asp
65                    70                    75                    80

Glu Gly Val Lys Asn Gly Asn Leu Asn Thr Met Phe Glu Tyr Val Phe
                85                    90                    95

Asp Tyr Glu Met Gln Pro Thr Lys Val Lys Val His Met Lys Lys Ala
                100                    105                    110

Leu Thr Gly Asp Thr Tyr Trp Val Phe Val Lys Arg Leu
            115                    120                    125

<210> SEQ ID NO 6
<211> LENGTH: 125
<212> TYPE: PRT
<213> ORGANISM: Thiorhodospira sibirica ATCC 700588

<400> SEQUENCE: 6

Met Glu Leu Leu Ser Phe Gly Ala Asp Asn Ile Glu Asn Ser Leu Ala
1                    5                    10                    15

Lys Met Ser Lys Gly Asp Leu Asn Lys Leu Ala Phe Gly Ala Ile Gln
                20                    25                    30

Leu Asn Ala Gln Gly Lys Ile Leu Gln Tyr Asn Ala Ala Glu Gly Asp
            35                    40                    45

Ile Thr Gly Arg Lys Pro Thr Glu Val Ile Gly Lys Asn Phe Phe Leu
        50                    55                    60

Glu Val Ala Pro Cys Thr Asn Arg Thr Glu Phe Lys Gly Arg Phe Asp
65                    70                    75                    80

Gln Gly Ile Lys Ser Gly Asn Leu Asn Thr Met Phe Glu Tyr Thr Phe
                85                    90                    95

Asp Tyr Glu Met Lys Pro Thr Lys Val Lys Val His Met Lys Lys Ala
                100                    105                    110

Leu Val Asp Asp Thr Tyr Trp Val Phe Val Lys Arg Val
            115                    120                    125

<210> SEQ ID NO 7
<211> LENGTH: 125
<212> TYPE: PRT
<213> ORGANISM: Rhodothalassium salexigens

<400> SEQUENCE: 7
```

```
Met Glu Met Ile Lys Phe Gly Gln Asp Asp Ile Glu Asn Ala Met Ala
1               5                   10                  15

Asp Met Gly Asp Ala Gln Ile Asp Asp Leu Ala Phe Gly Ala Ile Gln
            20                  25                  30

Leu Asp Glu Thr Gly Thr Ile Leu Ala Tyr Asn Ala Ala Glu Gly Glu
        35                  40                  45

Leu Thr Gly Arg Ser Pro Gln Asp Val Ile Gly Lys Asn Phe Phe Lys
    50                  55                  60

Asp Ile Ala Pro Cys Thr Asp Thr Glu Glu Phe Gly Gly Arg Phe Arg
65                  70                  75                  80

Glu Gly Val Ala Asn Gly Asp Leu Asn Ala Met Phe Glu Tyr Val Phe
                85                  90                  95

Asp Tyr Gln Met Gln Pro Thr Lys Val Lys Val His Met Lys Arg Ala
            100                 105                 110

Ile Thr Gly Asp Ser Tyr Trp Ile Phe Val Lys Arg Val
        115                 120                 125

<210> SEQ ID NO 8
<211> LENGTH: 125
<212> TYPE: PRT
<213> ORGANISM: Halorhodospira halophila
<220> FEATURE:
<223> OTHER INFORMATION: C69G

<400> SEQUENCE: 8

Met Glu His Val Ala Phe Gly Ser Glu Asp Ile Glu Asn Thr Leu Ala
1               5                   10                  15

Lys Met Asp Asp Gly Gln Leu Asp Gly Leu Ala Phe Gly Ala Ile Gln
            20                  25                  30

Leu Asp Gly Asp Gly Asn Ile Leu Gln Tyr Asn Ala Ala Glu Gly Asp
        35                  40                  45

Ile Thr Gly Arg Asp Pro Lys Gln Val Ile Gly Lys Asn Phe Phe Lys
    50                  55                  60

Asp Val Ala Pro Gly Thr Asp Ser Pro Glu Phe Tyr Gly Lys Phe Lys
65                  70                  75                  80

Glu Gly Val Ala Ser Gly Asn Leu Asn Thr Met Phe Glu Tyr Thr Phe
                85                  90                  95

Asp Tyr Gln Met Thr Pro Thr Lys Val Lys Val His Met Lys Lys Ala
            100                 105                 110

Leu Ser Gly Asp Ser Tyr Trp Val Phe Val Lys Arg Val
        115                 120                 125

<210> SEQ ID NO 9
<211> LENGTH: 125
<212> TYPE: PRT
<213> ORGANISM: Artificial Sequence
<220> FEATURE:
<223> OTHER INFORMATION: functional PYP

<400> SEQUENCE: 9

Met Glu His Val Ala Phe Gly Ser Glu Asp Ile Glu Asn Thr Leu Ala
1               5                   10                  15

Lys Met Asp Asp Gly Gln Leu Asp Gly Leu Ala Phe Gly Ala Ile Gln
            20                  25                  30

Leu Asp Gly Asp Gly Asn Ile Leu Gln Tyr Asn Ala Ala Glu Gly Asp
        35                  40                  45

Ile Thr Gly Arg Asp Pro Lys Gln Val Ile Gly Lys Asn Phe Phe Lys
```

```
            50                  55                  60

Asp Val Ala Pro Gly Thr Asp Ser Pro Glu Phe Tyr Gly Lys Phe Lys
65                  70                  75                  80

Glu Gly Val Ala Ser Gly Asn Leu Asn Thr Met Phe Glu Trp Met Ile
                85                  90                  95

Pro Thr Ser Arg Gly Pro Thr Lys Val Lys Val His Met Lys Lys Ala
                100                 105                 110

Leu Ser Gly Asp Ser Tyr Trp Val Phe Val Lys Arg Val
        115                 120                 125

<210> SEQ ID NO 10
<211> LENGTH: 125
<212> TYPE: PRT
<213> ORGANISM: Artificial Sequence
<220> FEATURE:
<223> OTHER INFORMATION: functional PYP

<400> SEQUENCE: 10

Met Glu Thr Val Arg Phe Gly Gly Asp Asp Ile Glu Asn Ser Leu Ala
1                   5                   10                  15

Lys Met Asp Asp Lys Lys Leu Asp Glu Leu Ala Phe Gly Ala Ile Gln
                20                  25                  30

Leu Asp Ala Asn Gly Lys Ile Ile Gln Tyr Asn Ala Ala Glu Gly Gly
        35                  40                  45

Ile Thr Gly Arg Asp Pro Lys Ser Val Ile Gly Lys Asn Phe Phe Thr
    50                  55                  60

Glu Val Ala Pro Gly Thr Gln Ser Lys Glu Phe Gln Gly Arg Phe Lys
65                  70                  75                  80

Glu Gly Val Ser Ser Gly Glu Leu Asn Thr Met Phe Glu Trp Met Ile
                85                  90                  95

Pro Thr Ser Arg Gly Pro Thr Lys Val Lys Val His Met Lys Lys Ala
                100                 105                 110

Ile Ser Gly Asp Thr Tyr Trp Ile Phe Val Lys Arg Leu
        115                 120                 125

<210> SEQ ID NO 11
<211> LENGTH: 125
<212> TYPE: PRT
<213> ORGANISM: Artificial Sequence
<220> FEATURE:
<223> OTHER INFORMATION: functional PYP

<400> SEQUENCE: 11

Met Glu Thr Val Arg Phe Gly Gly Asp Asp Ile Glu Asn Ala Leu Ala
1                   5                   10                  15

Asn Met Asp Asp Lys Lys Leu Asp Thr Leu Ala Phe Gly Ala Ile Gln
                20                  25                  30

Leu Asp Ala Asn Gly Lys Ile Ile Gln Tyr Asn Ala Ala Glu Gly Gly
        35                  40                  45

Ile Thr Gly Arg Asp Pro Lys Ser Val Ile Gly Lys Asn Phe Phe Thr
    50                  55                  60

Asp Val Ala Pro Gly Thr Gln Ser Lys Glu Phe Gln Gly Arg Phe Lys
65                  70                  75                  80

Glu Gly Val Lys Asn Gly Asp Leu Asn Thr Met Phe Glu Trp Met Ile
                85                  90                  95

Pro Thr Ser Arg Gly Pro Thr Lys Val Lys Val His Met Lys Lys Ala
                100                 105                 110
```

-continued

```
Leu Ser Gly Asp Thr Phe Trp Ile Phe Val Lys Arg Leu
        115                 120                 125

<210> SEQ ID NO 12
<211> LENGTH: 125
<212> TYPE: PRT
<213> ORGANISM: Artificial Sequence
<220> FEATURE:
<223> OTHER INFORMATION: functional PYP

<400> SEQUENCE: 12

Met Glu Thr Val Arg Phe Gly Gly Asp Asp Ile Glu Asn Ser Leu Ala
1                 5                   10                  15

Lys Met Asp Asp Lys Ala Leu Asp Lys Leu Ala Phe Gly Ala Ile Gln
                20                  25                  30

Leu Asp Gly Asn Gly Lys Ile Ile His Tyr Asn Ala Ala Glu Gly Thr
            35                  40                  45

Ile Thr Gly Arg Asp Pro Lys Thr Val Ile Gly Lys Asn Phe Phe Thr
        50                  55                  60

Asp Val Ala Pro Gly Thr Gln Ser Lys Glu Phe Gln Gly Arg Phe Lys
65                  70                  75                  80

Glu Gly Val Gln Lys Gly Asp Leu Asn Thr Met Phe Glu Trp Met Ile
                85                  90                  95

Pro Thr Ser Arg Gly Pro Thr Lys Val Lys Val His Met Lys Lys Ala
            100                 105                 110

Met Thr Gly Asp Ser Phe Trp Ile Phe Val Lys Arg Leu
        115                 120                 125

<210> SEQ ID NO 13
<211> LENGTH: 125
<212> TYPE: PRT
<213> ORGANISM: Artificial Sequence
<220> FEATURE:
<223> OTHER INFORMATION: functional PYP

<400> SEQUENCE: 13

Met Glu Ile Val Gln Phe Gly Ser Asp Asp Ile Glu Asn Thr Leu Ser
1                 5                   10                  15

Lys Met Ser Asp Asp Lys Leu Asn Asp Ile Ala Phe Gly Ala Ile Gln
                20                  25                  30

Leu Asp Ala Ser Gly Lys Ile Ile Gln Tyr Asn Ala Ala Glu Gly Asp
            35                  40                  45

Ile Thr Gly Arg Asp Pro Gly Ala Val Val Gly Lys Asn Phe Phe Asn
        50                  55                  60

Glu Val Ala Pro Gly Thr Asn Ser Pro Glu Phe Lys Gly Arg Phe Asp
65                  70                  75                  80

Glu Gly Val Lys Asn Gly Asn Leu Asn Thr Met Phe Glu Trp Met Ile
                85                  90                  95

Pro Thr Ser Arg Gly Pro Thr Lys Val Lys Val His Met Lys Lys Ala
            100                 105                 110

Leu Thr Gly Asp Thr Tyr Trp Val Phe Val Lys Arg Leu
        115                 120                 125

<210> SEQ ID NO 14
<211> LENGTH: 125
<212> TYPE: PRT
<213> ORGANISM: Artificial Sequence
<220> FEATURE:
<223> OTHER INFORMATION: functional PYP
```

<400> SEQUENCE: 14

```
Met Glu Leu Leu Ser Phe Gly Ala Asp Asn Ile Glu Asn Ser Leu Ala
1               5                   10                  15

Lys Met Ser Lys Gly Asp Leu Asn Lys Leu Ala Phe Gly Ala Ile Gln
            20                  25                  30

Leu Asn Ala Gln Gly Lys Ile Leu Gln Tyr Asn Ala Ala Glu Gly Asp
        35                  40                  45

Ile Thr Gly Arg Lys Pro Thr Glu Val Ile Gly Lys Asn Phe Phe Leu
    50                  55                  60

Glu Val Ala Pro Gly Thr Asn Arg Thr Glu Phe Lys Gly Arg Phe Asp
65                  70                  75                  80

Gln Gly Ile Lys Ser Gly Asn Leu Asn Thr Met Phe Glu Trp Met Ile
            85                  90                  95

Pro Thr Ser Arg Gly Pro Thr Lys Val Lys Val His Met Lys Lys Ala
            100                 105                 110

Leu Val Asp Asp Thr Tyr Trp Val Phe Val Lys Arg Val
        115                 120                 125
```

<210> SEQ ID NO 15
<211> LENGTH: 125
<212> TYPE: PRT
<213> ORGANISM: Artificial Sequence
<220> FEATURE:
<223> OTHER INFORMATION: functional PYP

<400> SEQUENCE: 15

```
Met Glu Met Ile Lys Phe Gly Gln Asp Asp Ile Glu Asn Ala Met Ala
1               5                   10                  15

Asp Met Gly Asp Ala Gln Ile Asp Asp Leu Ala Phe Gly Ala Ile Gln
            20                  25                  30

Leu Asp Glu Thr Gly Thr Ile Leu Ala Tyr Asn Ala Ala Glu Gly Glu
        35                  40                  45

Leu Thr Gly Arg Ser Pro Gln Asp Val Ile Gly Lys Asn Phe Phe Lys
    50                  55                  60

Asp Ile Ala Pro Gly Thr Asp Thr Glu Glu Phe Gly Gly Arg Phe Arg
65                  70                  75                  80

Glu Gly Val Ala Asn Gly Asp Leu Asn Ala Met Phe Glu Trp Met Ile
            85                  90                  95

Pro Thr Ser Arg Gly Pro Thr Lys Val Lys Val His Met Lys Arg Ala
            100                 105                 110

Ile Thr Gly Asp Ser Tyr Trp Ile Phe Val Lys Arg Val
        115                 120                 125
```

<210> SEQ ID NO 16
<211> LENGTH: 125
<212> TYPE: PRT
<213> ORGANISM: Artificial Sequence
<220> FEATURE:
<223> OTHER INFORMATION: functional PYP

<400> SEQUENCE: 16

```
Met Glu His Val Ala Phe Gly Ser Glu Asp Ile Glu Asn Thr Leu Ala
1               5                   10                  15

Lys Met Asp Asp Gly Gln Leu Asp Gly Leu Ala Phe Gly Ala Ile Gln
            20                  25                  30

Leu Asp Gly Asp Gly Asn Ile Leu Gln Tyr Asn Ala Ala Glu Gly Asp
        35                  40                  45
```

```
Ile Thr Gly Arg Asp Pro Lys Gln Val Ile Gly Lys Asn Phe Phe Lys
    50                  55                  60

Asp Val Ala Pro Gly Thr Asp Ser Pro Glu Phe Tyr Gly Lys Phe Lys
65                  70                  75                  80

Glu Gly Val Ala Ser Gly Asn Leu Asn Thr Met Phe Glu Trp Met Ile
                85                  90                  95

Pro Thr Ser Arg Gly Pro Thr Lys Val Lys Ile His Met Lys Lys Ala
                100                 105                 110

Leu Ser Gly Asp Ser Tyr Trp Val Phe Val Lys Arg Val
        115                 120                 125
```

<210> SEQ ID NO 17
<211> LENGTH: 125
<212> TYPE: PRT
<213> ORGANISM: Artificial Sequence
<220> FEATURE:
<223> OTHER INFORMATION: functional PYP

<400> SEQUENCE: 17

```
Met Glu His Val Ala Phe Gly Ser Glu Asp Ile Glu Asn Thr Leu Ala
1               5                   10                  15

Lys Met Asp Asp Gly Gln Leu Asp Gly Leu Ala Phe Gly Ala Ile Gln
                20                  25                  30

Leu Asp Gly Asp Gly Asn Ile Leu Gln Tyr Asn Ala Ala Glu Gly Asp
        35                  40                  45

Ile Thr Gly Arg Asp Pro Lys Gln Val Ile Gly Lys Asn Phe Phe Lys
    50                  55                  60

Asp Val Ala Pro Gly Thr Asp Ser Pro Glu Phe Tyr Gly Lys Phe Lys
65                  70                  75                  80

Glu Gly Val Ala Ser Gly Asn Leu Asn Thr Met Phe Glu Trp Met Ile
                85                  90                  95

Pro Thr Ser Arg Gly Pro Thr Lys Val Lys Val His Met Lys Lys Ala
                100                 105                 110

Leu Ser Gly Asp Ser Tyr Trp Val Phe Ile Lys Arg Val
        115                 120                 125
```

<210> SEQ ID NO 18
<211> LENGTH: 125
<212> TYPE: PRT
<213> ORGANISM: Artificial Sequence
<220> FEATURE:
<223> OTHER INFORMATION: functional PYP

<400> SEQUENCE: 18

```
Met Glu His Val Ala Phe Gly Ser Glu Asp Ile Glu Asn Thr Leu Ala
1               5                   10                  15

Lys Met Asp Asp Gly Gln Leu Asp Gly Leu Ala Phe Gly Ala Ile Gln
                20                  25                  30

Leu Asp Gly Asp Gly Asn Ile Leu Gln Tyr Asn Ala Ala Glu Gly Asp
        35                  40                  45

Ile Thr Gly Arg Asp Pro Lys Gln Val Ile Gly Lys Asn Phe Phe Lys
    50                  55                  60

Asp Val Ala Pro Gly Thr Asp Ser Pro Glu Phe Tyr Gly Lys Phe Lys
65                  70                  75                  80

Glu Gly Val Ala Ser Gly Asn Leu Asn Thr Met Phe Glu Trp Met Ile
                85                  90                  95

Pro Thr Ser Arg Gly Pro Thr Lys Val Lys Ile His Met Lys Lys Ala
                100                 105                 110
```

-continued

```
Leu Ser Gly Asp Ser Tyr Trp Val Phe Ile Lys Arg Val
        115                 120                 125

<210> SEQ ID NO 19
<211> LENGTH: 125
<212> TYPE: PRT
<213> ORGANISM: Artificial Sequence
<220> FEATURE:
<223> OTHER INFORMATION: functional PYP

<400> SEQUENCE: 19

Met Glu His Val Ala Phe Gly Ser Glu Asp Ile Glu Asn Thr Leu Ala
1               5                   10                  15

Lys Met Asp Asp Gly Gln Leu Asp Gly Leu Ala Phe Gly Ala Ile Gln
            20                  25                  30

Leu Asp Gly Asp Gly Asn Ile Leu Gln Tyr Asn Ala Ala Glu Gly Asp
        35                  40                  45

Ile Thr Gly Arg Asp Pro Lys Gln Val Ile Gly Lys Asn Leu Phe Lys
    50                  55                  60

Asp Val Ala Cys Gly Thr Arg Ser Ser Glu Phe Tyr Gly Lys Phe Lys
65                  70                  75                  80

Glu Gly Val Ala Ser Gly Asn Leu Asn Thr Met Phe Glu Trp Met Ile
                85                  90                  95

Pro Thr Ser Arg Gly Pro Thr Lys Val Lys Val His Met Lys Lys Ala
            100                 105                 110

Leu Ser Gly Asp Ser Tyr Trp Val Phe Val Lys Arg Val
        115                 120                 125

<210> SEQ ID NO 20
<211> LENGTH: 125
<212> TYPE: PRT
<213> ORGANISM: Artificial Sequence
<220> FEATURE:
<223> OTHER INFORMATION: functional PYP

<400> SEQUENCE: 20

Met Glu His Val Ala Phe Gly Ser Glu Asp Ile Glu Asn Thr Leu Ala
1               5                   10                  15

Lys Met Asn Asp Gly Gln Leu Asp Gly Leu Ala Phe Gly Ala Ile Gln
            20                  25                  30

Leu Asp Gly Asp Gly Asn Ile Leu Gln Tyr Asn Ala Ala Glu Gly Asp
        35                  40                  45

Ile Thr Gly Arg Asp Pro Lys Gln Val Ile Gly Lys Asn Leu Phe Lys
    50                  55                  60

Asp Val Ala Cys Gly Thr Arg Ser Ser Glu Phe Tyr Gly Lys Phe Lys
65                  70                  75                  80

Glu Gly Val Ala Ser Gly Asn Leu Asn Thr Met Phe Glu Trp Thr Ile
                85                  90                  95

Pro Thr Lys Arg Gly Pro Thr Lys Val Lys Val His Met Lys Lys Ala
            100                 105                 110

Leu Ser Gly Asp Ser Tyr Trp Val Phe Val Lys Arg Val
        115                 120                 125

<210> SEQ ID NO 21
<211> LENGTH: 125
<212> TYPE: PRT
<213> ORGANISM: Artificial Sequence
<220> FEATURE:
<223> OTHER INFORMATION: functional PYP
```

-continued

<400> SEQUENCE: 21

```
Met Glu His Val Ala Phe Gly Ser Glu Asp Ile Glu Asn Thr Leu Ala
1               5                   10                  15

Lys Met Asp Asp Gly Gln Leu Asp Gly Leu Ala Phe Gly Ala Ile Gln
            20                  25                  30

Leu Asp Gly Asp Gly Asn Ile Leu Gln Tyr Asn Ala Ala Glu Gly Asp
            35                  40                  45

Ile Thr Gly Arg Asp Pro Lys Gln Val Ile Gly Lys Asn Leu Phe Lys
        50                  55                  60

Asp Val Ala Glu Gly Thr Arg Ser Ser Glu Phe Tyr Gly Lys Phe Lys
65                  70                  75                  80

Glu Gly Val Ala Ser Gly Asn Leu Asn Thr Met Phe Glu Trp Thr Ile
                85                  90                  95

Pro Thr Lys Arg Gly Pro Thr Lys Val Lys Val His Met Lys Lys Ala
            100                 105                 110

Leu Ser Gly Asp Ser Tyr Trp Val Phe Val Lys Arg Val
            115                 120                 125
```

<210> SEQ ID NO 22
<211> LENGTH: 114
<212> TYPE: PRT
<213> ORGANISM: Artificial Sequence
<220> FEATURE:
<223> OTHER INFORMATION: N-ter fragment

<400> SEQUENCE: 22

```
Met Glu His Val Ala Phe Gly Ser Glu Asp Ile Glu Asn Thr Leu Ala
1               5                   10                  15

Lys Met Asp Asp Gly Gln Leu Asp Gly Leu Ala Phe Gly Ala Ile Gln
            20                  25                  30

Leu Asp Gly Asp Gly Asn Ile Leu Gln Tyr Asn Ala Ala Glu Gly Asp
            35                  40                  45

Ile Thr Gly Arg Asp Pro Lys Gln Val Ile Gly Lys Asn Phe Phe Lys
        50                  55                  60

Asp Val Ala Pro Gly Thr Asp Ser Pro Glu Phe Tyr Gly Lys Phe Lys
65                  70                  75                  80

Glu Gly Val Ala Ser Gly Asn Leu Asn Thr Met Phe Glu Tyr Thr Phe
                85                  90                  95

Asp Tyr Gln Met Thr Pro Thr Lys Val Lys Val His Met Lys Lys Ala
            100                 105                 110

Leu Ser
```

<210> SEQ ID NO 23
<211> LENGTH: 114
<212> TYPE: PRT
<213> ORGANISM: Artificial Sequence
<220> FEATURE:
<223> OTHER INFORMATION: N-ter fragment

<400> SEQUENCE: 23

```
Met Glu His Val Ala Phe Gly Ser Glu Asp Ile Glu Asn Thr Leu Ala
1               5                   10                  15

Lys Met Asp Asp Gly Gln Leu Asp Gly Leu Ala Phe Gly Ala Ile Gln
            20                  25                  30

Leu Asp Gly Asp Gly Asn Ile Leu Gln Tyr Asn Ala Ala Glu Gly Asp
            35                  40                  45
```

```
Ile Thr Gly Arg Asp Pro Lys Gln Val Ile Gly Lys Asn Phe Phe Lys
    50              55                  60

Asp Val Ala Pro Gly Thr Asp Ser Pro Glu Phe Tyr Gly Lys Phe Lys
65              70                  75                  80

Glu Gly Val Ala Ser Gly Asn Leu Asn Thr Met Phe Glu Trp Met Ile
                85                  90                  95

Pro Thr Ser Arg Gly Pro Thr Lys Val Lys Val His Met Lys Lys Ala
            100                 105                 110

Leu Ser

<210> SEQ ID NO 24
<211> LENGTH: 114
<212> TYPE: PRT
<213> ORGANISM: Artificial Sequence
<220> FEATURE:
<223> OTHER INFORMATION: N-ter fragment

<400> SEQUENCE: 24

Met Glu Thr Val Arg Phe Gly Gly Asp Asp Ile Glu Asn Ser Leu Ala
1               5                   10                  15

Lys Met Asp Asp Lys Lys Leu Asp Glu Leu Ala Phe Gly Ala Ile Gln
            20                  25                  30

Leu Asp Ala Asn Gly Lys Ile Ile Gln Tyr Asn Ala Ala Glu Gly Gly
            35                  40                  45

Ile Thr Gly Arg Asp Pro Lys Ser Val Ile Gly Lys Asn Phe Phe Thr
    50              55                  60

Glu Val Ala Pro Gly Thr Gln Ser Lys Glu Phe Gln Gly Arg Phe Lys
65              70                  75                  80

Glu Gly Val Ser Ser Gly Glu Leu Asn Thr Met Phe Glu Trp Met Ile
                85                  90                  95

Pro Thr Ser Arg Gly Pro Thr Lys Val Lys Val His Met Lys Lys Ala
            100                 105                 110

Ile Ser

<210> SEQ ID NO 25
<211> LENGTH: 114
<212> TYPE: PRT
<213> ORGANISM: Artificial Sequence
<220> FEATURE:
<223> OTHER INFORMATION: N-ter fragment

<400> SEQUENCE: 25

Met Glu Thr Val Arg Phe Gly Gly Asp Asp Ile Glu Asn Ala Leu Ala
1               5                   10                  15

Asn Met Asp Asp Lys Lys Leu Asp Thr Leu Ala Phe Gly Ala Ile Gln
            20                  25                  30

Leu Asp Ala Asn Gly Lys Ile Ile Gln Tyr Asn Ala Ala Glu Gly Gly
            35                  40                  45

Ile Thr Gly Arg Asp Pro Lys Ser Val Ile Gly Lys Asn Phe Phe Thr
    50              55                  60

Asp Val Ala Pro Gly Thr Gln Ser Lys Glu Phe Gln Gly Arg Phe Lys
65              70                  75                  80

Glu Gly Val Lys Asn Gly Asp Leu Asn Thr Met Phe Glu Trp Met Ile
                85                  90                  95

Pro Thr Ser Arg Gly Pro Thr Lys Val Lys Val His Met Lys Lys Ala
            100                 105                 110

Leu Ser
```

```
<210> SEQ ID NO 26
<211> LENGTH: 114
<212> TYPE: PRT
<213> ORGANISM: Artificial Sequence
<220> FEATURE:
<223> OTHER INFORMATION: N-ter fragment

<400> SEQUENCE: 26

Met Glu Thr Val Arg Phe Gly Gly Asp Asp Ile Glu Asn Ser Leu Ala
1               5                   10                  15

Lys Met Asp Asp Lys Ala Leu Asp Lys Leu Ala Phe Gly Ala Ile Gln
            20                  25                  30

Leu Asp Gly Asn Gly Lys Ile Ile His Tyr Asn Ala Ala Glu Gly Thr
        35                  40                  45

Ile Thr Gly Arg Asp Pro Lys Thr Val Ile Gly Lys Asn Phe Phe Thr
    50                  55                  60

Asp Val Ala Pro Gly Thr Gln Ser Lys Glu Phe Gln Gly Arg Phe Lys
65                  70                  75                  80

Glu Gly Val Gln Lys Gly Asp Leu Asn Thr Met Phe Glu Trp Met Ile
            85                  90                  95

Pro Thr Ser Arg Gly Pro Thr Lys Val Lys Val His Met Lys Lys Ala
            100                 105                 110

Met Thr

<210> SEQ ID NO 27
<211> LENGTH: 114
<212> TYPE: PRT
<213> ORGANISM: Artificial Sequence
<220> FEATURE:
<223> OTHER INFORMATION: N-ter fragment

<400> SEQUENCE: 27

Met Glu Ile Val Gln Phe Gly Ser Asp Asp Ile Glu Asn Thr Leu Ser
1               5                   10                  15

Lys Met Ser Asp Asp Lys Leu Asn Asp Ile Ala Phe Gly Ala Ile Gln
            20                  25                  30

Leu Asp Ala Ser Gly Lys Ile Ile Gln Tyr Asn Ala Ala Glu Gly Asp
        35                  40                  45

Ile Thr Gly Arg Asp Pro Gly Ala Val Val Gly Lys Asn Phe Phe Asn
    50                  55                  60

Glu Val Ala Pro Gly Thr Asn Ser Pro Glu Phe Lys Gly Arg Phe Asp
65                  70                  75                  80

Glu Gly Val Lys Asn Gly Asn Leu Asn Thr Met Phe Glu Trp Met Ile
            85                  90                  95

Pro Thr Ser Arg Gly Pro Thr Lys Val Lys Val His Met Lys Lys Ala
            100                 105                 110

Leu Thr

<210> SEQ ID NO 28
<211> LENGTH: 114
<212> TYPE: PRT
<213> ORGANISM: Artificial Sequence
<220> FEATURE:
<223> OTHER INFORMATION: N-ter fragment

<400> SEQUENCE: 28

Met Glu Leu Leu Ser Phe Gly Ala Asp Asn Ile Glu Asn Ser Leu Ala
1               5                   10                  15
```

-continued

```
Lys Met Ser Lys Gly Asp Leu Asn Lys Leu Ala Phe Gly Ala Ile Gln
            20                  25                  30

Leu Asn Ala Gln Gly Lys Ile Leu Gln Tyr Asn Ala Ala Glu Gly Asp
            35                  40                  45

Ile Thr Gly Arg Lys Pro Thr Glu Val Ile Gly Lys Asn Phe Phe Leu
    50                  55                  60

Glu Val Ala Pro Gly Thr Asn Arg Thr Glu Phe Lys Gly Arg Phe Asp
65                  70                  75                  80

Gln Gly Ile Lys Ser Gly Asn Leu Asn Thr Met Phe Glu Trp Met Ile
                85                  90                  95

Pro Thr Ser Arg Gly Pro Thr Lys Val Lys Val His Met Lys Lys Ala
            100                 105                 110

Leu Val
```

<210> SEQ ID NO 29
<211> LENGTH: 114
<212> TYPE: PRT
<213> ORGANISM: Artificial Sequence
<220> FEATURE:
<223> OTHER INFORMATION: N-ter fragment

<400> SEQUENCE: 29

```
Met Glu Met Ile Lys Phe Gly Gln Asp Ile Glu Asn Ala Met Ala
1               5                   10                  15

Asp Met Gly Asp Ala Gln Ile Asp Asp Leu Ala Phe Gly Ala Ile Gln
            20                  25                  30

Leu Asp Glu Thr Gly Thr Ile Leu Ala Tyr Asn Ala Ala Glu Gly Glu
            35                  40                  45

Leu Thr Gly Arg Ser Pro Gln Asp Val Ile Gly Lys Asn Phe Phe Lys
    50                  55                  60

Asp Ile Ala Pro Gly Thr Asp Thr Glu Glu Phe Gly Gly Arg Phe Arg
65                  70                  75                  80

Glu Gly Val Ala Asn Gly Asp Leu Asn Ala Met Phe Glu Trp Met Ile
                85                  90                  95

Pro Thr Ser Arg Gly Pro Thr Lys Val Lys Val His Met Lys Arg Ala
            100                 105                 110

Ile Thr
```

<210> SEQ ID NO 30
<211> LENGTH: 114
<212> TYPE: PRT
<213> ORGANISM: Artificial Sequence
<220> FEATURE:
<223> OTHER INFORMATION: N-ter fragment

<400> SEQUENCE: 30

```
Met Glu His Val Ala Phe Gly Ser Gly Asp Ile Glu Asn Thr Leu Ala
1               5                   10                  15

Lys Met Asp Asp Gly Gln Leu Asp Gly Leu Ala Phe Gly Ala Ile Gln
            20                  25                  30

Leu Asp Gly Asp Gly Asn Ile Leu Gln Tyr Asn Ala Ala Glu Gly Asp
            35                  40                  45

Ile Thr Gly Arg Asp Pro Lys Gln Val Ile Gly Lys Asn Phe Phe Lys
    50                  55                  60

Asp Val Ala Pro Gly Thr Asp Ser Pro Glu Phe Tyr Gly Lys Phe Lys
65                  70                  75                  80
```

-continued

```
Glu Gly Val Ala Ser Gly Asn Leu Asn Thr Met Phe Glu Trp Met Ile
                85              90              95

Pro Thr Ser Arg Gly Pro Thr Lys Val Lys Ile His Met Lys Lys Ala
            100             105             110

Leu Ser

<210> SEQ ID NO 31
<211> LENGTH: 114
<212> TYPE: PRT
<213> ORGANISM: Artificial Sequence
<220> FEATURE:
<223> OTHER INFORMATION: N-ter fragment

<400> SEQUENCE: 31

Met Glu His Val Ala Phe Gly Ser Glu Asp Ile Glu Asn Thr Leu Ala
1               5               10              15

Lys Met Asp Asp Gly Gln Leu Asp Gly Leu Ala Phe Gly Ala Ile Gln
                20              25              30

Leu Asp Gly Asp Gly Asn Ile Leu Gln Tyr Asn Ala Ala Glu Gly Asp
            35              40              45

Ile Thr Gly Arg Asp Pro Lys Gln Val Ile Gly Lys Asn Leu Phe Lys
        50              55              60

Asp Val Ala Cys Gly Thr Arg Ser Ser Glu Phe Tyr Gly Lys Phe Lys
65              70              75              80

Glu Gly Val Ala Ser Gly Asn Leu Asn Thr Met Phe Glu Trp Met Ile
                85              90              95

Pro Thr Ser Arg Gly Pro Thr Lys Val Lys Val His Met Lys Lys Ala
            100             105             110

Leu Ser

<210> SEQ ID NO 32
<211> LENGTH: 114
<212> TYPE: PRT
<213> ORGANISM: Artificial Sequence
<220> FEATURE:
<223> OTHER INFORMATION: N-ter fragment

<400> SEQUENCE: 32

Met Glu His Val Ala Phe Gly Ser Glu Asp Ile Glu Asn Thr Leu Ala
1               5               10              15

Lys Met Asn Asp Gly Gln Leu Asp Gly Leu Ala Phe Gly Ala Ile Gln
                20              25              30

Leu Asp Gly Asp Gly Asn Ile Leu Gln Tyr Asn Ala Ala Glu Gly Asp
            35              40              45

Ile Thr Gly Arg Asp Pro Lys Gln Val Ile Gly Lys Asn Leu Phe Lys
        50              55              60

Asp Val Ala Cys Gly Thr Arg Ser Ser Glu Phe Tyr Gly Lys Phe Lys
65              70              75              80

Glu Gly Val Ala Ser Gly Asn Leu Asn Thr Met Phe Glu Trp Thr Ile
                85              90              95

Pro Thr Lys Arg Gly Pro Thr Lys Val Lys Val His Met Lys Lys Ala
            100             105             110

Leu Ser

<210> SEQ ID NO 33
<211> LENGTH: 114
<212> TYPE: PRT
<213> ORGANISM: Artificial Sequence
```

```
<220> FEATURE:
<223> OTHER INFORMATION: N-ter fragment

<400> SEQUENCE: 33

Met Glu His Val Ala Phe Gly Ser Glu Asp Ile Glu Asn Thr Leu Ala
1               5                   10                  15

Lys Met Asp Asp Gly Gln Leu Asp Gly Leu Ala Phe Gly Ala Ile Gln
            20                  25                  30

Leu Asp Gly Asp Gly Asn Ile Leu Gln Tyr Asn Ala Ala Glu Gly Asp
        35                  40                  45

Ile Thr Gly Arg Asp Pro Lys Gln Val Ile Gly Lys Asn Leu Phe Lys
    50                  55                  60

Asp Val Ala Glu Gly Thr Arg Ser Ser Glu Phe Tyr Gly Lys Phe Lys
65                  70                  75                  80

Glu Gly Val Ala Ser Gly Asn Leu Asn Thr Met Phe Glu Trp Thr Ile
                85                  90                  95

Pro Thr Lys Arg Gly Pro Thr Lys Val Lys Val His Met Lys Lys Ala
            100                 105                 110

Leu Ser

<210> SEQ ID NO 34
<211> LENGTH: 11
<212> TYPE: PRT
<213> ORGANISM: Artificial Sequence
<220> FEATURE:
<223> OTHER INFORMATION: C-ter fragment

<400> SEQUENCE: 34

Gly Asp Ser Tyr Trp Val Phe Val Lys Arg Val
1               5                   10

<210> SEQ ID NO 35
<211> LENGTH: 11
<212> TYPE: PRT
<213> ORGANISM: Artificial Sequence
<220> FEATURE:
<223> OTHER INFORMATION: C-ter fragment

<400> SEQUENCE: 35

Gly Asp Thr Tyr Trp Ile Phe Val Lys Arg Leu
1               5                   10

<210> SEQ ID NO 36
<211> LENGTH: 11
<212> TYPE: PRT
<213> ORGANISM: Artificial Sequence
<220> FEATURE:
<223> OTHER INFORMATION: C-ter fragment

<400> SEQUENCE: 36

Gly Asp Thr Phe Trp Ile Phe Val Lys Arg Leu
1               5                   10

<210> SEQ ID NO 37
<211> LENGTH: 11
<212> TYPE: PRT
<213> ORGANISM: Artificial Sequence
<220> FEATURE:
<223> OTHER INFORMATION: C-ter fragment

<400> SEQUENCE: 37

Gly Asp Ser Phe Trp Ile Phe Val Lys Arg Leu
1               5                   10
```

<210> SEQ ID NO 38
<211> LENGTH: 11
<212> TYPE: PRT
<213> ORGANISM: Artificial Sequence
<220> FEATURE:
<223> OTHER INFORMATION: C-ter fragment

<400> SEQUENCE: 38

Gly Asp Thr Tyr Trp Val Phe Val Lys Arg Leu
1               5                   10

<210> SEQ ID NO 39
<211> LENGTH: 11
<212> TYPE: PRT
<213> ORGANISM: Artificial Sequence
<220> FEATURE:
<223> OTHER INFORMATION: C-ter fragment

<400> SEQUENCE: 39

Asp Asp Thr Tyr Trp Val Phe Val Lys Arg Val
1               5                   10

<210> SEQ ID NO 40
<211> LENGTH: 11
<212> TYPE: PRT
<213> ORGANISM: Artificial Sequence
<220> FEATURE:
<223> OTHER INFORMATION: C-ter fragment

<400> SEQUENCE: 40

Gly Asp Ser Tyr Trp Ile Phe Val Lys Arg Val
1               5                   10

<210> SEQ ID NO 41
<211> LENGTH: 11
<212> TYPE: PRT
<213> ORGANISM: Artificial Sequence
<220> FEATURE:
<223> OTHER INFORMATION: C-ter fragment

<400> SEQUENCE: 41

Gly Asp Ser Tyr Trp Val Phe Ile Lys Arg Val
1               5                   10

<210> SEQ ID NO 42
<211> LENGTH: 10
<212> TYPE: PRT
<213> ORGANISM: Artificial Sequence
<220> FEATURE:
<223> OTHER INFORMATION: C-ter fragment

<400> SEQUENCE: 42

Gly Asp Ser Tyr Trp Val Phe Val Lys Arg
1               5                   10

<210> SEQ ID NO 43
<211> LENGTH: 9
<212> TYPE: PRT
<213> ORGANISM: Artificial Sequence
<220> FEATURE:
<223> OTHER INFORMATION: C-ter fragment

<400> SEQUENCE: 43

Gly Asp Ser Tyr Trp Val Phe Val Lys
1               5

<210> SEQ ID NO 44
<211> LENGTH: 8
<212> TYPE: PRT
<213> ORGANISM: Artificial Sequence
<220> FEATURE:
<223> OTHER INFORMATION: C-ter fragment

<400> SEQUENCE: 44

Gly Asp Ser Tyr Trp Val Phe Val
1               5

<210> SEQ ID NO 45
<211> LENGTH: 11
<212> TYPE: PRT
<213> ORGANISM: Artificial Sequence
<220> FEATURE:
<223> OTHER INFORMATION: linker

<400> SEQUENCE: 45

Ser Gly Gly Gly Gly Ser Gly Gly Gly Gly Ser
1               5                   10

<210> SEQ ID NO 46
<211> LENGTH: 342
<212> TYPE: DNA
<213> ORGANISM: Artificial Sequence
<220> FEATURE:
<223> OTHER INFORMATION: N-ter fragment

<400> SEQUENCE: 46
atggagcatg ttgcctttgg cagtgaggac atcgagaaca ctctggccaa aatggacgac        60
ggacaactgg atgggttggc ctttggcgca attcagctcg atggtgacgg gaatatcctg       120
cagtacaatg ctgctgaagg agacatcaca ggcagagatc ccaaacaggt gattgggaag       180
aacttcttca aggatgttgc acctggaacg gattctcccg agttttacgg caaattcaag       240
gaaggcgtag cgtcagggaa tctgaacacc atgttcgaat ggatgatacc gacaagcagg       300
ggaccaacca aggtcaaggt gcacatgaag aaagcccttt cc                         342

<210> SEQ ID NO 47
<211> LENGTH: 342
<212> TYPE: DNA
<213> ORGANISM: Artificial Sequence
<220> FEATURE:
<223> OTHER INFORMATION: N-ter fragment

<400> SEQUENCE: 47
atggagaccg tgagattcgg cggcgacgac atcgagaaca gcctggccaa gatggacgac        60
aagaagctgg acgagctggc cttcggcgcc atccagctgg acgccaacgg caagatcatc       120
cagtacaacg ccgccgaggg cggcatcacc ggcagagacc ccaagagcgt gatcggcaag       180
aacttcttca ccgaggtggc ccccggcacc cagagcaagg agttccaggg cagattcaag       240
gagggcgtga gcagcggcga gctgaacacc atgttcgagt ggatgatccc caccagcaga       300
ggccccacca aggtgaaggt gcacatgaag aaggccatca gc                         342

<210> SEQ ID NO 48
<211> LENGTH: 342
<212> TYPE: DNA
<213> ORGANISM: Artificial Sequence
<220> FEATURE:
<223> OTHER INFORMATION: N-ter fragment

<400> SEQUENCE: 48

-continued

```
atggagaccg tgagattcgg cggcgacgac atcgagaacg ccctggccaa catggacgac        60
aagaagctgg acaccctggc cttcggcgcc atccagctgg acgccaacgg caagatcatc       120
cagtacaacg ccgccgaggg cggcatcacc ggcagagacc ccaagagcgt gatcggcaag       180
aacttcttca ccgacgtggc ccccggcacc cagagcaagg agttccaggg cagattcaag       240
gagggcgtga agaacggcga cctgaacacc atgttcgagt ggatgatccc caccagcaga       300
ggccccacca aggtgaaggt gcacatgaag aaggccctga gc                          342
```

<210> SEQ ID NO 49
<211> LENGTH: 342
<212> TYPE: DNA
<213> ORGANISM: Artificial Sequence
<220> FEATURE:
<223> OTHER INFORMATION: N-ter fragment

<400> SEQUENCE: 49

```
atggagaccg tgagattcgg cggcgacgac atcgagaaca gcctggccaa gatggacgac        60
aaggccctgg acaagctggc cttcggcgcc atccagctgg acggcaacgg caagatcatc       120
cactacaacg ccgccgaggg caccatcacc ggcagagacc ccaagaccgt gatcggcaag       180
aacttcttca ccgacgtggc ccccggcacc cagagcaagg agttccaggg cagattcaag       240
gagggcgtgc agaagggcga cctgaacacc atgttcgagt ggatgatccc caccagcaga       300
ggccccacca aggtgaaggt gcacatgaag aaggccatga cc                          342
```

<210> SEQ ID NO 50
<211> LENGTH: 342
<212> TYPE: DNA
<213> ORGANISM: Artificial Sequence
<220> FEATURE:
<223> OTHER INFORMATION: N-ter fragment

<400> SEQUENCE: 50

```
atggagatcg tgcagttcgg cagcgacgac atcgagaaca ccctgagcaa gatgagcgac        60
gacaagctga cgacatcgc cttcggcgcc atccagctgg acgccagcgg caagatcatc        120
cagtacaacg ccgccgaggg cgacatcacc ggcagagacc ccggcgccgt ggtgggcaag       180
aacttcttca cgaggtggc ccccggcacc aacagccccg agttcaaggg cagattcgac        240
gagggcgtga agaacggcaa cctgaacacc atgttcgagt ggatgatccc caccagcaga       300
ggccccacca aggtgaaggt gcacatgaag aaggccctga cc                          342
```

<210> SEQ ID NO 51
<211> LENGTH: 342
<212> TYPE: DNA
<213> ORGANISM: Artificial Sequence
<220> FEATURE:
<223> OTHER INFORMATION: N-ter fragment

<400> SEQUENCE: 51

```
atggagctgc tgagcttcgg cgccgacaac atcgagaaca gcctggccaa gatgagcaag        60
ggcgacctga acaagctggc cttcggcgcc atccagctga acgcccaggg caagatcctg       120
cagtacaacg ccgccgaggg cgacatcacc ggcagaaagc ccaccgaggt gatcggcaag       180
aacttcttcc tggaggtggc ccccggcacc aacagaaccg agttcaaggg cagattcgac       240
cagggcatca gagcggcaa cctgaacacc atgttcgagt ggatgatccc caccagcaga        300
ggccccacca aggtgaaggt gcacatgaag aaggccctgg tg                          342
```

```
<210> SEQ ID NO 52
<211> LENGTH: 342
<212> TYPE: DNA
<213> ORGANISM: Artificial Sequence
<220> FEATURE:
<223> OTHER INFORMATION: N-ter fragment

<400> SEQUENCE: 52
atggagatga tcaagttcgg ccaggacgac atcgagaacg ccatggccga catgggcgac      60
gcccagatcg acgacctggc cttcggcgcc atccagctgg acgagaccgg caccatcctg     120
gcctacaacg ccgccgaggg cgagctgacc ggcagaagcc cccaggacgt gatcggcaag     180
aacttcttca aggacatcgc ccccggcacc gacaccgagg agttcggcgg cagattcaga     240
gagggcgtgg ccaacggcga cctgaacgcc atgttcgagt ggatgatccc caccagcaga     300 ggcccccacca aggtgaaggt gcacatgaag agagccatca cc                       342

<210> SEQ ID NO 53
<211> LENGTH: 33
<212> TYPE: DNA
<213> ORGANISM: Artificial Sequence
<220> FEATURE:
<223> OTHER INFORMATION: C-ter fragment

<400> SEQUENCE: 53
ggtgacagct attgggtctt tgtgaaacgg gtg                                    33

<210> SEQ ID NO 54
<211> LENGTH: 33
<212> TYPE: DNA
<213> ORGANISM: Artificial Sequence
<220> FEATURE:
<223> OTHER INFORMATION: C-ter fragment

<400> SEQUENCE: 54
ggcgacacct actggatctt cgtgaagaga ctg                                    33

<210> SEQ ID NO 55
<211> LENGTH: 33
<212> TYPE: DNA
<213> ORGANISM: Artificial Sequence
<220> FEATURE:
<223> OTHER INFORMATION: C-ter fragment

<400> SEQUENCE: 55
ggcgacacct tctggatctt cgtgaagaga ctg                                    33

<210> SEQ ID NO 56
<211> LENGTH: 33
<212> TYPE: DNA
<213> ORGANISM: Artificial Sequence
<220> FEATURE:
<223> OTHER INFORMATION: C-ter fragment

<400> SEQUENCE: 56
ggcgacagct tctggatctt cgtgaagaga ctg                                    33

<210> SEQ ID NO 57
<211> LENGTH: 33
<212> TYPE: DNA
<213> ORGANISM: Artificial Sequence
<220> FEATURE:
<223> OTHER INFORMATION: C-ter fragment

<400> SEQUENCE: 57
```

-continued

```
ggcgacacct actgggtgtt cgtgaagaga ctg                              33

<210> SEQ ID NO 58
<211> LENGTH: 33
<212> TYPE: DNA
<213> ORGANISM: Artificial Sequence
<220> FEATURE:
<223> OTHER INFORMATION: C-ter fragment

<400> SEQUENCE: 58
gacgacacct actgggtgtt cgtgaagaga gtg                              33

<210> SEQ ID NO 59
<211> LENGTH: 33
<212> TYPE: DNA
<213> ORGANISM: Artificial Sequence
<220> FEATURE:
<223> OTHER INFORMATION: C-ter fragment

<400> SEQUENCE: 59
ggcgacagct actggatctt cgtgaagaga gtg                              33

<210> SEQ ID NO 60
<211> LENGTH: 30
<212> TYPE: DNA
<213> ORGANISM: Artificial Sequence
<220> FEATURE:
<223> OTHER INFORMATION: C-ter fragment

<400> SEQUENCE: 60
ggtgacagct attgggtctt tgtgaaacgg                                  30

<210> SEQ ID NO 61
<211> LENGTH: 27
<212> TYPE: DNA
<213> ORGANISM: Artificial Sequence
<220> FEATURE:
<223> OTHER INFORMATION: C-ter fragment

<400> SEQUENCE: 61
ggtgacagct attgggtctt tgtgaaa                                     27

<210> SEQ ID NO 62
<211> LENGTH: 24
<212> TYPE: DNA
<213> ORGANISM: Artificial Sequence
<220> FEATURE:
<223> OTHER INFORMATION: C-ter fragment

<400> SEQUENCE: 62
ggtgacagct attgggtctt tgtg                                        24

<210> SEQ ID NO 63
<211> LENGTH: 40
<212> TYPE: DNA
<213> ORGANISM: Artificial Sequence
<220> FEATURE:
<223> OTHER INFORMATION: primer

<400> SEQUENCE: 63
gtggtgctcg agctattagg aaagggcttt cttcatgtgc                       40

<210> SEQ ID NO 64
<211> LENGTH: 44
<212> TYPE: DNA
```

-continued

```
<213> ORGANISM: Artificial Sequence
<220> FEATURE:
<223> OTHER INFORMATION: primer

<400> SEQUENCE: 64
agagtcgcgg ccgcctatta ggaaagggct ttcttcatgt gcac                44

<210> SEQ ID NO 65
<211> LENGTH: 41
<212> TYPE: DNA
<213> ORGANISM: Artificial Sequence
<220> FEATURE:
<223> OTHER INFORMATION: primer

<400> SEQUENCE: 65
gcagcggcgg aggggatcc atggagcatg ttgcctttgg c                    41

<210> SEQ ID NO 66
<211> LENGTH: 78
<212> TYPE: DNA
<213> ORGANISM: Artificial Sequence
<220> FEATURE:
<223> OTHER INFORMATION: primer

<400> SEQUENCE: 66
ggactcagat ctgccaccat ggaacaaaag cttatttctg aagaggactt ggaattcgag    60
atgtggcatg aaggcctg                                             78

<210> SEQ ID NO 67
<211> LENGTH: 55
<212> TYPE: DNA
<213> ORGANISM: Artificial Sequence
<220> FEATURE:
<223> OTHER INFORMATION: primer

<400> SEQUENCE: 67 ggatcccct ccgccgctgc cgcctcctcc ggagacctgc tttgagattc gtcgg          55

<210> SEQ ID NO 68
<211> LENGTH: 78
<212> TYPE: DNA
<213> ORGANISM: Artificial Sequence
<220> FEATURE:
<223> OTHER INFORMATION: primer

<400> SEQUENCE: 68
ggactcagat ctgccaccat ggaacaaaag cttatttctg aagaggactt ggaattcgga    60
gtgcaggtgg aaaccatc                                             78

<210> SEQ ID NO 69
<211> LENGTH: 60
<212> TYPE: DNA
<213> ORGANISM: Artificial Sequence
<220> FEATURE:
<223> OTHER INFORMATION: primer

<400> SEQUENCE: 69 ggatcccct ccgccgctgc cgcctcctcc ggattcttcc agttttagaa gctccacatc    60

<210> SEQ ID NO 70
<211> LENGTH: 31
<212> TYPE: DNA
<213> ORGANISM: Artificial Sequence
<220> FEATURE:
<223> OTHER INFORMATION: primer
```

-continued

<400> SEQUENCE: 70
ttcgtagcta gcatggagca tgttgccttt g                                31

<210> SEQ ID NO 71
<211> LENGTH: 56
<212> TYPE: DNA
<213> ORGANISM: Artificial Sequence
<220> FEATURE:
<223> OTHER INFORMATION: primer

<400> SEQUENCE: 71
aaagcttatt tctgaagagg acttgtaata ggcggccgcg actctagatc ataatc       56

<210> SEQ ID NO 72
<211> LENGTH: 30
<212> TYPE: DNA
<213> ORGANISM: Artificial Sequence
<220> FEATURE:
<223> OTHER INFORMATION: primer

<400> SEQUENCE: 72
ctcaccttgc tcctgccgag aaagtatcca                                  30

<210> SEQ ID NO 73
<211> LENGTH: 30
<212> TYPE: DNA
<213> ORGANISM: Artificial Sequence
<220> FEATURE:
<223> OTHER INFORMATION: primer

<400> SEQUENCE: 73
tggatacttt ctcggcagga gcaaggtgag                                  30

<210> SEQ ID NO 74
<211> LENGTH: 45
<212> TYPE: DNA
<213> ORGANISM: Artificial Sequence
<220> FEATURE:
<223> OTHER INFORMATION: primer

<400> SEQUENCE: 74
ctagagtcgc ggccgcctat taccgtttca caaagaccca atagc                45

<210> SEQ ID NO 75
<211> LENGTH: 48
<212> TYPE: DNA
<213> ORGANISM: Artificial Sequence
<220> FEATURE:
<223> OTHER INFORMATION: primer

<400> SEQUENCE: 75
ctagagtcgc ggccgcctat tatttcacaa agacccaata gctgtcac            48

<210> SEQ ID NO 76
<211> LENGTH: 22
<212> TYPE: DNA
<213> ORGANISM: Artificial Sequence
<220> FEATURE:
<223> OTHER INFORMATION: primer

<400> SEQUENCE: 76
taataggcgg ccgcgactct ag                                         22

<210> SEQ ID NO 77

-continued

```
<211> LENGTH: 23
<212> TYPE: DNA
<213> ORGANISM: Artificial Sequence
<220> FEATURE:
<223> OTHER INFORMATION: primer

<400> SEQUENCE: 77
ggtggcagat ctgagtccgg tag                                                 23

<210> SEQ ID NO 78
<211> LENGTH: 30
<212> TYPE: DNA
<213> ORGANISM: Artificial Sequence
<220> FEATURE:
<223> OTHER INFORMATION: primer

<400> SEQUENCE: 78
caagtcctct tcagaaataa gcttttgttc                                          30

<210> SEQ ID NO 79
<211> LENGTH: 40
<212> TYPE: DNA
<213> ORGANISM: Artificial Sequence
<220> FEATURE:
<223> OTHER INFORMATION: primer

<400> SEQUENCE: 79
gcttatttct gaagaggact tggtgagcaa gggcgaggag                                40

<210> SEQ ID NO 80
<211> LENGTH: 55
<212> TYPE: DNA
<213> ORGANISM: Artificial Sequence
<220> FEATURE:
<223> OTHER INFORMATION: primer

<400> SEQUENCE: 80
gaattcgaag cttgagctcg agatctgagt ccggacttgt acagctcgtc catgc             55

<210> SEQ ID NO 81
<211> LENGTH: 24
<212> TYPE: DNA
<213> ORGANISM: Artificial Sequence
<220> FEATURE:
<223> OTHER INFORMATION: primer

<400> SEQUENCE: 81
ctcgagctca agcttcgaat tctg                                                24

<210> SEQ ID NO 82
<211> LENGTH: 46
<212> TYPE: DNA
<213> ORGANISM: Artificial Sequence
<220> FEATURE:
<223> OTHER INFORMATION: primer

<400> SEQUENCE: 82
ccgctgccgc ctcctccgga agatctgtat cctggctgga atctag                        46

<210> SEQ ID NO 83
<211> LENGTH: 40
<212> TYPE: DNA
<213> ORGANISM: Artificial Sequence
<220> FEATURE:
<223> OTHER INFORMATION: primer

<400> SEQUENCE: 83
```

-continued gcagcggcgg aggggatcc atgcccaaga agaagccgac                          40

<210> SEQ ID NO 84
<211> LENGTH: 46
<212> TYPE: DNA
<213> ORGANISM: Artificial Sequence
<220> FEATURE:
<223> OTHER INFORMATION: primer

<400> SEQUENCE: 84
caagtcctct tcagaaataa gcttttgttc gacgccagca gcatgg                  46

<210> SEQ ID NO 85
<211> LENGTH: 76
<212> TYPE: DNA
<213> ORGANISM: Artificial Sequence
<220> FEATURE:
<223> OTHER INFORMATION: primer

<400> SEQUENCE: 85
gactgcgtga cctgtcttat tccacttacg acgtgatgag tcgaccatga attccaagtc  60
ctcttcagaa ataagc                                                  76

<210> SEQ ID NO 86
<211> LENGTH: 60
<212> TYPE: DNA
<213> ORGANISM: Artificial Sequence
<220> FEATURE:
<223> OTHER INFORMATION: primer

<400> SEQUENCE: 86
ggaataagac aggtcacgca gtcagagcta taggtcggct gagctcatcc ggaggaggcg  60

<210> SEQ ID NO 87
<211> LENGTH: 49
<212> TYPE: DNA
<213> ORGANISM: Artificial Sequence
<220> FEATURE:
<223> OTHER INFORMATION: primer

<400> SEQUENCE: 87
caagtcctct tcagaaataa gcttttgttc ggatcccttc gctgtcatc              49

<210> SEQ ID NO 88
<211> LENGTH: 58
<212> TYPE: DNA
<213> ORGANISM: Artificial Sequence
<220> FEATURE:
<223> OTHER INFORMATION: primer

<400> SEQUENCE: 88
ggaggaggcg gcagcggcgg aggggatcc gaccaattga ctgaagagca gatcgcag    58

<210> SEQ ID NO 89
<211> LENGTH: 40
<212> TYPE: DNA
<213> ORGANISM: Artificial Sequence
<220> FEATURE:
<223> OTHER INFORMATION: primer

<400> SEQUENCE: 89
gctgccgcct cctccggacc gtttcacaaa gacccaatag                        40

<210> SEQ ID NO 90

```
<211> LENGTH: 55
<212> TYPE: DNA
<213> ORGANISM: Artificial Sequence
<220> FEATURE:
<223> OTHER INFORMATION: primer

<400> SEQUENCE: 90
caagtccaag ggcaaggact ccgccgaaca aaagcttatt tctgaagagg acttg            55

<210> SEQ ID NO 91
<211> LENGTH: 51
<212> TYPE: DNA
<213> ORGANISM: Artificial Sequence
<220> FEATURE:
<223> OTHER INFORMATION: primer

<400> SEQUENCE: 91
ggagtccttg cccttggact tgatgcagcc catggtggca gatctgagtc c               51

<210> SEQ ID NO 92
<211> LENGTH: 48
<212> TYPE: DNA
<213> ORGANISM: Artificial Sequence
<220> FEATURE:
<223> OTHER INFORMATION: primer

<400> SEQUENCE: 92
ctaccggact cagatctgcc accagtggtg acagctattg ggtctttg                   48

<210> SEQ ID NO 93
<211> LENGTH: 56
<212> TYPE: DNA
<213> ORGANISM: Artificial Sequence
<220> FEATURE:
<223> OTHER INFORMATION: primer

<400> SEQUENCE: 93
ctagagtcgc ggccgcctat tacataatta cacactttgt ctttgacttc tttttc          56

<210> SEQ ID NO 94
<211> LENGTH: 100
<212> TYPE: DNA
<213> ORGANISM: Artificial Sequence
<220> FEATURE:
<223> OTHER INFORMATION: primer

<400> SEQUENCE: 94
atccaaaaaa gaagagaaag gtagatccaa aaaagaagag aaaggtagat ccaaaaaaga      60
agagaaaggt aggtaccgcc tccggcgatg aggtggatgg                            100

<210> SEQ ID NO 95
<211> LENGTH: 54
<212> TYPE: DNA
<213> ORGANISM: Artificial Sequence
<220> FEATURE:
<223> OTHER INFORMATION: primer

<400> SEQUENCE: 95
ccttgaaatt agcaggtctt gatatcggga gctaataggc ggccgcgact ctag            54

<210> SEQ ID NO 96
<211> LENGTH: 42
<212> TYPE: DNA
<213> ORGANISM: Artificial Sequence
<220> FEATURE:
<223> OTHER INFORMATION: primer
```

<400> SEQUENCE: 96
ctagagtcgc ggccgcctat tacacccgtt tcacaaagac cc                    42

<210> SEQ ID NO 97
<211> LENGTH: 37
<212> TYPE: DNA
<213> ORGANISM: Artificial Sequence
<220> FEATURE:
<223> OTHER INFORMATION: primer

<400> SEQUENCE: 97
ccggactcag atctgccacc atgggtcgtg cgcagtc                         37

<210> SEQ ID NO 98
<211> LENGTH: 47
<212> TYPE: DNA
<213> ORGANISM: Artificial Sequence
<220> FEATURE:
<223> OTHER INFORMATION: primer

<400> SEQUENCE: 98
ctacctttct cttctttttt ggatcggaaa gggctttctt catgtgc              47

<210> SEQ ID NO 99
<211> LENGTH: 39
<212> TYPE: DNA
<213> ORGANISM: Artificial Sequence
<220> FEATURE:
<223> OTHER INFORMATION: primer

<400> SEQUENCE: 99
ccggactcag atctgccacc atgaaggcgg agaggaagc                       39

<210> SEQ ID NO 100
<211> LENGTH: 40
<212> TYPE: DNA
<213> ORGANISM: Artificial Sequence
<220> FEATURE:
<223> OTHER INFORMATION: primer

<400> SEQUENCE: 100
ctccggcgat gaggtggatg gagtgagcaa gggcgaggag                      40

<210> SEQ ID NO 101
<211> LENGTH: 57
<212> TYPE: DNA
<213> ORGANISM: Artificial Sequence
<220> FEATURE:
<223> OTHER INFORMATION: primer

<400> SEQUENCE: 101
gatatcaaga cctgctaatt tcaaggctaa ggatcccttg tacagctcgt ccatgcc    57

<210> SEQ ID NO 102
<211> LENGTH: 60
<212> TYPE: DNA
<213> ORGANISM: Artificial Sequence
<220> FEATURE:
<223> OTHER INFORMATION: primer

<400> SEQUENCE: 102
tgctgaagca ggctggagac gtggaggaga accctggacc tgtgagcaag ggcgaggagg  60

<210> SEQ ID NO 103

-continued

```
<211> LENGTH: 25
<212> TYPE: DNA
<213> ORGANISM: Artificial Sequence
<220> FEATURE:
<223> OTHER INFORMATION: primer

<400> SEQUENCE: 103
taactcgagg actacaagga cgacg                                                 25

<210> SEQ ID NO 104
<211> LENGTH: 50
<212> TYPE: DNA
<213> ORGANISM: Artificial Sequence
<220> FEATURE:
<223> OTHER INFORMATION: primer

<400> SEQUENCE: 104
ctcctcgccc ttgctcacca tgaattcagc gtaatctgga acatcgtatg                      50

<210> SEQ ID NO 105
<211> LENGTH: 36
<212> TYPE: DNA
<213> ORGANISM: Artificial Sequence
<220> FEATURE:
<223> OTHER INFORMATION: primer

<400> SEQUENCE: 105
tggacgagct gtacaagtaa taggcggccg cgactc                                     36

<210> SEQ ID NO 106
<211> LENGTH: 49
<212> TYPE: DNA
<213> ORGANISM: Artificial Sequence
<220> FEATURE:
<223> OTHER INFORMATION: primer

<400> SEQUENCE: 106
cgtcgtcctt gtagtcctcg agttaggaaa gggctttctt catgtgcac                       49

<210> SEQ ID NO 107
<211> LENGTH: 59
<212> TYPE: DNA
<213> ORGANISM: Artificial Sequence
<220> FEATURE:
<223> OTHER INFORMATION: primer

<400> SEQUENCE: 107
cgtcgtcctt gtagtcctcg agttacataa ttacacactt tgtctttgac ttctttttc           59

<210> SEQ ID NO 108
<211> LENGTH: 48
<212> TYPE: DNA
<213> ORGANISM: Artificial Sequence
<220> FEATURE:
<223> OTHER INFORMATION: primer

<400> SEQUENCE: 108
cgtcgtcctt gtagtcctcg agttaccgtt tcacaaagac ccaatagc                        48

<210> SEQ ID NO 109
<211> LENGTH: 45
<212> TYPE: DNA
<213> ORGANISM: Artificial Sequence
<220> FEATURE:
<223> OTHER INFORMATION: primer
```

-continued

```
<400> SEQUENCE: 109
gataatatgg ccacaaccat gcgatcggtg agcaagggcg aggag                    45
```

SPLIT PHOTOACTIVE YELLOW PROTEIN COMPLEMENTATION SYSTEM AND USES THEREOF

CROSS-REFERENCE TO RELATED APPLICATIONS

The present application is a US national stage application of PCT Patent Application No. PCT/EP2020/059635, filed on Apr. 3, 2020, which claims priority to EP Patent Application No. 19305449.1, filed on Apr. 5, 2019. The content of all aforesaid applications is incorporated herein by reference.

FIELD

The present invention pertains to the field of protein detection, notably detection of protein-protein interactions through fluorescent labeling. In particular, the present invention relates to a complementation system comprising two fragments of photoactive yellow protein (PYP), and its use with a fluorogen for detecting interactions between biological molecules of interest, in particular proteins of interest.

BACKGROUND

Interactions between proteins play an essential role in metabolic and signaling pathways, cellular processes, and organismal systems. Because of their central role in biological function, protein interactions control mechanisms leading to healthy and diseased states in organisms. Diseases often result from mutations affecting the binding interface or leading to dysfunctional allosteric changes in proteins. Deciphering protein interaction networks can thus allow understanding of the molecular basis of diseases, which in turn can lead to methods for prevention, diagnosis, and treatment.

For deciphering protein interaction networks, not only is it essential to monitor protein-protein interactions in living cells, but, in addition, the subcellular localization and timing of interactions are important parameters. Fluorescent reporters able to report on protein-protein interactions in space and time are thus of utmost importance for (i) the monitoring of protein-protein interactions in living cells, (ii) the dissection of complex interaction networks, and (iii) the development of high-throughput screening of inhibitors or stabilizers of protein-protein interactions for drug development and biological studies.

The visualization of protein-protein interactions in living cells is in general achieved by Förster resonance energy transfer (FRET) also referred to as fluorescence resonance energy transfer (Piston D W & Kremers G J, Trends Biochem Sci. 2007 September; 32(9):407-14), or by bimolecular fluorescence complementation (BiFC) (Kerppola T K, Annu Rev Biophys. 2008; 37:465-87).

Visualizing protein-protein interactions by FRET necessitates the fusion of two interacting proteins (often called the bait and prey proteins) to two fluorescent proteins (also referred to as fluorophores), acting respectively as FRET donor and FRET acceptor. The FRET donor is able to transfer its excitation energy to the FRET acceptor if the latter is close enough. FRET thus allows the real-time monitoring of complex association and dissociation through the monitoring of how the FRET efficiency changes over time. However, FRET is difficult to implement. It often requires high expression level of the bait and prey proteins to detect energy transfer between the FRET donor and the FRET acceptor. Moreover, structural information is necessary to place the two fluorophores within a distance where energy transfer is efficient. FRET requires also that a large fraction of bait and prey proteins interact to produce a sufficient change in the donor and acceptor fluorescence intensities. In addition, precise quantification of FRET-based interaction is ideally achieved by dedicated systems. Finally, numerous controls and high quantitative accuracy are required to exclude alternative interpretations.

Bimolecular fluorescence complementation (BiFC)-based assays are often preferred to FRET because they are easy to implement, straightforward to interpret and less sensitive to the relative levels of the two interacting proteins. In BiFC assays, the bait and prey proteins are fused to two complementary fragments of a fluorescent protein (FP), which assemble into a functional reporter (so-called split-FP) if the bait and prey proteins do interact. As the two complementary fragments are not fluorescent when taken separately, high contrast is obtained no matter the relative proportion of the two interacting proteins. However, monitoring protein-protein interactions with BiFC has posed its own challenges. First, spontaneous self-assembly of the two complementary fragments can generate unspecific fluorescence background. Furthermore, for BiFC based on proteins of the GFP family, complementation is followed by chromophore maturation, which results in irreversible complex formation (Magliery T J et al., J Am Chem Soc. 2005 Jan. 12; 127(1):146-57). With BiFC based on phytochrome-based infrared proteins, the attachment of the biliverdin chromophore is slow and often also results in irreversibility (Filonov G S & Verkhusha V V, Chem Biol. 2013 Aug. 22; 20(8):1078-86). The slow formation of fluorescent complexes prevents the monitoring of transient protein-protein interactions and the performance of dynamic studies involving active and inactive states, and may induce dominant negative or positive effects.

There is thus a need for an improved fluorescence-based complementation system providing a dynamic system to detect protein-protein interactions. In particular, there is a need for an improved fluorescence-based complementation system characterized by a low self-assembly, to enhance contrast, and by a reversible complex formation, to detect the dissociation of the studied proteins and prevent adverse effect in the studied cells.

Patent application WO2016001437 and Plamont, et al. (Plamont et al., *P Natl Acad Sci Usa* 2016, 113 (3), 497-502) disclose new peptide tags derived from the photoactive yellow protein (PYP). In particular, WO2016001437 and Plamont, et al. (Plamont et al., *P Natl Acad Sci Usa* 2016, 113 (3), 497-502) disclose the yellow fluorescence-activating and absorption-shifting tag (Y-FAST, hereafter "FAST"), which is a fluorogen-based fluorescent reporter developed by the Applicants. FAST is a 14-kDa protein tag derived from the photoactive yellow protein (PYP) which can form complexes with various fluorogens. Detection with FAST relies on two spectroscopic changes for fluorogen activation: increase of fluorescence quantum yield and absorption red-shift. The absorption red-shift undergone by the fluorogen upon binding with FAST ensures higher imaging selectivity and contrast, as unbound or unspecifically bound fluorogen can be discriminated via the choice of the excitation wavelength. In particular, FAST binds fluorogenic hydroxybenzylidene rhodanine (HBR) analogs displaying various spectral properties, such as for example, HMBR (which provides green-yellow fluorescence) and HBR-3,5-DOM (which provides orange-red fluorescence). Fluorogenic HBR analogs are weakly fluorescent in solution but strongly fluoresce when immobilized in the binding cavity of FAST.

Here, the Applicants developed a PYP-based fluorescence complementation system, wherein two PYP fragments, or truncated fragments thereof, assemble reversibly into a functional reporter, or a functional truncated fragment thereof, that binds a fluorogen and thus turns on its fluorescence if the protein(s) of interest to which the PYP fragments are bound do interact. In particular, the Applicants showed that a PYP-based fluorescence complementation system (split-FAST) comprising two fragments of the FAST protein tag, or truncated fragments thereof, displays a low unspecific fluorescence background due to a low self-assembly of the two FAST fragments. The Applicants also demonstrated that split-FAST enables the detection of both the association and dissociation of proteins in cells with high resolution in space and time. The Applicants further demonstrated that split-FAST enables the development of protein and cell-based sensors. The Applicants also developed PYP-based fluorescence complementation systems comprising PYP fragments derived from orthologs of FAST with properties comparable to that of the split-FAST complementation system.

The present invention thus relates to a complementation system comprising a first photoactive yellow protein (PYP) fragment, or a truncated fragment thereof, and a second photoactive yellow protein (PYP) fragment, or a truncated fragment thereof, wherein the first and second PYP fragments are able to reconstitute a functional PYP, or a functional truncated fragment thereof, that binds a fluorogenic chromophore, in particular a fluorogenic hydroxybenzylidene rhodanine (HBR) analog, reversibly. The present invention also relates to methods for detecting an interaction between biological molecules of interest, in particular proteins of interest, and assays relying on the detection of the interaction between two proteins in a sample.

SUMMARY

The present invention relates to a complementation system comprising a first photoactive yellow protein (PYP) fragment and a second photoactive yellow protein (PYP) fragment, wherein:

the first PYP fragment comprises or consists of an amino acid sequence as set forth in SEQ ID NO: 23, or a truncated fragment thereof, or an amino acid sequence having at least about 70% identity with the amino acid sequence as set forth in SEQ ID NO: 23, or a truncated fragment thereof, wherein said truncated fragment comprises at least 89 consecutive amino acids from the C-terminal end of the amino acid sequence as set forth in SEQ ID NO: 23 or of an amino acid sequence having at least about 70% identity with SEQ ID NO: 23; and the second PYP fragment comprises or consists of an amino acid sequence as set forth in SEQ ID NO: 34, or a truncated fragment thereof, or an amino acid sequence having at least about 70% identity with the amino acid sequence as set forth in SEQ ID NO: 34, or a truncated fragment thereof, wherein said truncated fragment comprises at least 8 consecutive amino acids, preferably from the N-terminal end, of the amino acid sequence as set forth in SEQ ID NO: 34 or of an amino acid sequence having at least about 70% identity with SEQ ID NO: 34.

In one embodiment, the first PYP fragment comprises or consists of an amino acid sequence selected from the group comprising or consisting of the amino acid sequences as set forth in SEQ ID NO: 23, SEQ ID NO: 24, SEQ ID NO: 25, SEQ ID NO: 26, SEQ ID NO: 27, SEQ ID NO: 28 and SEQ ID NO: 29, and truncated fragments thereof comprising at least 89 consecutive amino acids from the C-terminal end of said amino acid sequences. In one embodiment, the second PYP fragment comprises or consists of an amino acid sequence selected from the group comprising or consisting of the amino acid sequences as set forth in SEQ ID NO:34, SEQ ID NO: 35, SEQ ID NO: 36, SEQ ID NO: 37, SEQ ID NO: 38, SEQ ID NO: 39 and SEQ ID NO: 40, and truncated fragments thereof comprising at least 8 consecutive amino acids, preferably from the N-terminal end, of said amino acid sequences.

In one embodiment, the first PYP fragment comprises or consists of an amino acid sequence as set forth in SEQ ID NO: 23, SEQ ID NO: 24, SEQ ID NO: 25, SEQ ID NO: 26, SEQ ID NO: 27, SEQ ID NO: 28 or SEQ ID NO: 29, or a truncated fragment thereof comprising at least 89 consecutive amino acids from the C-terminal end of said amino acid sequences; and the second PYP fragment comprises or consists of an amino acid sequence as set forth in SEQ ID NO: 34, SEQ ID NO: 35, SEQ ID NO: 36, SEQ ID NO: 37, SEQ ID NO: 38, SEQ ID NO: 39 or SEQ ID NO: 40, respectively, or a truncated fragment thereof comprising at least 8 consecutive amino acids, preferably from the N-terminal end, of said amino acid sequences.

Thus, in one embodiment, the first PYP fragment comprises or consists of an amino acid sequence as set forth in SEQ ID NO: 23, or a truncated fragment thereof comprising at least 89 consecutive amino acids from the C-terminal end of said amino acid sequence and the second PYP fragment comprises or consists of an amino acid sequence as set forth in SEQ ID NO: 34, or a truncated fragment thereof comprising at least 8 consecutive amino acids, preferably from the N-terminal end, of said amino acid sequence; or the first PYP fragment comprises or consists of an amino acid sequence as set forth in SEQ ID NO: 24, or a truncated fragment thereof comprising at least 89 consecutive amino acids from the C-terminal end of said amino acid sequence and the second PYP fragment comprises or consists of an amino acid sequence as set forth in SEQ ID NO: 35, or a truncated fragment thereof comprising at least 8 consecutive amino acids, preferably from the N-terminal end, of said amino acid sequence; or the first PYP fragment comprises or consists of an amino acid sequence as set forth in SEQ ID NO: 25, or a truncated fragment thereof comprising at least 89 consecutive amino acids from the C-terminal end of said amino acid sequence and the second PYP fragment comprises or consists of an amino acid sequence as set forth in SEQ ID NO: 36, or a truncated fragment thereof comprising at least 8 consecutive amino acids, preferably from the N-terminal end, of said amino acid sequence; or the first PYP fragment comprises or consists of an amino acid sequence as set forth in SEQ ID NO: 26, or a truncated fragment thereof comprising at least 89 consecutive amino acids from the C-terminal end of said amino acid sequence and the second PYP fragment comprises or consists of an amino acid sequence as set forth in SEQ ID NO: 37, or a truncated fragment thereof comprising at least 8 consecutive amino acids, preferably from the N-terminal end, of said amino acid sequence; or the first PYP fragment comprises or consists of an amino acid sequence as set forth in SEQ ID NO: 27, or a truncated fragment thereof comprising at least 89 consecutive amino acids from the C-terminal end of said amino acid sequence and the second PYP fragment comprises or consists of an amino acid sequence as set forth in SEQ ID NO: 38, or a truncated fragment thereof comprising at least 8 consecutive amino acids, preferably from the N-terminal end, of said amino acid sequence; or the first PYP fragment comprises or consists of an amino acid sequence as set forth in SEQ ID NO: 28, or a truncated fragment thereof comprising at least 89 consecutive amino acids from the C-terminal end of said amino acid sequence and the second PYP fragment comprises or consists of an amino acid sequence as set forth in SEQ ID NO: 39, or a truncated fragment thereof comprising at least 8 consecutive amino acids, preferably from the N-terminal end, of said amino acid sequence; or the first PYP fragment comprises or consists of an amino acid sequence as set forth in SEQ ID NO: 29, or a truncated fragment thereof comprising at least 89 consecutive amino acids from the C-terminal end of said amino acid sequence and the second PYP fragment comprises or consists of an amino acid sequence as set forth in SEQ ID NO: 40, or a truncated fragment thereof comprising at least 8 consecutive amino acids, preferably from the N-terminal end, of said amino acid sequence.

In one embodiment, the first PYP fragment comprises or consists of an amino acid sequence as set forth in SEQ ID NO: 23, or a truncated fragment thereof comprising at least 89 consecutive amino acids from the C-terminal end of said amino acid sequence and the second PYP fragment comprises or consists of an amino acid sequence as set forth in SEQ ID NO: 34, SEQ ID NO: 42, SEQ ID NO: 43, or SEQ ID NO: 44.

In one embodiment, the amino acid sequence of the first PYP fragment, or a truncated fragment thereof comprising at least 89 consecutive amino acids from the C-terminal end of said amino acid sequence, further comprises at least one of the following amino acid substitutions with reference to SEQ ID NO: 23: an asparagine at position 19, a leucine at position 62, a cysteine or a glutamic acid at position 68, an arginine at position 71, a serine at position 73, and/or an isoleucine a position 107; and/or wherein the amino acid sequence of the second PYP fragment, or a truncated fragment thereof comprising at least 8 consecutive amino acids of said amino acid sequence, further comprises the following amino acid substitution with reference to SEQ ID NO: 34: an isoleucine at position 8.

The present invention also relates to a kit comprising at least one vector comprising:

a first nucleic acid sequence encoding the first photoactive yellow protein (PYP) fragment, or a truncated fragment thereof, as defined hereinabove; and a second nucleic acid sequence encoding the second photoactive yellow protein (PYP) fragment, or a truncated fragment thereof, as defined hereinabove.

In one embodiment, the kit of the invention comprises:

a first vector comprising the nucleic acid sequence encoding the first photoactive yellow protein (PYP) fragment, or a truncated fragment thereof, as defined hereinabove; and a second vector comprising the nucleic acid sequence encoding the second photoactive yellow protein (PYP) fragment, or a truncated fragment thereof, as defined hereinabove.

According to one embodiment, the complementation system of the invention and the kit of the invention further comprise a fluorogenic hydroxybenzylidene rhodanine (HBR) analog of formula (I):

formula (I)

wherein
R1, R2, R5 and R6 may be identical or different and each represents H, halo, hydroxyl, aryl, alkyl, cycloalkyl, heteroalkyl or heterocycloalkyl group, saturated or unsaturated, linear or branched, optionally substituted by at least one group selected from halo, hydroxyl, oxo, nitro, amido, carboxy, amino, cyano, haloalkoxy, haloalkyl;

R3 represents a non-binding doublet (i.e., a free pair of electrons) or H, halo, hydroxyl, aryl, alkyl, cycloalkyl, heteroalkyl or heterocycloalkyl group, saturated or unsaturated, linear or branched, optionally substituted by at least one group selected from halo, hydroxyl, oxo, nitro, amido, carboxy, amino, cyano, haloalkoxy, haloalkyl;

R4 is a single or a double bound, interrupted or terminated by S, O or N atom, optionally substituted by at least one group selected from H, hydroxyl, aryl, alkyl, cycloalkyl, heteroalkyl or heterocycloalkyl group, saturated or unsaturated, linear or branched, optionally substituted by at least one group selected from halo, hydroxyl, oxo, nitro, amido, carboxy, amino, cyano, haloalkoxy, haloalkyl;

X is OH, SH, NHR7, or $N(R7)_2$, wherein R7 is H, halo, hydroxyl, aryl, alkyl, cycloalkyl, heteroalkyl or heterocycloalkyl group, saturated or unsaturated, linear or branched, optionally substituted by at least one group selected from halo, hydroxyl, oxo, nitro, amido, carboxy, amino, cyano, haloalkoxy, haloalkyl; and Y is O, NH or S.

In one embodiment, the fluorogenic HBR analog is selected from the group comprising or consisting of 4-hydroxy-3-methylbenzylidene rhodanine (HMBR), (Z)-2-(5-(4-hydroxy-3-methoxybenzylidene)-4-oxo-2-thioxothiazolidin-3-yl)acetic acid (HBR-3OM), (Z)-2-(5-(4-hydroxy-3, 5-dimethylbenzylidene)-4-oxo-2-thioxothiazolidin-3-yl) acetic acid (HBR-3,5DM) and (Z)-2-(5-(4-hydroxy-3, 5-dimethoxybenzylidene)-4-oxo-2-thioxothiazolidin-3-yl) acetic acid (HBR-3,5DOM).

The present invention also relates to a method for detecting an interaction between two biological molecules of interest in a sample, preferably two proteins of interest, comprising the steps of:

fusing a first photoactive yellow protein (PYP) fragment, or a truncated fragment thereof, as defined hereinabove, to a first biological molecule of interest, thereby tag-
ging the first biological molecule of interest with said
first PYP fragment;

fusing a second photoactive yellow protein (PYP) frag-
ment, or a truncated fragment thereof, as defined here-
inabove, to a second biological molecule of interest,
thereby tagging the second biological molecule of
interest with said second PYP fragment;

contacting the sample with a fluorogenic hydroxyben-
zylidene rhodanine (HBR) analog; and detecting a fluorescence resulting from the binding of the
fluorogenic HBR analog to the functional PYP, or a
functional truncated fragment thereof, reconstituted
upon interaction of the two biological molecules of
interest;

thereby detecting the interaction of the two biological mol-
ecules of interest present in the sample, through the binding
of the fluorogenic HBR analog to the functional PYP, or a
functional truncated fragment thereof, reconstituted upon
interaction of the two biological molecules of interest.

In one embodiment, the method of the invention is for
monitoring over time and/or space the association and
dissociation of the two biological molecules of interest,
preferably of the two proteins of interest, through the
detection of the interaction between said biological mol-
ecules of interest.

The present invention also relates to a screening method
for identifying a new protein-protein interaction between
two protein candidates of interest in a sample, comprising
the steps of:

fusing a first photoactive yellow protein (PYP) fragment,
or a truncated fragment thereof, as defined hereinabove,
to a first protein candidate of interest, thereby tagging
the first protein candidate of interest with said first PYP
fragment;

fusing a second photoactive yellow protein (PYP) frag-
ment, or a truncated fragment thereof, as defined here-
inabove, to a second protein candidate of interest,
thereby tagging the second protein candidate of interest
with said second PYP fragment;

contacting the sample with a fluorogenic hydroxyben-
zylidene rhodanine (HBR) analog; and detecting a fluorescence resulting from the binding of the
fluorogenic HBR analog to the functional PYP, or a
functional truncated fragment thereof, reconstituted
upon interaction of the two protein candidates of inter-
est;

thereby identifying a new protein-protein interaction
between the two protein candidates of interest present in the
sample, through the binding of the fluorogenic HBR analog
to the functional PYP, or a functional truncated fragment
thereof, reconstituted upon interaction of the two protein
candidates of interest.

The present invention also relates to an assay relying on
the detection of the interaction between two proteins in a
sample, said assay comprising the steps of:

obtaining a first tagged protein, wherein the protein is
tagged with a first photoactive yellow protein (PYP)
fragment, or a truncated fragment thereof, as defined
hereinabove;

obtaining a second tagged protein, wherein the protein is
tagged with a second photoactive yellow protein (PYP)
fragment, or a truncated fragment thereof, as defined
hereinabove;

contacting the sample with a fluorogenic hydroxyben-
zylidene rhodanine (HBR) analog; and detecting a fluorescence resulting from the binding of the
fluorogenic HBR analog to the functional PYP, or a
functional truncated fragment thereof, reconstituted
upon interaction of the two proteins;

thereby detecting the interaction of the two proteins present
in the sample, through the binding of the fluorogenic HBR
analog to the functional PYP, or a functional truncated
fragment thereof, reconstituted upon interaction of the two
proteins.

In one embodiment, the assay of the invention is for
assessing the capacity of a molecule of interest to stabilize
or to inhibit protein-protein interactions. In one embodi-
ment, the assay of the invention is for assessing a signaling
pathway of interest, with the interaction of the two proteins
depending on the activation of the signaling pathway of
interest; or is for assessing the capacity of a molecule of
interest to modulate said signaling pathway of interest.

Definitions

As used herein, the term "about" preceding a figure means
plus or minus 10%, or less, of the value of said figure. It is
to be understood that the value to which the term "about"
refers is itself also specifically, and preferably, disclosed.

As used herein, the term "alkoxy" refers to any O-alkyl
group. Suitable alkoxy groups include ethoxy and methoxy.

As used herein, the term "alkyl" refers to a hydrocarbyl
radical of formula $C_nH_{2n+1}$ wherein n is a number greater
than or equal to 1. Generally, alkyl groups of this invention
comprise from 1 to 12 carbon atoms, preferably from 1 to 6
carbon atoms. Alkyl groups may be linear or branched and
may be substituted as indicated herein. Suitable alkyl groups
include methyl, ethyl, propyl (n-propyl, i-propyl), butyl
(n-butyl, i-butyl, s-butyl and t-butyl), pentyl and its isomers
(e.g., n-pentyl, iso-pentyl), and hexyl and its isomers (e.g.,
n-hexyl, iso-hexyl).

As used herein, the term "amido" refers to the —NR—
CO— function wherein R may be —H or an alkyl group.

As used herein, the term "amino" refers to a —NH$_2$ group
or any group derived thereof by substitution of one or two
hydrogen atom(s) by an organic aliphatic or aromatic group.
Preferably, groups derived from —NH$_2$ are alkylamino
groups, i.e., N-alkyl groups, comprising monoalkylamino
and dialkylamino. According to a specific embodiment, the
term "amino" refers to NH$_2$, NHMe or NMe$_2$.

As used herein, the term "amino acid" refers to both
natural and synthetic amino acids, and both D- and L-amino
acids. They are represented by their full name, their three-
letter code or their one-letter code as well-known in the art.
Amino acid residues in peptides are thus abbreviated as
follows: phenylalanine is Phe or F; leucine is Leu or L;
isoleucine is Ile or I; methionine is Met or M; valine is Val
or V; serine is Ser or S; proline is Pro or P; threonine is Thr
or T; alanine is Ala or A; tyrosine is Tyr or Y; histidine is His
or H; glutamine is Gln or Q; asparagine is Asn or N; lysine
is Lys or K; aspartic acid is Asp or D; glutamic acid is Glu
or E; cysteine is Cys or C; tryptophan is Trp or W; arginine
is Arg or R; and glycine is Gly or G. "Standard amino acid"
or "naturally occurring amino acid" means any of the twenty
standard L-amino acids commonly found in naturally occur-
ring peptides. "Non-standard amino acid" means any amino
acid, other than the standard amino acids, regardless of
whether it is prepared synthetically or derived from a natural
source. For example, naphtlylalanine can be substituted for
tryptophan to facilitate synthesis. Other synthetic amino
acids that can be substituted include, but are not limited to,
L-hydroxypropyl, L-3,4-dihydroxyphenylalanyl, alpha-amino acids such as L-alpha-hydroxylysyl and D-alpha-methylalanyl, L-alpha-methylalanyl, beta-amino acids, and isoquinolyl. The PYP fragments of the invention may comprise standard amino acids or non-standard amino acids. The term "amino acid" also encompasses chemically modified amino acids, including, but not limited to, salts, amino acid derivatives (such as amides), and substitutions. Amino acids contained within the polypeptides of the present invention (i.e., PYP fragments and fusion proteins of the present invention), and particularly at the carboxy- or amino-terminus, can thus be modified by methylation, amidation, acetylation or substitution with other chemical groups which can change the circulating half-life of the polypeptides without adversely affecting their activity. Additionally, a disulfide linkage may be present or absent in the polypeptides of the invention. Other polypeptide mimetics encompassed herein include polypeptides of the present invention (i.e., PYP fragments and fusion proteins of the present invention) having the following modifications: i) polypeptides wherein one or more of the peptidyl —C(O)NR— linkages (bonds) have been replaced by a non-peptidyl linkage such as a —CH$_2$-carbamate linkage (—CH$_2$OC(O)NR—), a phosphonate linkage, a —CH$_2$-sulfonamide (—CH$_2$—S(O)$_2$NR—) linkage, a urea (—NHC(O)NH—) linkage, a —CH$_2$-secondary amine linkage, or with an alkylated peptidyl linkage (—C(O)NR—) wherein R is C$_1$-C$_4$ alkyl; ii) polypeptides wherein the N-terminus is derivatized to a —NRR$^1$ group, to a —NRC(O)R group, to a —NRC(O)OR group, to a —NRS(O)$_2$R group, to a —NHC(O)NHR group, where R and R$^1$ are hydrogen or C$_1$-C$_4$ alkyl with the proviso that R and R$^1$ are not both hydrogen; iii) polypeptides wherein the C terminus is derivatized to —C(O)R$^2$, where R$^2$ is selected from the group consisting of C$_1$-C$_4$ alkoxy, and —NR$^3$R$^4$, where R$^3$ and R$^4$ are independently selected from the group consisting of hydrogen and C$_1$-C$_4$ alkyl.

As used herein, the term "aryl" refers to a polyunsaturated, aromatic hydrocarbyl group having a single ring (i.e., phenyl) or multiple aromatic rings fused together (e.g., naphtyl) or linked covalently, typically containing 5 to 12 atoms, preferably 6 to 10, wherein at least one ring is aromatic. The aromatic ring may optionally include one to two additional ring(s) (either cycloalkyl, heterocyclyl or heteroaryl) fused thereto. Aryl is also intended to include the partially hydrogenated derivatives of the carbocyclic systems enumerated herein. Non-limiting examples of aryl comprise phenyl, biphenylyl, biphenylenyl, 5- or 6-tetralinyl, naphthalen-1- or -2-yl, 4-, 5-, 6 or 7-indenyl, 1-2-, 3-, 4- or 5-acenaphtylenyl, 3-, 4- or 5-acenaphtenyl, 1- or 2-pentalenyl, 4- or 5-indanyl, 5-, 6-, 7- or 8-tetrahydronaphthyl, 1,2,3,4-tetrahydronaphthyl, 1,4-dihydronaphthyl, 1-, 2-, 3-, 4- or 5-pyrenyl.

As used herein, the term "carboxy" refers to the —COOH function, including —COO⁻ and salts thereof.

As used herein, the term "cyano" refers to the —C≡N function.

As used herein, the term "cycloalkyl" refers to a cyclic alkyl group, that is to say, a monovalent, saturated, or unsaturated hydrocarbyl group having 1 or 2 cyclic structure(s). Cycloalkyl includes monocyclic or bicyclic hydrocarbyl groups. Cycloalkyl groups may comprise 3 or more carbon atoms in the ring and generally, according to this invention, comprise from 3 to 10 carbon atoms, preferably from 3 to 8 carbon atoms, more preferably from 3 to 6 carbon atoms. Examples of cycloalkyl groups include, but are not limited to, cyclopropyl, cyclobutyl, cyclopentyl, cyclohexyl.

As used herein the term "complementation system" refers to a system comprising at least two components, e.g., two fragments of a polypeptide or protein, that together form a structure having a property of interest, such as for instance the capacity to bind a fluorogenic chromophore, that each component taken separately, e.g., each polypeptide fragment, does not have. Accordingly, the term "complementation" refers to the reconstitution of the structure having the property of interest, such as for instance the capacity to bind a fluorogenic chromophore. For example, the term "complementation" refers to the reconstitution of a polypeptide (or protein) scaffold when the two fragments of said polypeptide (or protein) are in close proximity, the reconstituted polypeptide (or protein) scaffold then having the capacity to bind a fluorogenic chromophore.

As used herein, the term "functional PYP" refers to a photoactive yellow protein (PYP) able to bind to a fluorogenic HBR analog, preferably reversibly. Accordingly, as used herein, the term "functional truncated fragment of PYP" refers to a truncated fragment of photoactive yellow protein (PYP) still able to bind to a fluorogenic HBR analog, preferably reversibly.

As used herein, the terms "fluorogenic chromophore" or "fluorogen" refer to a chromophore, the brightness of which can be significantly enhanced by an environmental change. A fluorogenic chromophore is substantially non-fluorescent in solution under its free form, but brightens up when placed into an environment constraining its conformation and excluding deexcitation of its excited state by non-radiative pathways. In one embodiment of the invention, the fluorogenic chromophore, e.g., the fluorogenic 4-hydroxybenzylidene-rhodanine (HBR) analog, is almost invisible in solution and becomes fluorescent upon binding of a protein scaffold, such as the one formed by the complementation of the PYP fragments of the invention.

As used herein, the term "fluorogenic HBR analog" refers to a fluorogenic 4-hydroxybenzylidene-rhodanine (HBR) analog (also referred to as fluorogenic hydroxybenzylidene-rhodanine (HBR) analog) which absorbs light at a specific frequency and is thus colored, and has the properties of a fluorogenic chromophore. In one embodiment, as described hereinafter, the fluorogenic HBR analog is a compound of formula (I).

As used herein, the term "halo" means fluoro, chloro, bromo or iodo. Preferred halo groups are fluoro and chloro.

As used herein, the term "haloalkyl" refers to any alkyl group substituted by one or more halo group(s). Examples of preferred haloalkyl groups are CF$_3$, CHF$_2$ and CH$_2$F.

As used herein, the term "haloalkoxy" refers to any alkoxy group substituted by one or more halo group(s).

As used herein, the term "heteroalkyl" refers to an alkyl group wherein at least one carbon atom is replaced by a heteroatom; preferably, said heteroatom is selected from N, S, P or O. In heteroalkyl groups, the heteroatoms are bound along the alkyl chain only to carbon atoms, i.e., each heteroatom is separated from any other heteroatom by at least one carbon atom. However, the nitrogen, sulfur and phosphorus heteroatoms may optionally be oxidized, and the nitrogen heteroatoms may optionally be quaternized. Heteroalkyl groups especially include alkoxy groups.

As used herein, the term "heterocycloalkyl" refers to a cycloalkyl group wherein at least one carbon atom is replaced by a heteroatom; preferably, said heteroatom is selected from N, S, P or O. In heterocycloalkyl groups, the heteroatoms are bound along the alkyl chain only to carbon atoms, i.e., each heteroatom is separated from any other heteroatom by at least one carbon atom. However, the nitrogen, sulfur and phosphorus heteroatoms may optionally be oxidized, and the nitrogen heteroatoms may optionally be quaternized.

As used herein, the term "hydroxyl" refers to the —OH function.

As used herein, the term "identity", when used in a relationship between the sequences of two or more polypeptides or of two or more nucleic acid, refers to the degree of sequence relatedness between polypeptides or nucleic acids (respectively), as determined by the number of matches between strings of two or more amino acid residues or of two or more nucleotides, respectively. "Identity" measures the percent of identical matches between the smaller of two or more sequences with gap alignments (if any) addressed by a particular mathematical model or computer program (i.e., "algorithms"). Identity of related polypeptides or nucleic acid sequences can be readily calculated by known methods. Such methods include, but are not limited to, those described in Arthur M. Lesk, *Computational Molecular Biology: Sources and Methods for Sequence Analysis* (New-York: Oxford University Press, 1988); Douglas W. Smith, *Biocomputing: Informatics and Genome Projects* (New-York: Academic Press, 1993); Hugh G. Griffin and Annette M. Griffin, *Computer Analysis of Sequence Data, Part* 1 (New Jersey: Humana Press, 1994); Gunnar von Heinje, *Sequence Analysis in Molecular Biology: Treasure Trove or Trivial Pursuit* (Academic Press, 1987); Michael Gribskov and John Devereux, *Sequence Analysis Primer* (New York: M. Stockton Press, 1991); and Carillo et al., 1988. *SIAM J. Appl. Math.* 48(5):1073-1082. Preferred methods for determining identity are designed to give the largest match between the sequences tested. Methods of determining identity are described in publicly available computer programs. Preferred computer program methods for determining identity between two sequences include the GCG program package, including GAP (Devereux et al., 1984. *Nucl. Acid. Res.* 12(1 Pt 1):387-395; Genetics Computer Group, University of Wisconsin Biotechnology Center, Madison, WI), BLASTP, BLASTN, TBLASTN and FASTA (Altschul et al., 1990. *J. Mol. Biol.* 215(3):403-410). The BLASTX program is publicly available from the National Center for Biotechnology Information (NCBI) and other sources (BLAST Manual, Altschul et al. NCB/NLM/ NIH Bethesda, Md. 20894; Altschul et al., 1990. *J. Mol. Biol.* 215(3):403-410). The well-known Smith Waterman algorithm may also be used to determine identity.

As used herein, the term "nitro" refers to the —NO₂ function.

As used herein the term "nucleic acid" refers to a polymer of nucleotides covalently linked by phosphodiester bonds, such as deoxyribonucleic acids (DNA) or ribonucleic acids (RNA), in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, single nucleotide polymorphisms (SNPs), and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-

2608 (1985); and Rossolini et al., Mol. Cell. Probes 8:91-98 (1994)). Unless otherwise specified, a nucleotide sequence encoding an amino acid sequence includes all nucleotide sequences that are degenerate versions of each other and that encode the same amino acid sequence. The phrase nucleotide sequence that encodes a protein or a RNA may also include introns to the extent that the nucleotide sequence encoding the protein may in some version contain an intron(s).

As used herein, the term "oxo" refers to the —C=O function.

As used herein, the term "PYP fragment" refers to a peptide or polypeptide originating from a functional photoactive yellow protein PYP, but not comprising itself a functional photoactive yellow protein (PYP), the latter only being able to bind a fluorogenic HBR analog. In other words, as used herein, the term "PYP fragment" refers to a peptide or polypeptide originating from a functional photoactive yellow protein PYP but not able on its own to bind a fluorogenic HBR analog. Accordingly, not being able to bind a fluorogenic HBR analog on its own, a PYP fragment as described herein (e.g., a first PYP fragment or a second PYP fragment) cannot induce or generate fluorescence on its own.

As used herein, the term "reporter protein" refers to a protein the interactions of which may be detected, localized or quantified as a way to indirectly assess a target of interest or a mechanism of interest.

As used herein, the term "sample" refers to a specimen or small quantity of material, in particular of biological material, generally solid or liquid. "Sample" may thus also refer to cells or tissues or organisms of interest.

BRIEF DESCRIPTION OF THE DRAWINGS

FIGS. 4A-4D are a set of histograms showing the relative in-cell brightness of various split-FAST with different fluorogenic HBR analogs as indicated (4A: HMBR, 4B: HBR-3,5DM, 4C: HBR-30M, and 4D: HBR-3,5DOM) in function of the C-terminal fragment CFASTn (n=11, 10 or 9) and the N-terminal fragment used. The iFAST label indicates when NFAST from iFAST (i.e., the first PYP fragment according to the invention consisting of the amino acid sequence NFAST with an isoleucine at position 107 instead of a valine as set forth in SEQ ID NO: 30) was used. If absent, NFAST from FAST was used (i.e., the first PYP fragment according to the invention consisting of the amino acid sequence as set forth in SEQ ID NO: 23). CFAST11, CFAST10 and CFAST9 correspond to the second PYP fragment according to the invention consisting of the amino acid sequence as set forth in SEQ ID NO: 34, SEQ ID NO: 42 and SEQ ID NO: 43, respectively. NFAST fragments were fused to FRB and CFAST fragments were fused to FKBP. Complementation was induced by addition of rapamycin. Split-FAST fluorescence was normalized by expression level using the fluorescence of co-expressed fluorescent proteins.

FIGS. 5A-5G illustrate the detection of rapamycin-induced FRB-FKBP dimerization with the complementation system of the invention. 5A and 5B show HEK293T cells co-expressing FKBP-NFAST and FRB-CFASTn (n=10 or 11) which were labeled with 5 μM HMBR (5A) or 10 μM HBR-3,5DOM (5B) and imaged before and after addition of 100 nM rapamycin. Scale bars 10 μm. 5C shows the fluorescence fold increase upon FKBP-FRB association (mean±sem, n=84, 83, 107, 112 cells respectively from 3-4 experiments). 5D shows the temporal evolution of the fluorescence intensity after rapamycin addition in HMBR-treated cells co-expressing FKBP-NFAST and FRB-CFASTI1 (n=11 cells). 5E shows the evolution of the cellular fluorescence of HMBR-labeled HEK293 cells expressing FAST, split-FAST11 (resulting from the complementation of NFAST and CFAST11), and split-FAST10 (resulting from the complementation of NFAST and CFAST10) upon imaging by confocal microscopy. Cells expressing FRB-NFAST and FKBP-CFASTn (n=10 or 11) were treated with rapamycin to form split-FAST11 and split-FAST10. Cells expressing FAST were used as control. HMBR concentration was 10 μM. Excitation at 488 nm at 6.3 kW/cm2. Six cells were analyzed per condition. 5F shows selected time lapse frames of representative HEK293 cells co-expressing FKBP-NFAST and FRB-CFASTn (n=10 or 11) (labeled with 5 μM HMBR) upon addition of 100 nM rapamycin. Scale bars 20 μm. 5G shows selected frames of representative HEK293 cells co-expressing FKBP-NFAST and FRB-CFAST11 (labeled with 10 μM HBR-3,5DOM) upon addition of 100 nM rapamycin. Scale bars 20 μm.

FIGS. 6A-6F illustrate the detection of rapamycin-induced dissociation of AP1510-induced FKBP homodimers with the complementation system of the invention. 6A and 6B show AP1510-treated HEK293T cells co-expressing FKBP-NFAST and FKBP-CFASTn (n=10 or 11) which were labeled with 5 μM HMBR (6A) or 10 μM HBR-3,5DOM (6B) and imaged before and after addition of 1 μM rapamycin. Scale bars 10 μm. 6C shows the fluorescence fold decrease upon FKBP-FKBP dissociation (mean±sem, n=142, 175, 219, 125 cells respectively from 3-4 experiments). 6D shows the temporal evolution of the fluorescence intensity after rapamycin addition in HMBR-labeled, AP1510-treated cells co-expressing FKBP-NFAST and FKBP-CFAST11 (n=8 cells). 6E shows selected time lapse frames of representative AP1510-treated HEK293 cells co-expressing FKBP-NFAST and FKBP-CFASTn (n=10 or 11) (labeled with 5 μM HMBR) upon addition of 1 μM rapamycin. Scale bars 20 μm. 6F shows selected time lapse frames of representative AP1510-treated HEK293 cells co-expressing FKBP-NFAST and FKBP-CFAST11 (labeled with 10 μM HBR-3,5DOM) upon addition of 1 μM rapamycin. Scale bars 20 μm.

FIGS. 8A and 8B illustrate the detection of the interaction between a membrane protein and a cytosolic protein with the complementation system of the invention. 8A shows HEK293T cells co-expressing Lyn11-FRB-NFAST and FKBP-CFASTn (n=10 or 11) which were labeled with 5 μM HMBR and imaged before and after addition of 100 nM rapamycin. Scale bars 10 μm. 8B shows the temporal evolution of the fluorescence intensity after rapamycin addition in HMBR-treated cells co-expressing Lyn11-FRB-NFAST and FKBP-CFAST11.

FIGS. 12A and 12B illustrate the use of split-FAST for detecting caspase-3 activity. 12A depicts the experimental design. N and C represent the first and second PYP fragments according to the invention (NFAST and CFAST11, respectively) able to interact and thus to reconstitute a functional PYP that can reversibly bind a fluorogen and turn on its fluorescence. The sensor consists of bFos-CFAST11 and bJun-NFAST-NLS3-DEVDG-mCherry-NES. 12B shows the temporal evolution of the nuclear split-FAST fluorescence intensity after treatment with staurosporine in HMBR-treated cells (n=9 cells).

DETAILED DESCRIPTION

Figures 1A, 1B:
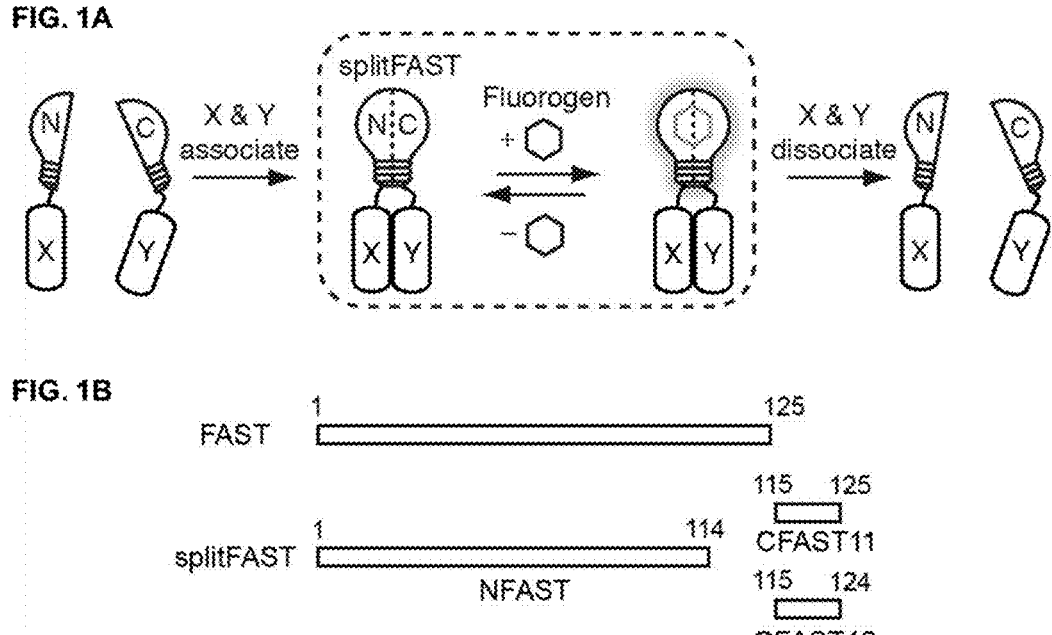
FIGS. 1A and 1B are a schematic representation of the working principle (1A) and design (1B) of the fluorescence complementation system of the invention. N and C represent the first and second PYP fragments according to the invention, respectively, able to interact and thus to reconstitute a functional PYP that can reversibly bind a fluorogen and turn on its fluorescence; X and Y represent the potentially interacting protein(s) of interest, to which the PYP fragments are fused. FAST corresponds to the PYP consisting of the amino acid sequence as set forth in SEQ ID NO: 9. NFAST corresponds to the first PYP fragment according to the invention consisting of the amino acid sequence as set forth in SEQ ID NO: 23. CFAST11 corresponds to the second PYP fragment according to the invention consisting of the amino acid sequence as set forth in SEQ ID NO: 34. CFAST10 corresponds to the second PYP fragment according to the invention consisting of the amino acid sequence as set forth in SEQ ID NO: 42. Split-FAST corresponds to the reconstituted functional PYP, i.e., FAST, resulting from the complementation of the two FAST fragments, NFAST and either CFAST11 or CFAST10.

The present invention relates to a complementation system comprising two photoactive yellow protein (PYP) fragments as described herein, a first PYP fragment and a second PYP fragment, or truncated fragments thereof.

According to the present invention, the complementation system comprises a first PYP fragment and a second PYP fragment, or truncated fragments thereof, wherein the first and second PYP fragments are able to associate with each other and thus to reconstitute a functional PYP, or a functional truncated fragment thereof, that binds a fluorogenic hydroxybenzylidene rhodanine (HBR) analog, preferably reversibly. As mentioned hereinabove, only a functional PYP or a functional truncated fragment thereof, such as a reconstituted functional PYP or a reconstituted functional fragment thereof, is able to bind a fluorogenic HBR analog. The first PYP fragment of the invention and the second PYP fragment of the invention, or truncated fragments thereof, are not able on their own to bind a fluorogenic HBR analog, and therefore are not able on their own to induce or generate fluorescence, which is emitted by a fluorogenic HBR analog upon binding to a functional PYP, or a functional truncated fragment thereof.

"Photoactive yellow protein" or "PYP" is a photoreceptor protein isolated, for instance, from purple photosynthetic bacteria *Ectothiorhodospira halophila* (*Halorhodospira halophila*). The wild-type PYP is a relatively small protein (14 kDa), which can bind p-coumaric acid, a chromophore, through a thioester covalent bond with the 69th cysteine residue.

According to the present invention, the two PYP fragments or truncated fragments thereof, of the complementation system reconstitute the structure of a functional PYP, or a functional truncated fragment thereof, when they are in close proximity, with the functional PYP being capable of binding a fluorogenic hydroxybenzylidene-rhodanine (HBR) analog. As mentioned hereinabove, the two PYP fragments or truncated fragments thereof, of the complementation system of the invention are able to associate with each other when they are in close proximity.

In one embodiment, by close proximity it is meant a distance shorter than about 20 nm, preferably shorter than about 10 nm, and more preferably shorter than about 5 nm.

Thus, according to the present invention, the reconstituted functional PYP, or the reconstituted functional truncated fragment thereof, is able to bind a fluorogenic HBR analog. Preferably, in one embodiment, the reconstituted functional PYP, or the reconstituted functional truncated fragment thereof, is able to bind a fluorogenic HBR analog reversibly.

In the present invention, by reconstitution of a functional PYP (or in short reconstitution of a PYP), it is meant reconstitution of the structure of a functional PYP, or a functional truncated fragment thereof, allowing the binding of a fluorogenic hydroxybenzylidene-rhodanine (HBR) analog to the reconstituted functional PYP, or to the reconstituted functional truncated fragment thereof.

Thus, according to the present invention, the reconstitution of a functional PYP, or a functional truncated fragment thereof, can be detected through the detection of the fluorescence emitted by a fluorogenic hydroxybenzylidene-rhodanine (HBR) analog upon binding to the reconstituted functional PYP or to the reconstituted functional truncated fragment thereof.

In one embodiment, the functional PYP derives from an amino acid sequence as set forth in SEQ ID NO: 1 or from an amino acid sequence having at least about 30%, 35%, 40%, 45%, 50%, 55%, 60% or 65% identity, preferably at least about 70%, 75%, 80%, 85%, 90%, 91%, 92%, 93%, 94%, 95%, 96%, 97%, 98% or 99% or more identity with the amino acid sequence as set forth in SEQ ID NO: 1.

In one embodiment, the functional PYP derives from the PYP of bacteria species selected from the group comprising or consisting of *Halorhodospira halophila* (SEQ ID NO: 1), *Halomonas boliviensis* LC1 (SEQ ID NO: 2), *Halomonas* sp. GFAJ-1 (SEQ ID NO: 3), Rheinheimera sp. A13L (SEQ ID NO: 4), *Idiomarina loihiensis* (SEQ ID NO: 5), *Thiorhodospira sibirica* ATCC 700588 (SEQ ID NO: 6) and *Rhodothalassium salexigens* (SEQ ID NO: 7).

According to the present invention, the functional PYP comprises a cysteine at position 69 by reference to the sequence as set forth in SEQ ID NO: 1 or at the corresponding position in the sequences as set forth in SEQ ID NO: 2-7, and one or more amino acid substitutions in the amino acid region from position 94 to position 101 with reference to SEQ ID NO: 1 or in the corresponding amino acid region in the sequences as set forth in SEQ ID NO: 2-7, one of said substitutions being a proline at position 97 with reference to SEQ ID NO: 1, or at the corresponding position in the sequences as set forth in SEQ ID NO: 2-7.

In one embodiment, the functional PYP comprises or consists of an amino acid sequence as set forth in SEQ ID NO: 8, or a functional truncated fragment thereof, or an amino acid sequence having at least about 30%, 35%, 40%, 45%, 50%, 55%, 60% or 65% identity, preferably at least about 70%, 75%, 80%, 85%, 90%, 91%, 92%, 93%, 94%, 95%, 96%, 97%, 98% or 99% or more identity with the amino acid sequence as set forth in SEQ ID NO: 8 or a functional truncated fragment thereof, said amino acid sequence further comprising one or more amino acid substitutions in the amino acid region from position 94 to position 101 with reference to SEQ ID NO: 8, one of said substitution being a proline at position 97 with reference to SEQ ID NO: 8.

In one embodiment, said functional PYP further comprises at least one, at least two or at least three amino acid substitution(s) in the amino acid region from position 94 to position 101 with reference to SEQ ID NO: 8, said amino acid substitution(s) being selected from the group comprising or consisting of a tryptophan at position 94; an isoleucine, valine or leucine at position 96; and a threonine at position 98.

In one embodiment, said functional PYP further comprises the following amino acid substitutions in the amino acid region from position 94 to position 101 with reference to SEQ ID NO: 8: a tryptophan at position 94, a methionine at position 95, an isoleucine at position 96, a threonine at position 98, a serine at position 99, an arginine at position 100, and a glycine at position 101.

In one embodiment, the functional PYP comprises or consists of an amino acid sequence as set forth in SEQ ID NO: 9, or a functional truncated fragment thereof, or an amino acid sequence having at least about 30%, 35%, 40%, 45%, 50%, 55%, 60% or 65% identity, preferably at least about 70%, 75%, 80%, 85%, 90%, 91%, 92%, 93%, 94%, 95%, 96%, 97%, 98% or 99% or more identity with the amino acid sequence as set forth in SEQ ID NO: 9 or a functional truncated fragment thereof.

In one embodiment, the functional PYP comprises or consists of an amino acid sequence as set forth in any one of SEQ ID NO: 9, SEQ ID NO: 10, SEQ ID NO: 11, SEQ ID NO: 12, SEQ ID NO: 13, SEQ ID NO: 14 or SEQ ID NO: 15, or a functional truncated fragment thereof.

The amino acid sequences as set forth in any one of SEQ ID NO: 10-15 have at least 70% identity with the amino acid sequence as set forth in SEQ ID NO: 9.

In one embodiment, the functional PYP as described hereinabove further comprises at least one of the following amino acid substitutions at the positions defined with reference to SEQ ID NO: 9: an asparagine at position 19, a leucine at position 62, a cysteine or a glutamic acid at position 68, an arginine at position 71, a serine at position 73, an isoleucine at position 107, and/or an isoleucine at position 122.

In one embodiment, the functional PYP comprises or consists of an amino acid sequence as set forth in SEQ ID NO: 8, or a functional truncated fragment thereof, further comprising one of the following combination of substitutions:

Y94W, T95M, F96I, D97P, Y98T, Q99S, M100R and T101G (SEQ ID NO: 9);

Y94W, T95M, F96I, D97P, Y98T, Q99S, M100R, T101G and V107I (SEQ ID NO: 16);

Y94W, T95M, F96I, D97P, Y98T, Q99S, M100R, T101G and V122I (SEQ ID NO: 17);

Y94W, T95M, F96I, D97P, Y98T, Q99S, M100R, T101G, V107I and V122I (SEQ ID NO: 18);

F62L, P68C, D71R, P73S, Y94W, T95M, F96I, D97P, Y98T, Q99S, M100R and T101G (SEQ ID NO: 19);

D19N, F62L, P68C, D71R, P73S, Y94W, F96I, D97P, Y98T, Q99K, M100R and T101G (SEQ ID NO: 20); or F62L, P68E, C69G, D71R, P73S, Y94W, F96I, D97P, Y98T, Q99K, M100R and T101G (SEQ ID NO: 21), wherein the substitutions are defined using SEQ ID NO: 8 as a reference.

In one embodiment, the functional PYP comprises or consists of an amino acid sequence as set forth in any one of SEQ ID NO: 9, SEQ ID NO: 16, SEQ ID NO: 17, SEQ ID NO: 18, SEQ ID NO: 19, SEQ ID NO: 20 or SEQ ID NO: 21, or a functional truncated fragment thereof, or an amino acid sequence having at least about 30%, 35%, 40%, 45%, 50%, 55%, 60% or 65% identity, preferably at least about 70%, 75%, 80%, 85%, 90%, 91%, 92%, 93%, 94%, 95%, 96%, 97%, 98% or 99% or more identity with an amino acid sequence selected from the group comprising or consisting of SEQ ID NO: 9; SEQ ID NO: 16, SEQ ID NO: 17, SEQ ID NO: 18, SEQ ID NO: 19, SEQ ID NO: 20 and SEQ ID NO: 21, or a functional truncated fragment thereof.

In one embodiment, the functional PYP comprises or consists of an amino acid sequence as set forth in any one of SEQ ID NO: 9-21, or a functional truncated fragment thereof.

In one embodiment, the first PYP fragment of the invention comprises or consists of a N-terminal fragment of a functional PYP as described hereinabove ending at position 114 with reference to SEQ ID NO: 8, or a truncated fragment thereof.

In one embodiment, the first PYP fragment of the invention comprises or consists of an amino acid sequence as set forth in SEQ ID NO: 22 or a truncated fragment thereof, or an amino acid sequence having at least about 30%, 35%, 40%, 45%, 50%, 55%, 60% or 65% identity, preferably at least about 70%, 75%, 80%, 85%, 90%, 91%, 92%, 93%, 94%, 95%, 96%, 97%, 98% or 99% or more identity with the amino acid sequence as set forth in SEQ ID NO: 22, or a truncated fragment thereof, said amino acid sequence further comprising one or more amino acid substitutions in the amino acid region from position 94 to position 101 with reference to SEQ ID NO: 22, one of said substitution being a proline at position 97 with reference to SEQ ID NO: 22.

In one embodiment, said first PYP fragment of the invention, or a truncated fragment thereof, further comprises at least one, at least two or at least three amino acid substitution (s) in the amino acid region from position 94 to position 101 with reference to SEQ ID NO: 22, said amino acid substitution(s) being selected from the group comprising or consisting of a tryptophan at position 94; an isoleucine, valine or leucine at position 96; and a threonine at position 98.

In one embodiment, the first PYP fragment of the invention, or a truncated fragment thereof, as described hereinabove comprises the following amino acid substitutions in the amino acid region from position 94 to position 101 with reference to SEQ ID NO: 22: a tryptophan at position 94, a methionine at position 95, an isoleucine at position 96, a threonine at position 98, a serine at position 99, an arginine at position 100, and a glycine at position 101.

In one embodiment, the first PYP fragment of the invention comprises or consists of an amino acid sequence as set forth in SEQ ID NO: 23 (MEHVAFGSEDIENT-LAKMDDGQLDGLAFGAIQLDGDGNILQYNAAE-GDITGR DPKQVIGKNFFKDVAPGTDSPEFYGKFKEG-VASGNLNTMFEWMIPTSRGPTKV KVHMKKALS) or a truncated fragment thereof, or an amino acid sequence having at least about 30%, 35%, 40%, 45%, 50%, 55%, 60% or 65% identity, preferably at least about 70%, 75%, 80%, 85%, 90%, 91%, 92%, 93%, 94%, 95%, 96%, 97%, 98% or 99% or more identity with the amino acid sequence as set forth in SEQ ID NO: 23, or a truncated fragment thereof.

In one embodiment, the first PYP fragment of the invention thus comprises, or consists of, an amino acid sequence as set forth in any one of SEQ ID NO: 23, SEQ ID NO: 24, SEQ ID NO: 25, SEQ ID NO: 26, SEQ ID NO: 27, SEQ ID NO: 28 or SEQ ID NO: 29, or a truncated fragment thereof.

The amino acid sequences as set forth in any one of SEQ ID NO: 24-29 have at least 70% identity with the amino acid sequence as set forth in SEQ ID NO: 23.

In one embodiment, the first PYP fragment of the invention, or a truncated fragment thereof, as described hereinabove further comprises at least one of the following amino acid substitutions at the positions defined with reference to SEQ ID NO: 23: an asparagine at position 19, a leucine at position 62, a cysteine or a glutamic acid at position 68, an arginine at position 71, a serine at position 73, and/or an isoleucine at position 107.

In one embodiment, the first PYP fragment of the invention, or a truncated fragment thereof, as described hereinabove further comprises the following amino acid substitution at the position defined with reference to SEQ ID NO: 23: an isoleucine at position 107.

In one embodiment, the first PYP fragment of the invention, or a truncated fragment thereof, as described hereinabove further comprises at least one of the following amino acid substitutions at the positions defined with reference to SEQ ID NO: 23: an asparagine at position 19, a leucine at position 62, a cysteine or a glutamic acid at position 68, an arginine at position 71, and/or a serine at position 73.

In one embodiment, the first PYP fragment of the invention, or a truncated fragment thereof, as described hereinabove further comprises at least one of the following amino acid substitutions at the positions defined with reference to SEQ ID NO: 23: a leucine at position 62, an arginine at position 71, and/or a serine at position 73.

In one embodiment, the first PYP fragment of the invention comprises or consists of an amino acid sequence as set forth in SEQ ID NO: 22, or a truncated fragment thereof, further comprising at least one of the following combination of substitutions:

Y94W, T95M, F96I, D97P, Y98T, Q99S, M100R and T101G (SEQ ID NO: 23);

Y94W, T95M, F96I, D97P, Y98T, Q99S, M100R, T101G and V107I (SEQ ID NO: 30);

F62L, P68C, D71R, P73S, Y94W, T95M, F96I, D97P, Y98T, Q99S, M100R and T101G (SEQ ID NO: 31);

D19N, F62L, P68C, D71R, P73S, Y94W, F96I, D97P, Y98T, Q99K, M100R and T101G (SEQ ID NO: 32); or F62L, P68E, C69G, D71R, P73S, Y94W, F96I, D97P, Y98T, Q99K, M100R and T101G (SEQ ID NO: 33), wherein the substitutions are defined using SEQ ID NO: 22 as a reference.

In one embodiment, the first PYP fragment of the invention comprises or consists of an amino acid sequence as set forth in any one of SEQ ID NO: 23, SEQ ID NO: 30, SEQ ID NO: 31, SEQ ID NO: 32, or SEQ ID NO: 33, or a truncated fragment thereof, or an amino acid sequence having at least about 30%, 35%, 40%, 45%, 50%, 55%, 60% or 65% identity, preferably at least about 70%, 75%, 80%, 85%, 90%, 91%, 92%, 93%, 94%, 95%, 96%, 97%, 98% or 99% or more identity with an amino acid sequence selected from the group comprising or consisting of SEQ ID NO: 23, SEQ ID NO: 30, SEQ ID NO: 31, SEQ ID NO: 32, and SEQ ID NO: 33, or a truncated fragment thereof.

In one embodiment, the first PYP fragment of the invention comprises or consists of an amino acid sequence as set forth in any one of SEQ ID NO: 23-33, or a truncated fragment thereof.

In one embodiment, the truncated fragment of the first PYP fragment of the invention comprises the deletion of amino acids starting from the N-terminal end of the first PYP fragment as described hereinabove, preferably the deletion of a number of amino acids ranging from 1 amino acid to 50 amino acids, more preferably ranging from 1 amino acid to 40 amino acids, from 1 amino acid to 35 amino acids, from 1 amino acid to 30 amino acids, even more preferably from 1 amino acid to 25 amino acids.

In one embodiment, the truncated fragment of the first PYP fragment of the invention is truncated of the amino acids from position 1 to at most position 25 with reference to SEQ ID NO: 22 (or with reference to any other amino acid sequence of the same length, such as any one of SEQ ID NO: 23-33). Thus, in one embodiment, the truncated fragment of the first PYP fragment of the invention comprises at least 89 consecutive amino acids, from position 26 to position 114, of the first PYP fragment as described hereinabove.

In other words, the truncated fragment of the first PYP fragment of the invention comprises at least 89 consecutive amino acids from the C-terminal end of the first PYP fragment as described hereinabove.

In one embodiment, the truncated fragment of the first PYP fragment of the invention is truncated of 1, 2, 3, 4, 5, 6, 7, 8, 9, 10, 11, 12, 13, 14, 15, 16, 17, 18, 19, 20, 21, 22, 23, 24 or 25 amino acids from the N-terminal end (also referred to as N-ter) of the first PYP fragment as described hereinabove.

In one embodiment, the truncated fragment of the first PYP fragment of the invention comprises 89, 90, 91, 92, 93, 94, 95, 96, 97, 98, 99, 100, 101, 102, 103, 104, 105, 106, 107, 108, 109, 110, 111, 112, or 113 consecutive amino acids from the C-terminal end of the first PYP fragment as described hereinabove.

In one embodiment, the second PYP fragment of the invention comprises or consist of the C-terminal fragment of a functional PYP as described hereinabove starting at position 115 with reference to SEQ ID NO: 8, or a truncated fragment thereof.

In one embodiment, the second PYP fragment of the invention thus comprises or consists of an amino acid sequence as set forth in SEQ ID NO: 34 (GDSYWVFVKRV), or a truncated fragment thereof, or an amino acid sequence having at least about 30%, 35%, 40%, 45%, 50%, 55%, 60% or 65% identity, preferably at least about 70%, 75%, 80%, 85% or 90% or more identity with the amino acid sequence as set forth in SEQ ID NO: 34, or a truncated fragment thereof.

In one embodiment, the second PYP fragment of the invention comprises or consists of an amino acid sequence as set forth in any one of SEQ ID NO: 34, SEQ ID NO: 35, SEQ ID NO: 36, SEQ ID NO: 37, SEQ ID NO: 38, SEQ ID NO: 39, or SEQ ID NO: 40, or a truncated fragment thereof.

The amino acid sequences as set forth in any one of SEQ ID NO: 35-40 have at least about 70% identity with the amino acid sequence as set forth in SEQ ID NO: 34.

In one embodiment, the second PYP fragment of the invention, or a truncated fragment thereof, as described hereinabove further comprises the following amino acid substitution with reference to SEQ ID NO: 34: an isoleucine at position 8.

In one embodiment, the second PYP fragment of the invention comprises or consists of an amino acid sequence as set forth in SEQ ID NO: 41, or a truncated fragment thereof, or an amino acid sequence having at least about 30%, 35%, 40%, 45%, 50%, 55%, 60% or 65% identity, preferably at least about 70%, 75%, 80%, 85% or 90% or more identity with the amino acid sequence as set forth in SEQ ID NO:41, or a truncated fragment thereof.

In one embodiment, the second PYP fragment of the invention comprises or consists of an amino acid sequence as set forth in any one SEQ ID NO: 34-41, or a truncated fragment thereof.

In one embodiment, the truncated fragment of the second PYP fragment of the invention comprises at least 8 consecutive amino acids of the second PYP fragment as described hereinabove.

In one embodiment, the truncated fragment of the second PYP fragment of the invention comprises 8, 9 or 10 consecutive amino acids of the second PYP fragment as described hereinabove.

In one embodiment, the truncated fragment of the second PYP fragment of the invention comprises the deletion of amino acids starting from the N-terminal end and/or the C-terminal end of the second PYP fragment as described hereinabove, preferably the deletion of 1, 2 or 3 amino acids.

In one embodiment, the truncated fragment of the second PYP fragment of the invention comprises the deletion of amino acids starting from the N-terminal end of the second PYP fragment as described hereinabove, preferably the deletion of 1, 2 or 3 amino acids.

In one embodiment, the truncated fragment of the second PYP fragment of the invention comprises the deletion of amino acids starting from the C-terminal end of the second PYP fragment as described hereinabove, preferably the deletion of 1, 2 or 3 amino acids.

In one embodiment, the truncated fragment of the second PYP fragment of the invention comprises 8, 9 or 10 consecutive amino acids from the N-terminal end of the second PYP fragment as described hereinabove.

In one embodiment, the truncated fragment of the second PYP fragment of the invention comprises or consists of an amino acid sequence as set forth in SEQ ID NO: 42 (GDSYWVFVKR), SEQ ID NO: 43 (GDSYWVFVK) or SEQ ID NO: 44 (GDSYWVFV), or an amino acid sequence having at least about 30%, 35%, 40%, 45%, 50%, 55%, 60% or 65% identity, preferably at least about 70%, 75%, 80%, 85% or 90% or more identity with the amino acid sequence as set forth in SEQ ID NO: 42, SEQ ID NO: 43 or SEQ ID NO: 44.

According to one embodiment, the complementation system of the invention comprises a first PYP fragment as described hereinabove, or a truncated fragment thereof as described hereinabove, and a second PYP fragment as described hereinabove, or a truncated fragment thereof as described hereinabove.

In one embodiment, the complementation system of the invention comprises:
a first PYP fragment of the invention comprising or consisting of an amino acid sequence as set forth in SEQ ID NO: 23, or a truncated fragment thereof as described hereinabove, or an amino acid sequence having at least about 30%, 35%, 40%, 45%, 50%, 55%, 60% or 65% identity, preferably at least about 70%, 75%, 80%, 85%, 90%, 91%, 92%, 93%, 94%, 95%, 96%, 97%, 98% or 99% or more identity with the amino acid sequence as set forth in SEQ ID NO: 23, or a truncated fragment thereof as described hereinabove; and
a second PYP fragment of the invention comprising or consisting of an amino acid sequence as set forth in SEQ ID NO: 34, or a truncated fragment thereof, or an amino acid sequence having at least about 30%, 35%, 40%, 45%, 50%, 55%, 60% or 65% identity, preferably at least about 70%, 75%, 80%, 85% or 90% or more identity with the amino acid sequence as set forth in SEQ ID NO: 34, or a truncated fragment thereof as described hereinabove.

In said embodiment, the first and second PYP fragments, or truncated fragments thereof, are thus able to reconstitute a functional PYP comprising or consisting of an amino acid sequence as set forth in SEQ ID NO: 9, or a functional truncated fragment thereof, or an amino acid sequence having at least about 30%, 35%, 40%, 45%, 50%, 55%, 60% or 65% identity, preferably at least about 70%, 75%, 80%, 85%, 90%, 91%, 92%, 93%, 94%, 95%, 96%, 97%, 98% or 99% or more identity with the amino acid sequence SEQ ID NO: 9, or a functional truncated fragment thereof.

In one embodiment, the complementation system of the invention comprises:
a first PYP fragment of the invention comprising or consisting of an amino acid sequence as set forth in any one of SEQ ID NO: 23, SEQ ID NO: 24, SEQ ID NO: 25, SEQ ID NO: 26, SEQ ID NO: 27, SEQ ID NO: 28 or SEQ ID NO: 29, or a truncated fragment thereof as described hereinabove; and
a second PYP fragment of the invention comprising or consisting of an amino acid sequence as set forth in SEQ ID NO: 34, or a truncated fragment thereof, or an amino acid sequence having at least about 30%, 35%, 40%, 45%, 50%, 55%, 60% or 65% identity, preferably at least about 70%, 75%, 80%, 85% or 90% or more identity with the amino acid sequence as set forth in SEQ ID NO: 34, or a truncated fragment thereof as described hereinabove.

In one embodiment, the complementation system of the invention comprises:
a first PYP fragment of the invention comprising or consisting of an amino acid sequence as set forth in SEQ ID NO: 23, or a truncated fragment thereof as described hereinabove, or an amino acid sequence having at least about 30%, 35%, 40%, 45%, 50%, 55%, 60% or 65% identity, preferably at least about 70%, 75%, 80%, 85%, 90%, 91%, 92%, 93%, 94%, 95%, 96%, 97%, 98% or 99% or more identity with the amino acid sequence as set forth in SEQ ID NO: 23, or a truncated fragment thereof as described hereinabove; and
a second PYP fragment of the invention comprising or consisting of an amino acid sequence as set forth in any one of SEQ ID NO:34, SEQ ID NO: 35, SEQ ID NO: 36, SEQ ID NO: 37, SEQ ID NO: 38, SEQ ID NO: 39 or SEQ ID NO: 40, or a truncated fragment thereof as described hereinabove.

In one embodiment, the complementation system of the invention comprises:
a first PYP fragment of the invention comprising or consisting of an amino acid sequence as set forth in any one of SEQ ID NO: 23, SEQ ID NO: 24, SEQ ID NO: 25, SEQ ID NO: 26, SEQ ID NO: 27, SEQ ID NO: 28 or SEQ ID NO: 29, or a truncated fragment thereof as described hereinabove; and a second PYP fragment of the invention comprising or consisting of an amino acid sequence as set forth in any one of SEQ ID NO:34, SEQ ID NO: 35, SEQ ID NO: 36, SEQ ID NO: 37, SEQ ID NO: 38, SEQ ID NO: 39 or SEQ ID NO: 40, or a truncated fragment thereof as described hereinabove.

In one embodiment, the complementation system of the invention comprises:

a first PYP fragment of the invention comprising or consisting of an amino acid sequence as set forth in any one of SEQ ID NO: 23, SEQ ID NO: 24, SEQ ID NO: 25, SEQ ID NO: 26, SEQ ID NO: 27, SEQ ID NO: 28 or SEQ ID NO: 29, or a truncated fragment thereof as described hereinabove; and a second PYP fragment of the invention comprising or consisting of an amino acid sequence as set forth in any one of SEQ ID NO:34, SEQ ID NO: 35, SEQ ID NO: 36, SEQ ID NO: 37, SEQ ID NO: 38, SEQ ID NO: 39 or SEQ ID NO: 40, respectively, or a truncated fragment thereof as described hereinabove.

Thus, in one embodiment, the complementation system of the invention comprises:

a first PYP fragment comprising or consisting of an amino acid sequence as set forth in SEQ ID NO: 23, or a truncated fragment thereof as described hereinabove and a second PYP fragment comprising or consisting of an amino acid sequence as set forth in SEQ ID NO: 34, or a truncated fragment thereof as described hereinabove;

a first PYP fragment comprising or consisting of an amino acid sequence as set forth in SEQ ID NO: 24, or a truncated fragment thereof as described hereinabove and a second PYP fragment comprising or consisting of an amino acid sequence as set forth in SEQ ID NO: 35, or a truncated fragment thereof as described hereinabove;

a first PYP fragment comprising or consisting of an amino acid sequence as set forth in SEQ ID NO: 25, or a truncated fragment thereof as described hereinabove and a second PYP fragment comprising or consisting of an amino acid sequence as set forth in SEQ ID NO: 36, or a truncated fragment thereof as described hereinabove;

a first PYP fragment comprising or consisting of an amino acid sequence as set forth in SEQ ID NO: 26, or a truncated fragment thereof as described hereinabove and a second PYP fragment comprising or consisting of an amino acid sequence as set forth in SEQ ID NO: 37, or a truncated fragment thereof as described hereinabove;

a first PYP fragment comprising or consisting of an amino acid sequence as set forth in SEQ ID NO: 27, or a truncated fragment thereof as described hereinabove and a second PYP fragment comprising or consisting of an amino acid sequence as set forth in SEQ ID NO: 38, or a truncated fragment thereof as described hereinabove;

a first PYP fragment comprising or consisting of an amino acid sequence as set forth in SEQ ID NO: 28, or a truncated fragment thereof as described hereinabove and a second PYP fragment comprising or consisting of an amino acid sequence as set forth in SEQ ID NO: 39, or a truncated fragment thereof as described hereinabove; or a first PYP fragment comprising or consisting of an amino acid sequence as set forth in SEQ ID NO: 29, or a truncated fragment thereof as described hereinabove and a second PYP fragment comprising or consisting of an amino acid sequence as set forth in SEQ ID NO: 40, or a truncated fragment thereof as described hereinabove.

In one embodiment, the complementation system of the invention comprises:

a first PYP fragment of the invention comprising or consisting of an amino acid sequence as set forth in SEQ ID NO: 24 or a truncated fragment thereof as described hereinabove; and a second PYP fragment of the invention comprising or consisting of an amino acid sequence as set forth in SEQ ID NO: 35, or a truncated fragment thereof as described hereinabove.

In said embodiment, the first and second PYP fragments, or truncated fragments thereof, are thus able to reconstitute a functional PYP comprising or consisting of an amino acid sequence as set forth in SEQ ID NO: 10, or a functional truncated fragment thereof.

In one embodiment, the complementation system of the invention comprises:

a first PYP fragment of the invention comprising or consisting of an amino acid sequence as set forth in SEQ ID NO: 25 or a truncated fragment thereof as described hereinabove; and a second PYP fragment of the invention comprising or consisting of an amino acid sequence as set forth in SEQ ID NO: 36, or a truncated fragment thereof as described hereinabove.

In said embodiment, the first and second PYP fragments, or truncated fragments thereof, are thus able to reconstitute a functional PYP comprising or consisting of an amino acid sequence as set forth in SEQ ID NO: 11, or a functional truncated fragment thereof.

In one embodiment, the complementation system of the invention comprises:

a first PYP fragment of the invention comprising or consisting of an amino acid sequence as set forth in SEQ ID NO: 26 or a truncated fragment thereof as described hereinabove; and a second PYP fragment of the invention comprising or consisting of an amino acid sequence as set forth in SEQ ID NO: 37, or a truncated fragment thereof as described hereinabove.

In said embodiment, the first and second PYP fragments, or truncated fragments thereof, are thus able to reconstitute a functional PYP comprising or consisting of an amino acid sequence as set forth in SEQ ID NO: 12, or a functional truncated fragment thereof.

In one embodiment, the complementation system of the invention comprises:

a first PYP fragment of the invention comprising or consisting of an amino acid sequence as set forth in SEQ ID NO: 27 or a truncated fragment thereof as described hereinabove; and a second PYP fragment of the invention comprising or consisting of an amino acid sequence as set forth in SEQ ID NO: 38, or a truncated fragment thereof as described hereinabove.

In said embodiment, the first and second PYP fragments, or truncated fragments thereof, are thus able to reconstitute a functional PYP comprising or consisting of an amino acid sequence as set forth in SEQ ID NO: 13, or a functional truncated fragment thereof.

In one embodiment, the complementation system of the invention comprises:

a first PYP fragment of the invention comprising or consisting of an amino acid sequence as set forth in SEQ ID NO: 28 or a truncated fragment thereof as described hereinabove; and a second PYP fragment of the invention comprising or consisting of an amino acid sequence as set forth in SEQ ID NO: 39, or a truncated fragment thereof as described hereinabove.

In said embodiment, the first and second PYP fragments, or truncated fragments thereof, are thus able to reconstitute a functional PYP comprising or consisting of an amino acid sequence as set forth in SEQ ID NO: 14, or a functional truncated fragment thereof.

In one embodiment, the complementation system of the invention comprises:

a first PYP fragment of the invention comprising or consisting of an amino acid sequence as set forth in SEQ ID NO: 29 or a truncated fragment thereof as described hereinabove; and a second PYP fragment of the invention comprising or consisting of an amino acid sequence as set forth in SEQ ID NO: 40, or a truncated fragment thereof as described hereinabove.

In said embodiment, the first and second PYP fragments, or truncated fragments thereof, are thus able to reconstitute a functional PYP comprising or consisting of an amino acid sequence as set forth in SEQ ID NO: 15, or a functional truncated fragment thereof.

In one embodiment, the complementation system of the invention comprises:

a first PYP fragment of the invention comprising or consisting of an amino acid sequence as set forth in SEQ ID NO: 23, or a truncated fragment thereof as described hereinabove, or an amino acid sequence having at least about 70%, 75%, 80%, 85%, 90%, 91%, 92%, 93%, 94%, 95%, 96%, 97%, 98% or 99% or more identity with the amino acid sequence as set forth in SEQ ID NO: 23, or a truncated fragment thereof as described hereinabove; and a second PYP fragment of the invention comprising or consisting of an amino acid sequence as set forth in SEQ ID NO: 34, SEQ ID: 42, SEQ ID NO: 43 or SEQ ID NO: 44, or an amino acid sequence having at least about 70%, 75%, 80%, 85% or 90% or more identity with any one of the amino acid sequence as set forth in SEQ ID NO: 34, SEQ ID: 42, SEQ ID NO: 43 or SEQ ID NO: 44.

In one embodiment, the first PYP fragment, or a truncated fragment thereof, of the complementation assay of the invention as described hereinabove further comprises at least one of the following amino acid substitutions at the positions defined with reference to SEQ ID NO: 23: an asparagine at position 19, a leucine at position 62, a cysteine or a glutamic acid at position 68, an arginine at position 71, a serine at position 73, and/or an isoleucine at position 107; and/or the second PYP fragment, or a truncated fragment thereof, of the complementation assay of the invention as described hereinabove further comprises the following amino acid substitution with reference to SEQ ID NO: 34: an isoleucine at position 8.

In one embodiment, the first PYP fragment, or a truncated fragment thereof, of the complementation assay of the invention as described hereinabove further comprises at least one of the following amino acid substitutions at the positions defined with reference to SEQ ID NO: 23: an asparagine at position 19, a leucine at position 62, a cysteine or a glutamic acid at position 68, an arginine at position 71, a serine at position 73, and/or an isoleucine at position 107.

In one embodiment, the first PYP fragment, or a truncated fragment thereof, of the complementation assay of the invention as described hereinabove further comprises the following amino acid substitution at the position defined with reference to SEQ ID NO: 23: an isoleucine at position 107.

In one embodiment, the first PYP fragment, or a truncated fragment thereof, of the complementation assay of the invention as described hereinabove further comprises at least one of the following amino acid substitutions at the positions defined with reference to SEQ ID NO: 23: an asparagine at position 19, a leucine at position 62, a cysteine or a glutamic acid at position 68, an arginine at position 71, and/or a serine at position 73.

In one embodiment, the first PYP fragment, or a truncated fragment thereof, of the complementation assay of the invention as described hereinabove further comprises at least one of the following amino acid substitutions at the positions defined with reference to SEQ ID NO: 23: a leucine at position 62, an arginine at position 71, and/or a serine at position 73.

In one embodiment, the second PYP fragment, or a truncated fragment thereof, of the complementation assay of the invention as described hereinabove further comprises the following amino acid substitution with reference to SEQ ID NO: 34: an isoleucine at position 8.

In one embodiment, the complementation system of the invention comprises:

a first PYP fragment of the invention comprising or consisting of an amino acid sequence as set forth in SEQ ID NO: 30 or a truncated fragment thereof as described hereinabove; and a second PYP fragment of the invention comprising or consisting of an amino acid sequence as set forth in SEQ ID NO: 34, or a truncated fragment thereof as described hereinabove.

In said embodiment, the first and second PYP fragments, or truncated fragments thereof, are thus able to reconstitute a functional PYP comprising or consisting of an amino acid sequence as set forth in SEQ ID NO: 16, or a functional truncated fragment thereof.

According to one embodiment, the truncated fragment of the first PYP fragment of the complementation assay of the invention as described hereinabove comprises at least 89 consecutive amino acids from the C-terminal end of said first PYP fragment.

According to one embodiment, the truncated fragment of the second PYP fragment of the complementation assay of the invention as described hereinabove comprises at least 8 consecutive amino acids of said second PYP fragment, preferably at least 8 consecutive amino acids from the N-terminal end of said second PYP fragment.

As mentioned hereinabove, according to the present invention, the complementation system comprises a first PYP fragment and a second PYP fragment, or truncated fragments thereof, wherein the first and second PYP fragments, or truncated fragments thereof, are able to reconstitute a functional PYP, or a functional truncated fragment thereof, that binds a fluorogenic hydroxybenzylidene rhodanine (HBR) analog, preferably reversibly.

According to the present invention, the reconstitution of a functional PYP, or a functional truncated fragment thereof, can be obtained by coupling or fusing the two PYP fragments, or truncated fragments thereof, of the complementation system of the invention to molecules interacting together, wherein the first PYP fragment, or a truncated fragment thereof, is coupled or fused to a first molecule and the second PYP fragment, or a truncated fragment thereof, is coupled or fused to a second molecule. Through their interaction, the molecules bring the two PYP fragments, or truncated fragments thereof, of the complementation system of the invention sufficiently close to each other so that a functional PYP, or a functional truncated fragment thereof, is reconstituted.

As mentioned above, the reconstitution of a functional PYP, or a functional truncated fragment thereof, can be detected through the detection of the fluorescence emitted by a fluorogenic hydroxybenzylidene-rhodanine (HBR) analog upon binding to the reconstituted functional PYP, or to the reconstituted functional truncated fragment thereof.

Indeed, the complex subsequently formed by the functional PYP, or functional truncated fragment thereof, reconstituted from the two PYP fragments, or truncated fragments thereof, of the complementation system of the invention, and a fluorogenic HBR analog is fluorescent, i.e. can emit light upon light excitation.

According to one embodiment, the functional PYP, or functional truncated fragment thereof, reconstituted from the two PYP fragments, or truncated fragments thereof, of the complementation system of the invention binds a fluorogenic HBR analog reversibly, i.e., through non-covalent interactions. Thus, according to one embodiment, the binding of the fluorogenic HBR analog to the functional PYP, or functional truncated fragment thereof, reconstituted from the two PYP fragments, or truncated fragments thereof, of the complementation system of the invention is reversible.

Methods for assessing the binding of a fluorogenic chromophore to a polypeptide are well-known in the art. Such methods may notably rely on the assessment of the fluorescence emitted by the fluorogenic chromophore upon binding to the polypeptide and include spectrofluorimetry.

According to one embodiment, the functional PYP, or functional truncated fragment thereof, reconstituted from the two PYP fragments, or truncated fragments thereof, of the complementation system of the invention binds reversibly a fluorogenic HBR analog with:

- a $K_D$ ranging from about 0.01 to about 20 µM when measured at a temperature of about 25° C., preferably ranging from about 0.05 to about 10 µM, more preferably ranging from about 0.1 to about 5 µM; and/or
- a $k_{off}$ ranging from about 0.5 to about 50 s$^{-1}$ when measured at a temperature of about 25° C., preferably from about 1 to about 25 s$^{-1}$, more preferably from about 5 to about 20 s$^{-1}$; and/or
- a $k_{on}$ ranging from about 0.05×10$^7$ to about 50×10$^7$ M$^{-1}$s$^{-1}$ when measured at a temperature of about 25° C., preferably from about 0.1×10$^7$ to about 25×10$^7$ M$^{-1}$s$^{-1}$, more preferably from about 1×10$^7$ to about 15×10$^7$ M$^{-1}$s$^{-1}$.

Methods for measuring the $K_D$, $k_{on}$ and $k_{off}$ constants are well-known in the art, and include, for example, those described by Scatchard et al. (Ann. N.Y. Acad. Sci. USA 51:660 (1949)). In particular, methods for measuring the thermodynamic dissociation constant $K_D$ are well-known in the art, and include, for example, those described by Plamont, et al. (Plamont et al., *P Natl Acad Sci Usa* 2016, 113 (3), 497-502).

According to one embodiment, the molar absorption coefficient (ε) of a fluorogenic HBR analog bound to the functional PYP, or functional truncated fragment thereof, reconstituted from the two PYP fragments, or truncated fragments thereof, of the complementation system of the invention ranges from about 1 to about 100 mM$^{-1}$ cm$^{-1}$ when measured at its wavelength of maximal absorption ($\lambda_{abs}$). In one embodiment, the molar absorption coefficient (ε) ranges from about 10 to about 200 mM$^{-1}$ cm$^{-1}$ at $\lambda_{abs}$. In a particular embodiment, the molar absorption coefficient (ε) ranges from about 20 to about 100 mM$^{-1}$ cm$^{-1}$ at $\lambda_{abs}$.

Methods for measuring the molar absorption coefficient (ε) are known in the art, and include, for example, those described by Plamont, M.-A. et al. (Plamont, M.-A. et al., *P Natl Acad Sci Usa* 2016, 113 (3), 497-502).

According to one embodiment, the fluorescence quantum yield (ɸ) of a fluorogenic HBR analog bound to the functional PYP, or functional truncated fragment thereof, reconstituted from the two PYP fragments, or truncated fragments thereof, of the complementation system of the invention is greater than about 0.1% when measured at its wavelength of maximal absorption ($\lambda_{abs}$). In an embodiment, ɸ is greater than about 0.25%, about 0.75%, or about 1% at $\lambda_{abs}$. In a particular embodiment, ɸ is greater than about 2% at $\lambda_{abs}$.

Methods for measuring the fluorescence quantum yield (ɸ) are known in the art, and include, for example, those described by Plamont, M.-A. et al. (Plamont, M.-A. et al., *P Natl Acad Sci Usa* 2016, 113 (3), 497-502). In one embodiment, the fluorescence quantum yields after one-photon excitation ɸ are calculated from the relation:

$$\phi = \phi_{ref} \frac{1 - 10^{-A_{ref}(\lambda_{exc})}}{1 - 10^{-A(\lambda_{exc})}} \frac{D}{D_{ref}} \left(\frac{n}{n_{ref}}\right)^2$$

where the subscript ref stands for standard samples. $A(\lambda_{exc})$ is the absorbance at the excitation wavelength $\lambda_{exc}$, D is the integrated emission spectrum, and n is the refractive index for the solvent.

According to one embodiment, upon binding to a fluorogenic HBR analog, the functional PYP, or functional truncated fragment thereof, reconstituted from the two PYP fragments, or truncated fragments thereof, of the complementation system of the invention enhances the brightness of said fluorogenic HBR analog.

According to one embodiment, the brightness of a fluorogenic HBR analog bound to the functional PYP, or functional truncated fragment thereof, reconstituted from the two PYP fragments, or truncated fragments thereof, of the complementation system of the invention is greater than about 50. In an embodiment, the brightness is greater than about 200. In a particular embodiment, the brightness is greater than about 1000.

Methods for measuring the brightness are well-known in the art. Brightness corresponds to the fluorescence output per emitter and is the product of the molar absorption coefficient (at the excitation wavelength) and the fluorescence quantum yield.

According to one embodiment, the first and second PYP fragments as described hereinabove, or truncated fragments thereof as described hereinabove, are able to reconstitute a functional PYP, or a functional truncated fragment thereof, with low affinity.

Thus, in one embodiment, the first and second PYP fragments as described hereinabove, or truncated fragments thereof as described hereinabove, display a low unspecific fluorescence background in presence of a fluorogenic HBR analog due to a low self-assembly of said first and second PYP fragments, or truncated fragments thereof.

In one embodiment, the first and second PYP fragments of the invention, or truncated fragments thereof, bind each other with a dissociation constant ($K_D$) higher than about 0.1 µM, preferably higher than about 0.2 µM, more preferably higher than about 0.5 µM, even more preferably higher than 1 µM, wherein said $K_D$ is measured at a temperature of about 25° C. in presence of a fluorogenic HBR analog, preferably in presence of 10 µM of a fluorogenic HBR analog.

In one embodiment, the first and second PYP fragments of the invention, or truncated fragments thereof, bind each other with a dissociation constant ($K_D$) higher than about 0.2 µM, preferably higher than about 0.5 µM, more preferably higher than about 1 µM, even more preferably higher than 5 µM, wherein said $K_D$ is measured at a temperature of about 25° C. in presence of a fluorogenic HBR analog, preferably in presence of 10 µM of a fluorogenic HBR analog.

In one embodiment, the first and second PYP fragments of the invention, or truncated fragments thereof, bind each other with a dissociation constant ($K_D$) higher than about 0.2 µM, preferably higher than about 0.75 µM, more preferably higher than about 1 µM, even more preferably higher than about 5 µM, wherein said $K_D$ is measured at a temperature of about 25° C. in presence of HMBR, preferably in the presence of 10 µM HMBR.

In one embodiment, the first and second PYP fragments of the invention, or truncated fragments thereof, bind each other with a dissociation constant ($K_D$) higher than about 1 µM, preferably higher than about 2 µM, more preferably higher than about 5 µM, even more preferably higher than about 10 µM, wherein said $K_D$ is measured at a temperature of about 25° C. in presence of HBR-3,5-DOM, preferably in presence of 10 µM HBR-3,5-DOM.

As indicated above, methods for measuring the thermodynamic dissociation constant $K_D$ are well-known in the art, and include, for example, those described by Plamont, M.-A. et al., (Plamont, M.-A. et al., *P Natl Acad Sci Usa* 2016, 113 (3), 497-502).

In one embodiment, the thermodynamic dissociation constant $K_D$ is determined by spectrofluorometric titration as described in the Examples.

The complementation system of the invention may thus be used to study the interaction between two molecules, and in particular to study either or both of the association and the dissociation of said molecules.

The present invention also relates to a biological molecule of interest comprising the first or second PYP fragment as described hereinabove, or a truncated fragment thereof as described hereinabove. According to one embodiment, a biological molecule of interest comprising the first or second PYP fragment, or a truncated fragment thereof, is a biological molecule of interest to which the first or second PYP fragment, or a truncated fragment thereof, is attached, either covalently or non-covalently.

As used herein, the term "biological molecule of interest" encompasses any molecules present inside a living organism. In particular, the term includes, but is not limited to, amino acids, monosaccharides, nucleotides, polypeptides, proteins, polysaccharides, nucleic acids, lipids, fatty acids, glycolipids, sterols, vitamins, hormones, neurotransmitters, and metabolites.

Methods for non-covalently attaching a peptide or polypeptide to a biological molecule of interest are well-known. Methods for covalently attaching a peptide or polypeptide to a biological molecule of interest are well-known.

The present invention also relates to a pair of biological molecules of interest comprising the first and second PYP fragments as described hereinabove, or truncated fragments thereof as described hereinabove, wherein one biological molecule of interest comprises the first PYP fragment as described hereinabove, or a truncated fragment thereof as described hereinabove, and the other biological molecule of interest comprises the second PYP fragment as described hereinabove, or a truncated fragment thereof as described hereinabove.

According to one embodiment, the biological molecule of interest is a protein.

The present invention thus also relates to a fusion protein comprising the first or second PYP fragment as described hereinabove, or a truncated fragment thereof as described hereinabove.

Indeed, the PYP fragments as described hereinabove, or truncated fragments thereof as described hereinabove, can be expressed in fusion with any protein of interest within a host cell by inserting (for example via transformation or transfection) a nucleic acid sequence which encodes the resulting fusion protein.

Methods for fusing a peptide or polypeptide to a protein of interest are well-known. Briefly, such methods comprise inserting the nucleic acid sequence encoding a protein of interest in frame with the nucleic sequence encoding the peptide(s) or polypeptide(s). The nucleic sequence encoding the protein of interest can be inserted so that the encoded peptide is situated at the N-terminal end of the protein of interest or at the C-terminal end of the protein of interest, or internally, as desired. Additionally, a short nucleic sequence encoding a linker or spacer may be present between the sequences coding for the peptide and the protein of interest.

In one embodiment, the fusion protein of the invention comprises the first PYP fragment as described hereinabove, or a truncated fragment thereof as described hereinabove, and a protein of interest. In one embodiment, the fusion protein of the invention comprises the second PYP fragment as described hereinabove, or a truncated fragment thereof as described hereinabove, and a protein of interest.

In one embodiment, the fusion protein of the invention comprises at least one additional element other than the PYP fragments of the invention, or truncated fragments thereof, and the protein of interest.

Example of additional elements that may be considered for the fusion proteins of the invention include, but are not limited to, linkers, targeting signals, protease target sites, antibody crystallizable region (Fc), enzymes (such as the alkaline phosphatase or horseradish peroxidase), hemagglutinin tag, poly arginine tag, poly histidine tag, myc tag, strep tag, S-tag, HAT tag, 3× flag tag, calmodulin-binding peptide tag, SBP tag, chitin binding domain tag, GST tag, maltose-binding protein tag, fluorescent protein tag, preferably the fluorescence of which may be spectrally separated from the fluorescence associated with the complementation system of the invention, T7 tag, V5 tag, and X-press tag.

In one embodiment, the fusion protein as described hereinabove comprises a linker.

Methods for designing or selecting a linker are well-known to one skilled in the art.

Examples of linkers include, without being limited to, linkers comprising or consisting of the amino acid sequence as set forth in SEQ ID NO: 45.

The present invention also relates to a pair of fusion proteins comprising the first and second PYP fragments as described hereinabove, or truncated fragments thereof as described hereinabove, wherein one fusion protein comprises the first PYP fragment as described hereinabove, or a truncated fragment thereof as described hereinabove, and the other fusion protein comprises the second PYP fragment as described hereinabove, or a truncated fragment thereof as described hereinabove.

In one embodiment, both fusion proteins of the pair comprise the same protein of interest. In other words, in one embodiment, one fusion protein comprises the first PYP fragment as described hereinabove, or a truncated fragment thereof as described hereinabove, and a protein of interest, and the other fusion protein comprises the second PYP fragment as described hereinabove, or a truncated fragment thereof as described hereinabove, and the same protein of interest.

In one embodiment, each fusion protein of the pair comprises a distinct protein of interest. In other words, in one embodiment, one fusion protein comprises the first PYP fragment as described hereinabove, or a truncated fragment thereof as described hereinabove, and a first protein of interest, and the other fusion protein comprises the second PYP fragment as described hereinabove, or a truncated fragment thereof as described hereinabove, and a second, different, protein of interest.

In one embodiment, the first and the second proteins of interest are two reporter proteins able to interact with each other.

The present invention also relates to a nucleic acid sequence encoding the first PYP fragment and/or the second PYP fragment as described hereinabove, or truncated fragments thereof as described hereinabove, and to a nucleic acid sequence encoding the fusion protein of the invention as described hereinabove.

According to the present invention, the nucleic acid sequence of the invention encoding the first PYP fragment and/or the second PYP fragment as described hereinabove, or truncated fragments thereof as described hereinabove, includes all nucleic acid sequences that are degenerate versions of each other and that encode the same first PYP fragment and/or second PYP fragment, or truncated fragments thereof.

One skilled in the art is familiar with methods for adapting a coding sequence on the basis of the genetic code, for instance and without limitation, methods making use of codon degeneracy to introduce silent mutations and methods taking into account codon usage bias and variation of the standard genetic code relevant to the host cell considered.

According to one embodiment, the nucleic acid sequence of the invention encodes a first PYP fragment comprising or consisting of an amino acid sequence as set forth in SEQ ID NO: 23 or a truncated fragment thereof as described hereinabove, or encodes an amino acid sequence having at least about 30%, 35%, 40%, 45%, 50%, 55%, 60% or 65% identity, preferably at least about 70%, 75%, 80%, 85%, 90%, 91%, 92%, 93%, 94%, 95%, 96%, 97%, 98% or 99% or more identity with the amino acid sequence as set forth in SEQ ID NO: 23, or a truncated fragment thereof as described hereinabove.

Examples of nucleic acid sequences encoding a first PYP fragment comprising or consisting of an amino acid sequence as set forth in SEQ ID NO: 23 or an amino acid sequence having at least about 70% identity with the amino acid sequence as set forth in SEQ ID NO: 23 include, without being limited to, the nucleic acid sequences as set forth in SEQ ID NO: 46, SEQ ID NO: 47, SEQ ID NO: 48, SEQ ID NO: 49, SEQ ID NO: 50, SEQ ID NO: 51 and SEQ ID NO: 52.

An example of a nucleic acid sequence encoding a first PYP fragment comprising or consisting of an amino acid sequence as set forth in SEQ ID NO: 23 includes, without being limited to, the nucleic acid sequence as set forth in SEQ ID NO: 46.

Examples of nucleic acid sequences encoding an amino acid sequence having at least about 70% identity with the amino acid sequence as set forth in SEQ ID NO: 23 include, without being limited to, the nucleic acid sequences as set forth in SEQ ID NO: 47, SEQ ID NO: 48, SEQ ID NO: 49, SEQ ID NO: 50, SEQ ID NO: 51 and SEQ ID NO: 52.

According to one embodiment, the nucleic acid sequence of the invention encodes a second PYP fragment comprising or consisting an amino acid sequence as set forth in SEQ ID NO: 34, or encodes a truncated fragment thereof as described hereinabove, or an amino acid sequence having at least about 30%, 35%, 40%, 45%, 50%, 55%, 60% or 65% identity, preferably at least about 70%, 75%, 80%, 85% or 90% or more identity with the amino acid sequence as set forth in SEQ ID NO: 34, or a truncated fragment thereof as described hereinabove.

Examples of nucleic acid sequences encoding a second PYP fragment comprising or consisting of an amino acid sequence as set forth in SEQ ID NO: 34 or an amino acid sequence having at least about 70% identity with the amino acid sequence as set forth in SEQ ID NO: 34 include, without being limited to, the nucleic acid sequences as set forth in SEQ ID NO: 53, SEQ ID NO: 54, SEQ ID NO: 55, SEQ ID NO: 56, SEQ ID NO: 57, SEQ ID NO: 58 and SEQ ID NO: 59.

An example of a nucleic acid sequence encoding a second PYP fragment comprising or consisting of an amino acid sequence as set forth in SEQ ID NO: 34 includes, without being limited to, the nucleic acid sequence as set forth in SEQ ID NO: 53.

Examples of nucleic acid sequences encoding an amino acid sequence having at least about 70% identity with the amino acid sequence as set forth in SEQ ID NO: 34 include, without being limited to, the nucleic acid sequences as set forth in SEQ ID NO: 54, SEQ ID NO: 55, SEQ ID NO: 56, SEQ ID NO: 57, SEQ ID NO: 58 and SEQ ID NO: 59.

In one embodiment, the nucleic acid sequence of the invention encodes a second PYP fragment comprising or consisting an amino acid sequence as set forth in SEQ ID NO: 34, SEQ ID NO: 42, SEQ ID NO: 43 or SEQ ID NO: 44, or encodes an amino acid sequence having at least about 30%, 35%, 40%, 45%, 50%, 55%, 60% or 65% identity, preferably at least about 70%, 75%, 80%, 85% or 90% or more identity with the amino acid sequence as set forth in SEQ ID NO: 34, SEQ ID NO: 42, SEQ ID NO: 43 or SEQ ID NO: 44.

Examples of nucleic acid sequences encoding a second PYP fragment comprising or consisting an amino acid sequence as set forth in SEQ ID NO: 34, SEQ ID NO: 42, SEQ ID NO: 43 or SEQ ID NO: 44, include, without being limited to, the nucleic acid sequences as set forth in SEQ ID NO: 53, SEQ ID NO: 60, SEQ ID NO: 61 and SEQ ID NO: 62, respectively.

The present invention also relates to a pair of nucleic acid sequences encoding the first PYP fragment and the second PYP fragment as described hereinabove, or truncated fragments thereof as described hereinabove, wherein one nucleic acid sequence encodes the first PYP fragment as described hereinabove, or a truncated fragment thereof as described hereinabove, and the other nucleic acid sequence encodes the second PYP fragment as described hereinabove, or a truncated fragment thereof as described hereinabove.

The present invention also relates to a pair of nucleic acid sequences encoding a first fusion protein and a second fusion protein as described hereinabove, wherein one fusion protein comprises the first PYP fragment as described hereinabove, or a truncated fragment thereof as described hereinabove, and the second fusion protein comprises the second PYP fragment as described hereinabove, or a truncated fragment thereof as described hereinabove.

The present invention also relates to a vector comprising at least one nucleic acid sequence as described hereinabove.

According to one embodiment, the vector of the invention comprises:

a first nucleic acid sequence encoding the first PYP fragment, or a truncated fragment thereof, as described hereinabove; and a second nucleic acid sequence encoding the second PYP fragment, or a truncated fragment thereof, as described hereinabove.

In one embodiment, the vector of the invention comprises:

a first nucleic acid sequence encoding a first PYP fragment comprising or consisting of an amino acid sequence as set forth in SEQ ID NO: 23 or a truncated fragment thereof as described hereinabove, or an amino acid sequence having at least about 30%, 35%, 40%, 45%, 50%, 55%, 60% or 65% identity, preferably at least about 70%, 75%, 80%, 85%, 90%, 91%, 92%, 93%, 94%, 95%, 96%, 97%, 98% or 99% or more identity with the amino acid sequence as set forth in SEQ ID NO: 23, or a truncated fragment thereof as described hereinabove; and a second nucleic acid sequence encoding a second PYP fragment comprising or consisting an amino acid sequence as set forth in SEQ ID NO: 34, or a truncated fragment thereof as described hereinabove, or an amino acid sequence having at least about 30%, 35%, 40%, 45%, 50%, 55%, 60% or 65% identity, preferably at least about 70%, 75%, 80%, 85% or 90% or more identity with the amino acid sequence as set forth in SEQ ID NO: 34, or a truncated fragment thereof as described hereinabove.

In one embodiment, the vector of the invention comprises:

a first nucleic acid sequence encoding a first PYP fragment comprising or consisting of an amino acid sequence as set forth in SEQ ID NO: 23 or a truncated fragment thereof as described hereinabove, or an amino acid sequence having at least about 30%, 35%, 40%, 45%, 50%, 55%, 60% or 65% identity, preferably at least about 70%, 75%, 80%, 85%, 90%, 91%, 92%, 93%, 94%, 95%, 96%, 97%, 98% or 99% or more identity with the amino acid sequence as set forth in SEQ ID NO: 23, or a truncated fragment thereof as described hereinabove; and a second nucleic acid sequence encoding a second PYP fragment comprising or consisting an amino acid sequence as set forth in SEQ ID NO: 34, SEQ ID NO: 42, SEQ ID NO: 43 or SEQ ID NO: 44, or an amino acid sequence having at least about 30%, 35%, 40%, 45%, 50%, 55%, 60% or 65% identity, preferably at least about 70%, 75%, 80%, 85% or 90% or more identity with the amino acid sequence as set forth in SEQ ID NO: 34, SEQ ID NO: 42, SEQ ID NO: 43 or SEQ ID NO: 44.

The present invention also relates to a pair of vectors comprising the nucleic acid sequences encoding the first PYP fragment and the second PYP fragment as described hereinabove, or truncated fragments thereof as described hereinabove, wherein one vector comprises a nucleic acid sequence encoding the first PYP fragment as described hereinabove, or a truncated fragment thereof as described hereinabove, and the other vector comprises a nucleic acid sequence encoding the second PYP fragment as described hereinabove, or a truncated fragment thereof as described hereinabove.

In one embodiment, the first vector comprises a nucleic acid sequence encoding a first PYP fragment comprising or consisting of an amino acid sequence as set forth in SEQ ID NO: 23 or a truncated fragment thereof as described hereinabove, or an amino acid sequence having at least about 30%, 35%, 40%, 45%, 50%, 55%, 60% or 65% identity, preferably at least about 70%, 75%, 80%, 85%, 90%, 91%, 92%, 93%, 94%, 95%, 96%, 97%, 98% or 99% or more identity with the amino acid sequence as set forth in SEQ ID NO: 23, or a truncated fragment thereof as described hereinabove.

In one embodiment, the second vector comprises a nucleic acid sequence encoding a second PYP fragment comprising or consisting of an amino acid sequence as set forth in SEQ ID NO: 34, or a truncated fragment thereof as described hereinabove, or an amino acid sequence having at least about 30%, 35%, 40%, 45%, 50%, 55%, 60% or 65% identity, preferably at least about 70%, 75%, 80%, 85% or 90% or more identity with the amino acid sequence as set forth in SEQ ID NO: 34, or a truncated fragment thereof as described hereinabove. In one embodiment, the second vector comprises a nucleic acid sequence encoding a second PYP fragment comprising or consisting of an amino acid sequence as set forth in SEQ ID NO: 34, SEQ ID NO: 42, SEQ ID NO: 43 or SEQ ID NO: 44, or an amino acid sequence having at least about 30%, 35%, 40%, 45%, 50%, 55%, 60% or 65% identity, preferably at least about 70%, 75%, 80%, 85% or 90% or more identity with the amino acid sequence as set forth in SEQ ID NO: 34, SEQ ID NO: 42, SEQ ID NO: 43 or SEQ ID NO: 44.

As used herein the term "vector" refers to nucleic acid molecules used in molecular cloning as a vehicle to artificially carry foreign genetic material into a cell where it can be replicated and/or expressed. Examples of vectors include, without being limited to, plasmids, viral vectors and artificial chromosomes.

In particular, in the context of the present invention, the vector may comprise the required nucleic acid sequences for the fusion of the sequence encoding a protein of interest in frame with a sequence encoding a PYP fragment as described hereinabove, or a truncated fragment thereof as described hereinabove.

The present invention also relates to a cell expressing at least one of the PYP fragment as described hereinabove, or a truncated fragment thereof as described hereinabove, or a fusion protein as described hereinabove.

According to one embodiment, the cell of the invention expresses both the first and second PYP fragments as described hereinabove, or truncated fragments thereof as described hereinabove.

In one embodiment, the cell of the invention expresses a first biological molecule as described hereinabove comprising the first PYP fragment as described hereinabove, or a truncated fragment thereof as described hereinabove, and a second biological molecule as described hereinabove comprising the second PYP fragment as described hereinabove, or a truncated fragment thereof as described hereinabove.

In one embodiment, one of the biological molecules of interest is a protein. In one embodiment, both of the biological molecules of interest are a protein.

Thus, in one embodiment, the cell of the invention expresses a first fusion protein comprising the first PYP fragment as described hereinabove, or a truncated fragment thereof as described hereinabove, and a second fusion protein comprising the second PYP fragment as described hereinabove, or a truncated fragment thereof as described hereinabove.

In one embodiment, the fusion protein comprises a reporter protein.

Thus, in one embodiment, the cell of the invention expresses:
- a first fusion protein comprising the first PYP fragment as described hereinabove, or a truncated fragment thereof as described hereinabove, and a reporter protein; and
- a second fusion protein comprising the second PYP fragment as described hereinabove, or a truncated fragment thereof as described hereinabove, and a reporter protein;

wherein the reporter proteins are identical or different.

In one embodiment, the cell of the invention expresses:
- a first fusion protein comprising the first PYP fragment as described hereinabove, or a truncated fragment thereof as described hereinabove, and a reporter protein; and
- a second fusion protein comprising the second PYP fragment as described hereinabove, or a truncated fragment thereof as described hereinabove, and a reporter protein;

wherein the reporter proteins are identical or different, and wherein their interaction may be detected, localized or quantified as a way to indirectly assess a target of interest or a mechanism of interest.

Thus, in one embodiment, the cell of the invention may be used as a cellular sensor to assess a target of interest or a physiological mechanism of interest.

Examples of targets or mechanisms of interest include, without being limited to, assessment of the presence in the cell of an analyte such as calcium, and assessment of a physiological mechanism such as apoptosis.

Thus, the cell of the invention may be used as a cellular sensor to assess the presence in the cell of an analyte of interest such as calcium. The cell of the invention may be used as a cellular sensor to assess a physiological mechanism in the cell such as apoptosis. The cell of the invention may also be used as a cellular sensor to screen chemical libraries for identifying drugs regulating the target or mechanism of interest.

According to one embodiment, the complementation system as described hereinabove further comprises a fluorogenic HBR analog.

In one embodiment, the complementation system of the invention further comprises a fluorogenic HBR analog of formula (I):

formula (I)

wherein:
- R1, R2, R5 and R6 may be identical or different and each represents H, halo, hydroxyl, aryl, alkyl, cycloalkyl, heteroalkyl (e.g., alkoxy) or heterocycloalkyl group, saturated or unsaturated, linear or branched, optionally substituted by at least one group selected from halo, hydroxyl, oxo, nitro, amido, carboxy, amino, cyano, haloalkoxy, haloalkyl;
- R3 represents a non-binding doublet (i.e., a free pair of electrons) or H, halo, hydroxyl, aryl, alkyl, cycloalkyl, heteroalkyl or heterocycloalkyl group, saturated or unsaturated, linear or branched, optionally substituted by at least one group selected from halo, hydroxyl, oxo, nitro, amido, carboxy, amino, cyano, haloalkoxy, haloalkyl;
- R4 is a single or a double bound, interrupted or terminated by S, O or N atom, optionally substituted by at least one group selected from H, hydroxyl, aryl, alkyl, cycloalkyl, heteroalkyl or heterocycloalkyl group, saturated or unsaturated, linear or branched, optionally substituted by at least one group selected from halo, hydroxyl, oxo, nitro, amido, carboxy, amino, cyano, haloalkoxy, haloalkyl;
- X is OH, SH, NHR7, or N(R7)2, wherein R7 is H, halo, hydroxyl, aryl, alkyl, cycloalkyl, heteroalkyl or heterocycloalkyl group, saturated or unsaturated, linear or branched, optionally substituted by at least one group selected from halo, hydroxyl, oxo, nitro, amido, carboxy, amino, cyano, haloalkoxy, haloalkyl; and
- Y is O, NH or S.

In one embodiment, the fluorogenic HBR analog is selected from the group comprising or consisting of: (Z)-5-(4-hydroxybenzylidene)-2-thioxo-1,3-thiazolidin-4-one (HBR); (Z)-5-(4-hydroxy-3-methylbenzylidene)-2-thioxo-1,3-thiazolidin-4-one (HMBR); (Z)-5-(4-Hydroxy-3,5-dimethoxybenzylidene)-2-thioxothiazolidin-4-one (HBR-3,5DOM); (Z)-5-(4-Hydroxy-3-methoxybenzylidene)-2-thioxo-1,3-thiazolidin-4-one (HBR-30M); (Z)-5-(4-Hydroxy-3,5-dimethylbenzylidene)-2-thioxothiazolidin-4-one (HBR-3,5DM); (Z)-5-(4-Hydroxy-2,5-dimethylbenzylidene)-2-thioxo-1,3-thiazolidin-4-one (HBR-2,5DM); (Z)-5-(3-Ethyl-4-hydroxybenzylidene)-2-thioxothiazolidin-4-one (HBR-3E); (Z)-5-(3-Ethoxy-4-hydroxybenzylidene)-2-thioxothiazolidin-4-one (HBR-30E); (Z)-5-(4-hydroxybenzylidene)-3-methyl-2-thioxothiazolidin-4-one (HBMR); (Z)-5-(2,4-Dihydroxybenzylidene)-2-thioxo-1,3-thiazolidin-4-one (DHBR) (Z)-5-(4-hydroxy-3-methoxybenzylidene)-2-thioxo-1,3-thiazolidin-4-one (HMOBR); (Z)-2-(5-(3-ethyl-4-hydroxybenzylidene)-4-oxo-2-thioxothiazolidin-3-yl)acetic acid (HBRAA-3E); (Z)-2-(5-(4-hydroxy-3-ethoxybenzylidene)-4-oxo-2-thioxothiazolidin-3-yl)acetic acid (HBRAA-30E); (Z)-2-(5-(4-hydroxy-2-methoxybenzylidene)-4-oxo-2-thioxothiazolidin-3-yl)acetic acid (HBRAA-20M); (Z)-2-(5-(4-hydroxybenzylidene)-4-oxo-2-thioxothiazolidin-3-yl) acetic acid (HBRAA); (Z)-2-(5-(4-hydroxy-3-methylbenzylidene)-4-oxo-2-thioxothiazolidin-3-yl)acetic acid (HBRAA-3M); (Z)-2-(5-(4-hydroxy-3-methoxybenzylidene)-4-oxo-2-thioxothiazolidin-3-yl)acetic acid (HBRAA-30M); (Z)-2-(5-(4-hydroxy-2-methoxybenzylidene)-4-oxo-2-thioxothiazolidin-3-yl)acetic acid (HBRAA-20M); (Z)-2-(5-(4-hydroxy-2, 5-dimethylbenzylidene)-4-oxo-2-thioxothiazolidin-3-yl) acetic acid (HBRAA-2,5DM); (Z)-2-(5-(4-hydroxy-3, 5-dimethylbenzylidene)-4-oxo-2-thioxothiazolidin-3-yl)acetic acid (HBRAA-3,5DM) and (Z)-2-(5-(4-hydroxy-3, 5-dimethoxybenzylidene)-4-oxo-2-thioxothiazolidin-3-yl) acetic acid (HBRAA-3,5DOM).

In one embodiment, the fluorogenic HBR analog is selected from the group comprising or consisting of: (Z)-5-(4-hydroxy-3-methylbenzylidene)-2-thioxo-1,3-thiazolidin-4-one (HMBR); (Z)-5-(4-Hydroxy-3,5-dimethoxybenzylidene)-2-thioxothiazolidin-4-one (HBR-3,5DOM); (Z)-5-(4-Hydroxy-3-methoxybenzylidene)-2-thioxo-1,3-thiazolidin-4-one (HBR-30M) and (Z)-5-(4-Hydroxy-3,5-dimethylbenzylidene)-2-thioxothiazolidin-4-one (HBR-3,5DM).

In one embodiment the fluorogenic HBR analog is membrane-permeant.

As used herein, the term "membrane-permeant" refers to a property of a compound which is able to cross a biological membrane (i.e., a membrane consisting of a polar lipid layer, preferably a polar lipid bilayer). The term "membrane-impermeant" refers, in opposition, to a compound which is not able to cross a biological membrane.

In one embodiment, the fluorogenic HBR analog is membrane-permeant and is selected from the group comprising or consisting of: (Z)-5-(4-hydroxybenzylidene)-2-thioxo-1,3-thiazolidin-4-one (HBR); (Z)-5-(4-hydroxy-3-methylbenzylidene)-2-thioxo-1,3-thiazolidin-4-one (HMBR); (Z)-5-(4-Hydroxy-3,5-dimethoxybenzylidene)-2-thioxothiazolidin-4-one (HBR-3,5DOM); (Z)-5-(4-Hydroxy-3-methoxybenzylidene)-2-thioxo-1,3-thiazolidin-4-one (HBR-30M); (Z)-5-(4-Hydroxy-3,5-dimethylbenzylidene)-2-thioxothiazolidin-4-one (HBR-3,5DM); (Z)-5-(4-Hydroxy-2,5-dimethylbenzylidene)-2-thioxo-1,3-thiazolidin-4-one (HBR-2,5DM); (Z)-5-(3-Ethyl-4-hydroxybenzylidene)-2-thioxothiazolidin-4-one (HBR-3E); (Z)-5-(3-Ethoxy-4-hydroxybenzylidene)-2-thioxothiazolidin-4-one (HBR-30E); (Z)-5-(4-hydroxybenzylidene)-3-methyl-2-thioxothiazolidin-4-one (HBMR); (Z)-2-(5-(4-hydroxybenzylidene)-4-oxo-2-thioxothiazolidin-3-yl)acetic acid (HBAAR); (Z)-5-(2,4-Dihydroxybenzylidene)-2-thioxo-1,3-thiazolidin-4-one (DHBR) and (Z)-5-(4-hydroxy-3-methoxybenzylidene)-2-thioxo-1,3-thiazolidin-4-one (HMOBR).

In one embodiment, the fluorogenic HBR analog is membrane-permeant and selected from the group comprising or consisting of: (Z)-5-(4-hydroxy-3-methylbenzylidene)-2-thioxo-1,3-thiazolidin-4-one (HMBR); (Z)-5-(4-Hydroxy-3,5-dimethoxybenzylidene)-2-thioxothiazolidin-4-one (HBR-3,5DOM); (Z)-5-(4-Hydroxy-3-methoxybenzylidene)-2-thioxo-1,3-thiazolidin-4-one (HBR-30M) and (Z)-5-(4-Hydroxy-3,5-dimethylbenzylidene)-2-thioxothiazolidin-4-one (HBR-3,5DM).

In one embodiment the fluorogenic HBR analog is membrane-impermeant.

In one embodiment, the fluorogenic HBR analog is membrane-impermeant and selected from the group comprising or consisting of: (Z)-2-(5-(3-ethyl-4-hydroxybenzylidene)-4-oxo-2-thioxothiazolidin-3-yl)acetic acid (HBRAA-3E); (Z)-2-(5-(4-hydroxy-3-ethoxybenzylidene)-4-oxo-2-thioxothiazolidin-3-yl)acetic acid (HBRAA-30E); (Z)-2-(5-(4-hydroxy-2-methoxybenzylidene)-4-oxo-2-thioxothiazolidin-3-yl)acetic acid (HBRAA-20M); (Z)-2-(5-(4-hydroxybenzylidene)-4-oxo-2-thioxothiazolidin-3-yl)acetic acid (HBRAA); (Z)-2-(5-(4-hydroxy-3-methylbenzylidene)-4-oxo-2-thioxothiazolidin-3-yl)acetic acid (HBRAA-3M); (Z)-2-(5-(4-hydroxy-3-methoxybenzylidene)-4-oxo-2-thioxothiazolidin-3-yl)acetic acid (HBRAA-30M); (Z)-2-(5-(4-hydroxy-2-methoxybenzylidene)-4-oxo-2-thioxothiazolidin-3-yl)acetic acid (HBRAA-20M); (Z)-2-(5-(4-hydroxy-2, 5-dimethylbenzylidene)-4-oxo-2-thioxothiazolidin-3-yl) acetic acid (HBRAA-2,5DM); (Z)-2-(5-(4-hydroxy-3, 5-dimethylbenzylidene)-4-oxo-2-thioxothiazolidin-3-yl)acetic acid (HBRAA-3,5DM) and (Z)-2-(5-(4-hydroxy-3, 5-dimethoxybenzylidene)-4-oxo-2-thioxothiazolidin-3-yl) acetic acid (HBRAA-3,5DOM).

According to one embodiment, the complementation system of the invention comprises:

a first PYP fragment as described hereinabove, or a truncated fragment thereof as described hereinabove;

a second PYP fragment of the invention comprising or consisting of an amino acid sequence as set forth in SEQ ID NO: 34, or an amino acid sequence having at least about 30%, 35%, 40%, 45%, 50%, 55%, 60% or 65% identity, preferably at least about 70%, 75%, 80%, 85% or 90% or more identity with the amino acid sequence as set forth in SEQ ID NO: 34; and a fluorogenic HBR analog selected form the list comprising or consisting of HMBR, HBR-3,5DOM, HBR-30M and HBR-3,5DM.

In one embodiment, the complementation system of the invention comprises a first PYP fragment as described hereinabove, or a truncated fragment thereof as described hereinabove; a second PYP fragment of the invention comprising or consisting of an amino acid sequence as set forth in SEQ ID NO: 34, or an amino acid sequence having at least about 30%, 35%, 40%, 45%, 50%, 55%, 60% or 65% identity, preferably at least about 70%, 75%, 80%, 85% or 90% or more identity with the amino acid sequence as set forth in SEQ ID NO: 34; and HMBR or HBR-3,5DOM.

In one embodiment, the complementation system of the invention comprises a first PYP fragment as described hereinabove, or a truncated fragment thereof as described hereinabove; a second PYP fragment of the invention comprising or consisting of an amino acid sequence as set forth in SEQ ID NO: 34, or an amino acid sequence having at least about 30%, 35%, 40%, 45%, 50%, 55%, 60% or 65% identity, preferably at least about 70%, 75%, 80%, 85% or 90% or more identity with the amino acid sequence as set forth in SEQ ID NO: 34; and HMBR.

In one embodiment, the complementation system of the invention comprises a first PYP fragment as described hereinabove, or a truncated fragment thereof as described hereinabove; a second PYP fragment of the invention comprising or consisting of an amino acid sequence as set forth in SEQ ID NO: 34, or an amino acid sequence having at least about 30%, 35%, 40%, 45%, 50%, 55%, 60% or 65% identity, preferably at least about 70%, 75%, 80%, 85% or 90% or more identity with the amino acid sequence as set forth in SEQ ID NO: 34; and HBR-3,5DOM.

In one embodiment, the complementation system of the invention comprises a first PYP fragment as described hereinabove, or a truncated fragment thereof as described hereinabove; a second PYP fragment of the invention comprising or consisting of an amino acid sequence as set forth in SEQ ID NO: 34, or an amino acid sequence having at least about 30%, 35%, 40%, 45%, 50%, 55%, 60% or 65% identity, preferably at least about 70%, 75%, 80%, 85% or 90% or more identity with the amino acid sequence as set forth in SEQ ID NO: 34; and HBR-30M.

In one embodiment, the complementation system of the invention comprises a first PYP fragment as described hereinabove, or a truncated fragment thereof as described hereinabove; a second PYP fragment of the invention comprising or consisting of an amino acid sequence as set forth in SEQ ID NO: 34, or an amino acid sequence having at least about 30%, 35%, 40%, 45%, 50%, 55%, 60% or 65% identity, preferably at least about 70%, 75%, 80%, 85% or 90% or more identity with the amino acid sequence as set forth in SEQ ID NO: 34; and HBR-3,5DM.

According to one embodiment, the complementation system of the invention comprises:

a first PYP fragment comprising or consisting of an amino acid sequence as set forth in SEQ ID NO: 23 or SEQ ID NO: 30, or a truncated fragment thereof, or an amino acid sequence having at least about 30%, 35%, 40%, 45%, 50%, 55%, 60% or 65% identity, preferably at least about 70%, 75%, 80%, 85%, 90%, 91%, 92%, 93%, 94%, 95%, 96%, 97%, 98% or 99% or more identity with the amino acid sequence as set forth in SEQ ID NO: 23 or SEQ ID NO: 30, or a truncated fragment thereof;

a second PYP fragment of the invention comprising or consisting of an amino acid sequence as set forth in SEQ ID NO: 34, or an amino acid sequence having at least about 30%, 35%, 40%, 45%, 50%, 55%, 60% or 65% identity, preferably at least about 70%, 75%, 80%, 85% or 90% or more identity with the amino acid sequence as set forth in SEQ ID NO: 34; and a fluorogenic HBR analog selected form the list comprising or consisting of HMBR, HBR-3,5DOM, HBR-30M and HBR-3,5DM, preferably the fluorogenic HBR analog is HMBR or HBR-3,5DOM.

According to one embodiment, the complementation system of the invention comprises:

a first PYP fragment as described hereinabove, or a truncated fragment thereof as described hereinabove;

a second PYP fragment of the invention comprising or consisting of an amino acid sequence as set forth in SEQ ID NO: 42, or an amino acid sequence having at least about 30%, 35%, 40%, 45%, 50%, 55%, 60% or 65% identity, preferably at least about 70%, 75%, 80%, 85% or 90% or more identity with the amino acid sequence as set forth in SEQ ID NO: 42; and a fluorogenic HBR analog selected form the list comprising or consisting of HMBR, HBR-3,5DOM, HBR-30M and HBR-3,5DM.

In one embodiment, the complementation system of the invention comprises a first PYP fragment as described hereinabove, or a truncated fragment thereof as described hereinabove; a second PYP fragment of the invention comprising or consisting of an amino acid sequence as set forth in SEQ ID NO: 42, or an amino acid sequence having at least about 30%, 35%, 40%, 45%, 50%, 55%, 60% or 65% identity, preferably at least about 70%, 75%, 80%, 85% or 90% or more identity with the amino acid sequence as set forth in SEQ ID NO: 42; and HMBR or HBR-3,5DOM.

In one embodiment, the complementation system of the invention comprises a first PYP fragment as described hereinabove, or a truncated fragment thereof as described hereinabove; a second PYP fragment of the invention comprising or consisting of an amino acid sequence as set forth in SEQ ID NO: 42, or an amino acid sequence having at least about 30%, 35%, 40%, 45%, 50%, 55%, 60% or 65% identity, preferably at least about 70%, 75%, 80%, 85% or 90% or more identity with the amino acid sequence as set forth in SEQ ID NO: 42; and HMBR.

In one embodiment, the complementation system of the invention comprises a first PYP fragment as described hereinabove, or a truncated fragment thereof as described hereinabove; a second PYP fragment of the invention comprising or consisting of an amino acid sequence as set forth in SEQ ID NO: 42, or an amino acid sequence having at least about 30%, 35%, 40%, 45%, 50%, 55%, 60% or 65% identity, preferably at least about 70%, 75%, 80%, 85% or 90% or more identity with the amino acid sequence as set forth in SEQ ID NO: 42; and HBR-3,5DOM.

In one embodiment, the complementation system of the invention comprises a first PYP fragment as described hereinabove, or a truncated fragment thereof as described hereinabove; a second PYP fragment of the invention comprising or consisting of an amino acid sequence as set forth in SEQ ID NO: 42, or an amino acid sequence having at least about 30%, 35%, 40%, 45%, 50%, 55%, 60% or 65% identity, preferably at least about 70%, 75%, 80%, 85% or 90% or more identity with the amino acid sequence as set forth in SEQ ID NO: 42; and HBR-30M.

In one embodiment, the complementation system of the invention comprises a first PYP fragment as described hereinabove, or a truncated fragment thereof as described hereinabove; a second PYP fragment of the invention comprising or consisting of an amino acid sequence as set forth in SEQ ID NO: 42, or an amino acid sequence having at least about 30%, 35%, 40%, 45%, 50%, 55%, 60% or 65% identity, preferably at least about 70%, 75%, 80%, 85% or 90% or more identity with the amino acid sequence as set forth in SEQ ID NO: 42; and HBR-3,5DM.

In one embodiment, the complementation system of the invention comprises:

a first PYP fragment comprising or consisting of an amino acid sequence as set forth in SEQ ID NO: 23 or SEQ ID NO: 30, or a truncated fragment thereof, or an amino acid sequence having at least about 30%, 35%, 40%, 45%, 50%, 55%, 60% or 65% identity, preferably at least about 70%, 75%, 80%, 85%, 90%, 91%, 92%, 93%, 94%, 95%, 96%, 97%, 98% or 99% or more identity with the amino acid sequence as set forth in SEQ ID NO: 23 or SEQ ID NO: 30, or a truncated fragment thereof;

a second PYP fragment of the invention comprising or consisting of an amino acid sequence as set forth in SEQ ID NO: 42, or an amino acid sequence having at least about 30%, 35%, 40%, 45%, 50%, 55%, 60% or 65% identity, preferably at least about 70%, 75%, 80%, 85% or 90% or more identity with the amino acid sequence as set forth in SEQ ID NO: 42; and a fluorogenic HBR analog selected form the list comprising or consisting of HMBR, HBR-3,5DOM, HBR-30M and HBR-3,5DM, preferably the fluorogenic HBR analog is HMBR or HBR-3,5DOM.

According to one embodiment, the complementation system of the invention comprises:

a first PYP fragment as described hereinabove, or a truncated fragment thereof as described hereinabove;

a second PYP fragment of the invention comprising or consisting of an amino acid sequence as set forth in SEQ ID NO: 43, or an amino acid sequence having at least about 30%, 35%, 40%, 45%, 50%, 55%, 60% or 65% identity, preferably at least about 70%, 75%, 80%, 85% or 90% or more identity with the amino acid sequence as set forth in SEQ ID NO: 43; and a fluorogenic HBR analog selected form the list comprising or consisting of HMBR, HBR-3,5DOM, HBR-30M and HBR-3,5DM.

In one embodiment, the complementation system of the invention comprises a first PYP fragment as described hereinabove, or a truncated fragment thereof as described hereinabove; a second PYP fragment of the invention comprising or consisting of an amino acid sequence as set forth in SEQ ID NO: 43, or an amino acid sequence having at least about 30%, 35%, 40%, 45%, 50%, 55%, 60% or 65% identity, preferably at least about 70%, 75%, 80%, 85% or 90% or more identity with the amino acid sequence as set forth in SEQ ID NO: 43; and HMBR or HBR-3,5DOM.

In one embodiment, the complementation system of the invention comprises a first PYP fragment as described hereinabove, or a truncated fragment thereof as described hereinabove; a second PYP fragment of the invention comprising or consisting of an amino acid sequence as set forth in SEQ ID NO: 43, or an amino acid sequence having at least about 30%, 35%, 40%, 45%, 50%, 55%, 60% or 65% identity, preferably at least about 70%, 75%, 80%, 85% or 90% or more identity with the amino acid sequence as set forth in SEQ ID NO: 43; and HMBR.

In one embodiment, the complementation system of the invention comprises a first PYP fragment as described hereinabove, or a truncated fragment thereof as described hereinabove; a second PYP fragment of the invention comprising or consisting of an amino acid sequence as set forth in SEQ ID NO: 43, or an amino acid sequence having at least about 30%, 35%, 40%, 45%, 50%, 55%, 60% or 65% identity, preferably at least about 70%, 75%, 80%, 85% or 90% or more identity with the amino acid sequence as set forth in SEQ ID NO: 43; and HBR-3,5DOM.

In one embodiment, the complementation system of the invention comprises a first PYP fragment as described hereinabove, or a truncated fragment thereof as described hereinabove; a second PYP fragment of the invention comprising or consisting of an amino acid sequence as set forth in SEQ ID NO: 43, or an amino acid sequence having at least about 30%, 35%, 40%, 45%, 50%, 55%, 60% or 65% identity, preferably at least about 70%, 75%, 80%, 85% or 90% or more identity with the amino acid sequence as set forth in SEQ ID NO: 43; and HBR-30M.

In one embodiment, the complementation system of the invention comprises a first PYP fragment as described hereinabove, or a truncated fragment thereof as described hereinabove; a second PYP fragment of the invention comprising or consisting of an amino acid sequence as set forth in SEQ ID NO: 43, or an amino acid sequence having at least about 30%, 35%, 40%, 45%, 50%, 55%, 60% or 65% identity, preferably at least about 70%, 75%, 80%, 85% or 90% or more identity with the amino acid sequence as set forth in SEQ ID NO: 43; and HBR-3,5DM.

In one embodiment, the complementation system of the invention comprises:

a first PYP fragment comprising or consisting of an amino acid sequence as set forth in SEQ ID NO: 23 or SEQ ID NO: 30, or a truncated fragment thereof, or an amino acid sequence having at least about 30%, 35%, 40%, 45%, 50%, 55%, 60% or 65% identity, preferably at least about 70%, 75%, 80%, 85%, 90%, 91%, 92%, 93%, 94%, 95%, 96%, 97%, 98% or 99% or more identity with the amino acid sequence as set forth in SEQ ID NO: 23 or SEQ ID NO: 30, or a truncated fragment thereof;

a second PYP fragment of the invention comprising or consisting of an amino acid sequence as set forth in SEQ ID NO: 43, or an amino acid sequence having at least about 30%, 35%, 40%, 45%, 50%, 55%, 60% or 65% identity, preferably at least about 70%, 75%, 80%, 85% or 90% or more identity with the amino acid sequence as set forth in SEQ ID NO: 43; and a fluorogenic HBR analog selected form the list comprising or consisting of HMBR, HBR-3,5DOM, HBR-30M and HBR-3,5DM, preferably the fluorogenic HBR analog is HMBR or HBR-3,5DOM.

According to one embodiment, the complementation system of the invention comprises:

a first PYP fragment as described hereinabove, or a truncated fragment thereof as described hereinabove;

a second PYP fragment of the invention comprising or consisting of an amino acid sequence as set forth in SEQ ID NO: 44, or an amino acid sequence having at least about 30%, 35%, 40%, 45%, 50%, 55%, 60% or 65% identity, preferably at least about 70%, 75%, 80%, 85% or 90% or more identity with the amino acid sequence as set forth in SEQ ID NO: 44; and a fluorogenic HBR analog selected form the list comprising or consisting of HMBR, HBR-3,5DOM, HBR-30M and HBR-3,5DM.

In one embodiment, the complementation system of the invention comprises a first PYP fragment as described hereinabove, or a truncated fragment thereof as described hereinabove; a second PYP fragment of the invention comprising or consisting of an amino acid sequence as set forth in SEQ ID NO: 44, or an amino acid sequence having at least about 30%, 35%, 40%, 45%, 50%, 55%, 60% or 65% identity, preferably at least about 70%, 75%, 80%, 85% or 90% or more identity with the amino acid sequence as set forth in SEQ ID NO: 44; and HMBR or HBR-3,5DOM.

In one embodiment, the complementation system of the invention comprises a first PYP fragment as described hereinabove, or a truncated fragment thereof as described hereinabove; a second PYP fragment of the invention comprising or consisting of an amino acid sequence as set forth in SEQ ID NO: 44, or an amino acid sequence having at least about 30%, 35%, 40%, 45%, 50%, 55%, 60% or 65% identity, preferably at least about 70%, 75%, 80%, 85% or 90% or more identity with the amino acid sequence as set forth in SEQ ID NO: 44; and HMBR.

In one embodiment, the complementation system of the invention comprises a first PYP fragment as described hereinabove, or a truncated fragment thereof as described hereinabove; a second PYP fragment of the invention comprising or consisting of an amino acid sequence as set forth in SEQ ID NO: 44, or an amino acid sequence having at least about 30%, 35%, 40%, 45%, 50%, 55%, 60% or 65% identity, preferably at least about 70%, 75%, 80%, 85% or 90% or more identity with the amino acid sequence as set forth in SEQ ID NO: 44; and HBR-3,5DOM.

In one embodiment, the complementation system of the invention comprises a first PYP fragment as described hereinabove, or a truncated fragment thereof as described hereinabove; a second PYP fragment of the invention comprising or consisting of an amino acid sequence as set forth in SEQ ID NO: 44, or an amino acid sequence having at least about 30%, 35%, 40%, 45%, 50%, 55%, 60% or 65% identity, preferably at least about 70%, 75%, 80%, 85% or 90% or more identity with the amino acid sequence as set forth in SEQ ID NO: 44; and HBR-30M.

In one embodiment, the complementation system of the invention comprises a first PYP fragment as described hereinabove, or a truncated fragment thereof as described hereinabove; a second PYP fragment of the invention comprising or consisting of an amino acid sequence as set forth in SEQ ID NO: 44, or an amino acid sequence having at least about 30%, 35%, 40%, 45%, 50%, 55%, 60% or 65% identity, preferably at least about 70%, 75%, 80%, 85% or 90% or more identity with the amino acid sequence as set forth in SEQ ID NO: 44; and HBR-3,5DM.

In one embodiment, the complementation system of the invention comprises:

a first PYP fragment comprising or consisting of an amino acid sequence as set forth in SEQ ID NO: 23 or SEQ ID NO: 30, or a truncated fragment thereof, or an amino acid sequence having at least about 30%, 35%, 40%, 45%, 50%, 55%, 60% or 65% identity, preferably at least about 70%, 75%, 80%, 85%, 90%, 91%, 92%, 93%, 94%, 95%, 96%, 97%, 98% or 99% or more identity with the amino acid sequence as set forth in SEQ ID NO: 23 or SEQ ID NO: 30, or a truncated fragment thereof;

a second PYP fragment of the invention comprising or consisting of an amino acid sequence as set forth in SEQ ID NO: 44, or an amino acid sequence having at least about 50%, 55%, 60% or 65% identity, preferably at least about 70%, 75%, 80%, 85% or 90% or more identity with the amino acid sequence as set forth in SEQ ID NO: 44; and a fluorogenic HBR analog selected form the list comprising or consisting of HMBR, HBR-3,5DOM, HBR-3OM and HBR-3,5DM, preferably the fluorogenic HBR analog is HMBR or HBR-3,5DOM.

According to one embodiment, the complementation system of the invention comprises:

a first PYP fragment comprising or consisting of an amino acid sequence as set forth in any one of SEQ ID NO: 23, SEQ ID NO: 24, SEQ ID NO: 25, SEQ ID NO: 26, SEQ ID NO: 27, SEQ ID NO: 28 or SEQ ID NO: 29, or a truncated fragment thereof as described hereinabove;

a second PYP fragment comprising or consisting of an amino acid sequence as set forth in any one of SEQ ID NO:34, SEQ ID NO: 35, SEQ ID NO: 36, SEQ ID NO: 37, SEQ ID NO: 38, SEQ ID NO: 39 or SEQ ID NO: 40, or a truncated fragment thereof as described hereinabove; and a fluorogenic HBR analog selected form the list comprising or consisting of HMBR, HBR-3,5DOM, HBR-3OM and HBR-3,5DM, preferably the fluorogenic HBR analog is HMBR or HBR-3,5DOM.

In one embodiment, the complementation system of the invention comprises:

a first PYP fragment comprising or consisting of an amino acid sequence as set forth in any one of SEQ ID NO: 23, SEQ ID NO: 24, SEQ ID NO: 25, SEQ ID NO: 26, SEQ ID NO: 27, SEQ ID NO: 28 or SEQ ID NO: 29, or a truncated fragment thereof as described hereinabove;

a second PYP fragment comprising or consisting of an amino acid sequence as set forth in any one of SEQ ID NO:34, SEQ ID NO: 35, SEQ ID NO: 36, SEQ ID NO: 37, SEQ ID NO: 38, SEQ ID NO: 39 or SEQ ID NO: 40, respectively, or a truncated fragment thereof as described hereinabove; and a fluorogenic HBR analog selected form the list comprising or consisting of HMBR, HBR-3,5DOM, HBR-3OM and HBR-3,5DM, preferably the fluorogenic HBR analog is HMBR or HBR-3,5DOM.

The present invention also relates to a kit comprising at least one vector comprising:

a first nucleic acid sequence encoding the first PYP fragment, or a truncated fragment thereof, as described hereinabove; and a second nucleic acid sequence encoding the second PYP fragment, or a truncated fragment thereof, as described hereinabove.

In one embodiment, the kit of the invention comprises at least one vector comprising:

a first nucleic acid sequence encoding a first PYP fragment comprising or consisting of an amino acid sequence as set forth in SEQ ID NO: 23 or a truncated fragment thereof as described hereinabove, or an amino acid sequence having at least about 30%, 35%, 40%, 45%, 50%, 55%, 60% or 65% identity, preferably at least about 70%, 75%, 80%, 85%, 90%, 91%, 92%, 93%, 94%, 95%, 96%, 97%, 98% or 99% or more identity with the amino acid sequence as set forth in SEQ ID NO: 23, or a truncated fragment thereof as described hereinabove; and a second nucleic acid sequence encoding a second PYP fragment comprising or consisting an amino acid sequence as set forth in SEQ ID NO: 34, or a truncated fragment thereof as described hereinabove, or an amino acid sequence having at least about 30%, 35%, 40%, 45%, 50%, 55%, 60% or 65% identity, preferably at least about 70%, 75%, 80%, 85% or 90% or more identity with the amino acid sequence as set forth in SEQ ID NO: 34, or a truncated fragment thereof as described hereinabove.

In one embodiment, the kit of the invention comprises at least one vector comprising:

a first nucleic acid sequence encoding a first PYP fragment comprising or consisting of an amino acid sequence as set forth in SEQ ID NO: 23 or a truncated fragment thereof as described hereinabove, or an amino acid sequence having at least about 30%, 35%, 40%, 45%, 50%, 55%, 60% or 65% identity, preferably at least about 70%, 75%, 80%, 85%, 90%, 91%, 92%, 93%, 94%, 95%, 96%, 97%. 98% or 99% or more identity with the amino acid sequence as set forth in SEQ ID NO: 23, or a truncated fragment thereof as described hereinabove; and a second nucleic acid sequence encoding a second PYP fragment comprising or consisting an amino acid sequence as set forth in SEQ ID NO: 34, SEQ ID NO: 42, SEQ ID NO: 43 or SEQ ID NO: 44, or an amino acid sequence having at least about 30%, 35%, 40%, 45%, 50%, 55%, 60% or 65% identity, preferably at least about 70%, 75%, 80%, 85% or 90% or more identity with the amino acid sequence as set forth in SEQ ID NO: 34, SEQ ID NO: 42, SEQ ID NO: 43 or SEQ ID NO: 44.

The present invention also relates to a kit comprising:

a first vector comprising a nucleic acid sequence encoding the first PYP fragment, or a truncated fragment thereof, as described hereinabove; and a second vector comprising a nucleic acid sequence encoding the second PYP fragment, or a truncated fragment thereof, as described hereinabove.

In one embodiment, the kit of the invention comprises:

a first vector comprising a nucleic acid sequence encoding a first PYP fragment comprising or consisting of an amino acid sequence as set forth in SEQ ID NO: 23 or a truncated fragment thereof as described hereinabove, or an amino acid sequence having at least about 30%, 35%, 40%, 45%, 50%, 55%, 60% or 65% identity, preferably at least about 70%, 75%, 80%, 85%, 90%, 91%, 92%, 93%, 94%, 95%, 96%, 97%, 98% or 99% or more identity with the amino acid sequence as set forth in SEQ ID NO: 23, or a truncated fragment thereof as described hereinabove; and a second vector comprising a nucleic acid sequence encoding a second PYP fragment comprising or consisting an amino acid sequence as set forth in SEQ ID NO: 34, or a truncated fragment thereof as described hereinabove, or an amino acid sequence having at least about 30%, 35%, 40%, 45%, 50%, 55%, 60% or 65% identity, preferably at least about 70%, 75%, 80%, 85% or 90% or more identity with the amino acid sequence as set forth in SEQ ID NO: 34, or a truncated fragment thereof as described hereinabove.

In one embodiment, the kit of the invention comprises:

a first vector comprising a nucleic acid sequence encoding a first PYP fragment comprising or consisting of an amino acid sequence as set forth in SEQ ID NO: 23 or a truncated fragment thereof as described hereinabove, or an amino acid sequence having at least about 30%, 35%, 40%, 45%, 50%, 55%, 60% or 65% identity, preferably at least about 70%, 75%, 80%, 85%, 90%, 91%, 92%, 93%, 94%, 95%, 96%, 97%, 98% or 99% or more identity with the amino acid sequence as set forth in SEQ ID NO: 23, or a truncated fragment thereof as described hereinabove; and a second vector comprising a nucleic acid sequence encoding a second PYP fragment comprising or consisting an amino acid sequence as set forth in SEQ ID NO: 34, SEQ ID NO: 42, SEQ ID NO: 43 or SEQ ID NO: 44, or an amino acid sequence having at least about 30%, 35%, 40%, 45%, 50%, 55%, 60% or 65% identity, preferably at least about 70%, 75%, 80%, 85% or 90% or more identity with the amino acid sequence as set forth in SEQ ID NO: 34, SEQ ID NO: 42, SEQ ID NO: 43 or SEQ ID NO: 44.

The present invention also relates to a kit comprising:

a first biological molecule of interest as described hereinabove comprising the first PYP fragment, or a truncated fragment thereof, as described hereinabove; and a second biological molecule of interest as described hereinabove comprising the second PYP fragment, or a truncated fragment thereof, as described hereinabove.

The present invention also relates to a kit comprising:

a first fusion protein comprising the first PYP fragment, or a truncated fragment thereof, as described hereinabove; and a second fusion protein comprising the second PYP fragment, or a truncated fragment thereof, as described hereinabove.

The present invention also relates to a kit comprising:

a first fusion protein comprising the first PYP fragment, or a truncated fragment thereof, as described hereinabove and a reporter protein; and a second fusion protein comprising the second PYP fragment, or a truncated fragment thereof, as described hereinabove and a reporter protein, wherein the reporter proteins are identical or different.

The present invention also relates to a kit comprising a cell or a population of cells as described hereinabove.

In one embodiment, the kit of the invention comprises a cell or a population of cells expressing a first fusion protein comprising the first PYP fragment as described hereinabove, or a truncated fragment thereof as described hereinabove, and a reporter protein; and a second fusion protein comprising the second PYP fragment as described hereinabove, or a truncated fragment thereof as described hereinabove, and a reporter protein.

According to one embodiment, the kit as described hereinabove further comprises at least one fluorogenic HBR analog as described hereinabove.

The present invention also relates to a method for detecting an interaction between two biological molecules of interest in a sample, preferably two proteins of interest, comprising the steps of:

attaching a first fragment of PYP as described hereinabove, or a truncated fragment thereof as described hereinabove, to a first biological molecule of interest;

attaching a second fragment of PYP as described hereinabove, or a truncated fragment thereof as described hereinabove, to a second biological molecule of interest;

contacting the sample with a fluorogenic HBR analog as described hereinabove; and detecting a fluorescence resulting from the binding of the fluorogenic HBR analog to the functional PYP, or a functional truncated fragment thereof, reconstituted upon interaction of the two biological molecules of interest;

thereby detecting the interaction of the two biological molecules of interest present in the sample, through the binding of the fluorogenic HBR analog to the functional PYP, or a functional truncated fragment thereof, reconstituted upon interaction of the two biological molecules of interest.

In one embodiment, the first biological molecule of interest is attached to the first PYP fragment as described hereinabove, or a truncated fragment thereof as described hereinabove, and the second biological molecule of interest is attached to the second PYP fragment as described hereinabove, or a truncated fragment thereof as described hereinabove.

Thus, in one embodiment, the method of the invention is for detecting an interaction in a sample between a first biological molecule of interest attached to the first PYP fragment, or a truncated fragment thereof, as described hereinabove and a second biological molecule of interest attached to the second PYP fragment, or a truncated fragment thereof as described hereinabove, and comprises the steps of:

contacting the sample with a fluorogenic HBR analog as described hereinabove; and detecting a fluorescence resulting from the binding of the fluorogenic HBR analog to the functional PYP, or a functional truncated fragment thereof, reconstituted upon interaction of the two biological molecules of interest;

thereby detecting the interaction of the two biological molecules of interest present in the sample, through the binding of the fluorogenic HBR analog to the functional PYP, or a functional truncated fragment thereof, reconstituted upon interaction of the two biological molecules of interest In one embodiment the first and second biological molecules of interest are identical. In one embodiment the first and second biological molecules of interest are different.

In a preferred embodiment, at least one of the biological molecules of interest is an amino acid chain such as a peptide, a polypeptide or a protein, preferably a protein. In such embodiment, at least one of the PYP fragments of the invention, or fragments thereof, may form with said at least one biological molecule a fusion or tagged protein.

In one embodiment, both the first and the second biological molecules of interest are amino acid chains such as a peptide, a polypeptide or a protein, preferably a protein.

The protein of interest may be a natural protein, a chimeric protein resulting from the fusion of various protein domains or a synthetic protein.

In one embodiment, the protein of interest is an intracellular protein, a membrane protein, a cell surface protein present at least in part at the extra membranous surface, or a secreted protein.

In one embodiment, the two biological molecules of interest are reporter proteins.

As used herein, the term reporter proteins refer to two proteins, the interaction of which reflects a variation in the sample. Examples of variation that can be followed using reporter proteins include, but are not limited to, cell signaling, gene expression, calcium concentration, cell-cell interaction, cell movement, cell death, intracellular transport, secretion, cell-cycle phase, and circadian rhythm.

According to one embodiment, the sample is a biological sample. In one embodiment the sample is an organism. In one embodiment, the organism is not a human organism. In one embodiment, the sample is a cell culture. Example of cells include yeast cells, bacteria cells, plant cells, animal cells. In one embodiment, the cells in the sample are alive. In one embodiment, the cells in the sample are fixed for microscopy and imaging.

Organisms considered in the context of the present invention are for instance, and without limitation, model organisms used in biomedical research such as for example, bacterium, yeast, fruit fly, nematode, zebrafish, mouse, rat, guinea pig, rabbit, and dog.

In one embodiment the previously produced, and optionally purified, PYP fragments of the invention, or truncated fragments thereof, attached to the biological molecules of interest, preferably proteins of interest, are injected inside the organism or cells.

In a preferred embodiment, the model organism or the cells in the sample, or a subset thereof, are modified to express the PYP fragments of the invention, or truncated fragments thereof, attached to the biological molecules of interest, preferably proteins of interest.

The skilled artisan is familiar with methods allowing to modify a model organism or cells in a culture in order for them to express a protein of interest. Examples of such methods include, without being limited to, transfection, electroporation, injection and transgenesis of nucleic acid sequences, such as a nucleic acid sequence as described hereinabove. Said methods also include, but are not limited to, transplantation, injection and co-culture of cells modified to express proteins of interest.

In one embodiment, the sample is an extract from cells modified to express the PYP fragments of the invention, or truncated fragments thereof, attached to biological molecules of interest, preferably proteins of interest.

In one embodiment, the sample is a cell extract complemented with the PYP fragments of the invention, or truncated fragments thereof, attached to biological molecules of interest, preferably proteins of interest.

In one embodiment, the sample is acellular or does not comprise cells producing a PYP fragment of the invention, or a truncated fragment thereof, attached to a biological molecule of interest. In such an embodiment, the PYP fragments of the invention, or truncated fragments thereof, attached to biological molecules of interest, preferably proteins of interest, previously produced, optionally purified, are added in the sample.

In one embodiment, the method for detecting an interaction between two biological molecules of interest in a sample, preferably two proteins of interest, comprises the steps of:

fusing a first fragment of PYP as described hereinabove, or a truncated fragment thereof as described hereinabove, to a first biological molecule of interest, preferably a first protein of interest;

fusing a second fragment of PYP as described hereinabove, or a truncated fragment thereof as described hereinabove, to a second biological molecule of interest, preferably a second protein of interest;

contacting the sample with a fluorogenic HBR analog as described hereinabove; and detecting a fluorescence resulting from the binding of the fluorogenic HBR analog to the functional PYP, or a functional truncated fragment thereof, reconstituted upon interaction of the two biological molecules of interest, preferably two proteins of interest;

thereby detecting the interaction of the two biological molecules of interest, preferably two proteins of interest, present in the sample, through the binding of the fluorogenic HBR analog to the functional PYP, or a functional truncated fragment thereof, reconstituted upon interaction of the two biological molecules of interest, preferably two proteins of interest.

As mentioned above, methods for fusing a peptide or a polypeptide, i.e., a PYP fragment according to the invention, or a truncated fragment thereof, to a protein of interest are well-known.

In one embodiment, the fluorogenic HBR analog is added in the sample at a concentration ranging from about 0.1 μM to about 50 μM, preferably ranging from about 1 μM to about 25 μM, more preferably ranging from about 1 μM to about 15 μM.

As used herein the term "interaction" means that the two biological molecules of interest, preferably the two proteins of interest, are sufficiently close for the two PYP fragments of the complementation system of the invention, or truncated fragments thereof, to bind each other and consequently form a functional PYP, or a functional truncated fragment thereof, able to bind a fluorogenic HBR analog.

According to one embodiment, the interaction is mediated by the direct binding of the two biological molecules of interest, preferably of the two proteins of interest, to each other.

According to one embodiment the interaction is indirect, i.e., is mediated by the binding of the two biological molecules of interest, preferably the two proteins of interest, to at least one other biological molecule.

Examples of biological molecules that may induce the interaction of the two biological molecules of interest, preferably of the two proteins of interest, include, without being limited to, cations, anions, peptides, metabolites, secondary messengers, RNAs, DNAs, and proteins.

Thus, in one embodiment, the method of the invention comprises the steps of:

attaching a first fragment of PYP as described hereinabove, or a truncated fragment thereof as described hereinabove, to a first biological molecule of interest;

attaching a second fragment of PYP as described hereinabove, or a truncated fragment thereof as described hereinabove, to a second biological molecule of interest;

contacting the sample with a fluorogenic HBR analog as described hereinabove; and detecting a fluorescence resulting from the binding of the fluorogenic HBR analog to the functional PYP, or a functional truncated fragment thereof, reconstituted upon induction by a biological molecule of the interaction of the two biological molecules of interest;

thereby detecting the interaction of the two biological molecules of interest present in the sample, through the binding of the fluorogenic HBR analog to the functional PYP, or a functional truncated fragment thereof, reconstituted upon induction by a biological molecule of the interaction of the two biological molecules of interest.

In one embodiment, the interaction is transient.

In one embodiment, the method of the invention comprises a step of detecting a variation of the fluorescence resulting from the binding of the fluorogenic HBR analog to the functional PYP, or a functional truncated fragment thereof, reconstituted upon interaction of the two biological molecules of interest.

In one embodiment, the method of the invention comprises a step of detecting an increase of the fluorescence resulting from the binding of the fluorogenic HBR analog to the functional PYP, or a functional truncated fragment thereof, reconstituted upon interaction of the two biological molecules of interest.

In one embodiment, the method of the invention comprises a step of detecting a decrease of the fluorescence resulting from the unbinding of the fluorogenic HBR analog upon disassembly of a functional PYP, or a functional truncated fragment thereof, resulting from the destruction of the interaction between two biological molecules of interest.

The person of the art is familiar with the techniques available to detect fluorescence in a sample and is able to choose among those depending on the sample, the excitation and emission spectra of the fluorophore(s) and the desired readout.

Such techniques include, but are not limited to, direct observation, fluorescence spectroscopy, flow cytometry, fluorescence microscopy, and fluorescence tomography.

In one embodiment, the method of the invention is for monitoring in space the interaction between the biological molecules of interest, preferably the proteins of interest, in a sample.

For example, the localization in the sample of the interaction between the biological molecules of interest, preferably proteins of interest, may be determined by:

(i) using a fluorescence detection technique allowing to determine the localization of the source of a fluorescence emission in a sample such as fluorescence tomography or fluorescence microscopy (including laser scanning- and spinning-disk based confocal microscopy, multiphoton-microscopy, super-resolution microscopy);

(ii) targeting the PYP fragments of the invention attached to the biological molecules of interest, preferably proteins of interest, to a particular cell population and/or subcellular compartment; and/or (iii) controlling the diffusion of the HBR analog in the sample, notably by using either membrane-permeant or membrane-impermeant HBR analogs as described hereinabove.

In one embodiment, the method of the invention further allows to measure the amount of the interacting biological molecules of interest relative to a reference value by measuring fluorescence intensity. In one embodiment, said reference value corresponds to the fluorescence intensity value in a control sample. In one embodiment, said reference value corresponds to the fluorescence intensity value(s) at a different location(s) and/or time point(s) in the same sample.

In one embodiment, the method of the invention is for monitoring over time the interaction between the biological molecules of interest, preferably proteins of interest, in a sample as described hereinabove.

In one embodiment, the method of the invention is for monitoring over time and/or space the interaction between the biological molecules of interest, preferably proteins of interest, in a sample as described hereinabove.

The present invention also relates to a screening method for identifying new a protein-protein interaction in a sample, comprising the steps of:

fusing a first fragment of PYP as described hereinabove, or a truncated fragment thereof as described hereinabove, to a first protein, thereby tagging the first protein with the first PYP fragment;

fusing a second fragment of PYP as described hereinabove, or a truncated fragment thereof as described hereinabove, to a second protein, thereby tagging the second protein with the second PYP fragment;

contacting the sample with a fluorogenic HBR analog as described hereinabove; and detecting a fluorescence resulting from the binding of the fluorogenic HBR analog to the functional PYP, or a functional truncated fragment thereof, reconstituted upon interaction of the two proteins;

thereby identifying a new protein-protein interaction between the two proteins present in the sample, through the binding of the fluorogenic HBR analog to the functional PYP, or a functional truncated fragment thereof, reconstituted upon interaction of the two proteins.

In one embodiment, the method of the invention is for screening new protein-protein interactions between a protein of interest and protein candidates which may interact with said protein of interest.

In one embodiment, the method of the invention is for screening protein-protein interactions induced by a biological molecule as described hereinabove, with examples of said biological molecule including, without being limited to, cations, anions, peptides, metabolites, secondary messengers, RNAs, DNAs, and proteins.

The present invention also relates to an assay relying on the detection of the interaction between two proteins in a sample, said assay comprising the steps of:

obtaining a first tagged protein, wherein the protein is tagged with a first PYP fragment as described hereinabove, or a truncated fragment thereof as described hereinabove;

obtaining a second tagged protein, wherein the protein is tagged with a second PYP fragment as described hereinabove, or a truncated fragment thereof as described hereinabove;

contacting the sample with a fluorogenic HBR analog; and detecting a fluorescence resulting from the binding of the fluorogenic HBR analog to the functional PYP, or a functional truncated fragment thereof, reconstituted upon interaction of the two tagged proteins;

thereby detecting the interaction of the two tagged proteins present in the sample, through the binding of the fluorogenic HBR analog to the functional PYP, or a functional truncated fragment thereof, reconstituted upon interaction of the two tagged proteins.

In one embodiment, the two proteins are reporter proteins.

In one embodiment, the assay of the invention is for assessing the capacity of a molecule of interest to stabilize or to inhibit protein-protein interactions.

Thus, according to one embodiment, the assay of the invention comprises the steps of:

contacting the sample with a molecule of interest;

detecting the fluorescence resulting from the binding of the fluorogenic HBR analog to the functional PYP, or a functional truncated fragment thereof, reconstituted upon interaction of the two proteins in the presence of said molecule of interest;

comparing the fluorescence resulting from the binding of the fluorogenic HBR analog to the functional PYP, or a functional truncated fragment thereof, reconstituted upon interaction of the two proteins detected in the absence and in the presence of the molecule of interest;

thereby assessing the effect of said molecule of interest on the interaction of the two proteins.

In one embodiment, a decrease of the fluorescence detected in the presence of the molecule of interest, as compared to the fluorescence detected in the absence of the molecule of interest, is indicative of an inhibition or destabilization of the interaction of the two proteins by the molecule of interest.

In one embodiment, an increase of the fluorescence detected in the presence of the molecule of interest, as compared to the fluorescence detected in the absence of the molecule of interest, is indicative of an induction or stabilization of the interaction of the two proteins by the molecule of interest.

In one embodiment, by "decrease or increase of the fluorescence" it is meant decrease or increase of the fluorescence intensity.

In one embodiment, the assay of the invention is for assessing a signaling pathway of interest, with the interaction of the two proteins depending on the activation or on the inactivation of the signaling pathway of interest.

In one embodiment, the assay of the invention is for detecting the activation of a signaling pathway. Thus, in one embodiment, the detection of a variation in the fluorescence resulting from the binding of the fluorogenic HBR analog to the functional PYP, or a functional truncated fragment thereof, reconstituted upon interaction of the two proteins, is indicative of an activation of the signaling pathway of interest.

In one embodiment, the assay of the invention is for detecting the inactivation of a signaling pathway. Thus, in one embodiment, the detection a variation of the fluorescence resulting from the binding of the fluorogenic HBR analog to the functional PYP reconstituted upon interaction of the two proteins, is indicative of an inactivation of the signaling pathway of interest.

In one embodiment, by "variation of the fluorescence" it is meant a decrease or an increase of the fluorescence intensity.

In one embodiment, the assay of the invention is for detecting the modulation of a signaling pathway. In one embodiment, the assay of the invention is for assessing the capacity of a molecule of interest to modulate a signaling pathway of interest. In one embodiment, the assay of the invention is for assessing the capacity of a molecule of interest to activate or to inactivate a signaling pathway of interest Thus, according to one embodiment, the assay of the invention comprises the steps of:

contacting the sample with a molecule of interest;

detecting the fluorescence resulting from the binding of the fluorogenic HBR analog to the functional PYP, or a functional truncated fragment thereof, reconstituted upon interaction of the two proteins in the presence of said molecule of interest;

comparing the fluorescence resulting from the binding of the fluorogenic HBR analog to the functional PYP, or a functional truncated fragment thereof, reconstituted upon interaction of the two proteins detected in the absence and in the presence of the molecule of interest;

thereby assessing the effect of said molecule of interest on the signaling pathway of interest on which depends the interaction of the two proteins.

The present invention also relates to an assay relying on the detection of the interaction between two proteins in a cell or cell population, said assay comprising the steps of:

expressing a first tagged protein in the cell or cell population, wherein the protein is tagged with a first PYP fragment as described hereinabove, or a truncated fragment thereof as described hereinabove;

expressing a second tagged protein in the cell or cell population, wherein the protein is tagged with a second PYP fragment as described hereinabove, or a truncated fragment thereof as described hereinabove;

contacting the cell or cell population with a fluorogenic HBR analog; and detecting a fluorescence resulting from the binding of the fluorogenic HBR analog to the functional PYP, or a functional truncated fragment thereof, reconstituted upon interaction of the two tagged proteins in the cell or cell population;

thereby detecting the interaction of the two tagged proteins present in the cell or cell population, through the binding of the fluorogenic HBR analog to the functional PYP, or a functional truncated fragment thereof, reconstituted upon interaction of the two tagged proteins.

According to one embodiment, the assay of the invention is for assessing the presence of an analyte of interest in the cell or cell population, with the interaction of the two proteins depending on the presence in the cell or cell population of the analyte of interest.

Thus, in one embodiment, detecting a fluorescence resulting from the binding of the fluorogenic HBR analog to the functional PYP, or a functional truncated fragment thereof, reconstituted upon interaction of the two proteins in the cell or cell population is indicative of the presence of the analyte of interest in the cell or cell population.

In one embodiment, the assay of the invention is for detecting a variation of calcium concentration in a cell or cell population.

According to one embodiment, the assay of the invention is for assessing a signaling pathway of interest in the cell or cell population, with the interaction of the two proteins depending on the activation or on the inactivation of said signaling pathway in the cell or cell population.

Thus, in one embodiment, detecting a fluorescence resulting from the binding of the fluorogenic HBR analog to the functional PYP, or a functional truncated fragment thereof, reconstituted upon interaction of the two proteins in the cell or cell population is indicative of the activation or inactivation of the signaling pathway of interest in the cell or cell population.

In one embodiment, the assay of the invention is for detecting a modulation of the mitogen-activated protein kinase pathway in a cell or cell population.

According to one embodiment, the assay of the invention is for assessing a physiological mechanism of interest of the cell or cell population, with the interaction of the two proteins depending on said physiological mechanism of the cell or cell population.

Thus, in one embodiment, detecting a fluorescence resulting from the binding of the fluorogenic HBR analog to the functional PYP, or a functional truncated fragment thereof, reconstituted upon interaction of the two proteins in the cell or cell population is indicative of the activation or inactivation of the physiological mechanism of interest of the cell or cell population.

In one embodiment, the assay of the invention is for detecting apoptosis in a cell or cell population, for example through the detection of caspase-3 activation in the cell or cell population.

EXAMPLES

The present invention is further illustrated by the following examples.

Materials and Methods

Synthetic oligonucleotides used for cloning were purchased from SIGMA-ALDRICH® or Integrated DNA Technology. The sequences of the oligonucleotides used in this study are provided in Table 1. Polymerase chain reactions (PCRs) were performed with Q5® polymerase (NEW ENGLAND BIOLABS®) in the buffer provided. PCR products were purified using QIAQUICK® PCR purification kit (QIAGEN®). The products of restriction enzyme digestions were purified by preparative gel electrophoresis followed by QIAQUICK® gel extraction kit (QIAGEN®). Restriction endonucleases, T4 ligase, PHUSION® polymerase, Taq ligase, and Taq exonuclease were purchased from NEW ENGLAND BIOLABS® and used with their accompanying buffers according to manufacturer's protocols. Isothermal assemblies (GIBSON ASSEMBLY®) were performed using a homemade mix prepared according to Gibson et al., Nat.

Meth. 6, 343-345 (2009). Small-scale isolation of plasmid DNA was done using QIAprep miniprep kit (QIAGEN®) from 2 mL of overnight culture. Large-scale isolation of plasmid DNA was done using the QIAprep maxiprep kit (QIAGEN®) from 150 mL of overnight culture. All plasmid sequences were confirmed by Sanger sequencing with appropriate sequencing primers (GATC-Biotech). Table 2 lists the plasmids used in this study. Peptides corresponding to CFASTI1-8 were purchased from Clinisciences at 98% purity and are acetylated and amidated at the N and C termini. Rapamycin was purchased from SIGMA-ALDRICH® and dissolved in DMSO to a concentration of 3 mM. AP1510 was purchased from CLONTECH® and dissolved in ethanol to a concentration of 0.5 mM. Human recombinant EGF was purchased from SIGMA-ALDRICH® and dissolved in 0.1% BSA to a concentration of 100 μg/mL. Staurosporine was purchased from Cell Signaling Technologies and dissolved in ethanol to a concentration of 1 mM. HMBR (4-hydroxy-3-methylbenzylidene rhodanine) and HBR-3,5DOM (4-hydroxy-3,5-dimethoxybenzylidene rhodanine) were provided by The Twinkle Factory under the references $^{TF}$Lime and $^{TF}$Coral (thetwinklefactory.com).

TABLE 1 list of oligonucleotides.

| SEQ ID NO: | Primer code | Sequence |
| --- | --- | --- |
| SEQ ID NO: 63 | ag126 | gtggtgctcgagctattaggaaagggctttcttcatgtgc |
| SEQ ID NO: 64 | ag176 | agagtcgcggccgcctattaggaaagggctttcttcatgtgcac |
| SEQ ID NO: 65 | ag175 | gcagcggcggagggggatccatggagcatgttgcctttggc |
| SEQ ID NO: 66 | ag181 | ggactcagatctgccaccatggaacaaaagcttatttctgaagaggacttggaattcgagatgtggcatgaaggcctg |
| SEQ ID NO: 67 | ag182 | ggatcccctccgccgctgccgcctcctccggagacctgctttgagattcgtcgg |
| SEQ ID NO: 68 | ag183 | ggactcagatctgccaccatggaacaaaagcttatttctgaagaggacttggaattcggagtgcaggtggaaaccatc |
| SEQ ID NO: 69 | ag184 | ggatcccctccgccgctgccgcctcctccggattcttccagttttagaagctccacatc |
| SEQ ID NO: 70 | ag216 | ttcgtagctagcatggagcatgttgcctttg |
| SEQ ID NO: 71 | ag311 | aaagcttatttctgaagaggacttgtaataggcggccgcgactctagatcataatc |
| SEQ ID NO: 72 | ag313 | ctcaccttgctcctgccgagaaagtatcca |
| SEQ ID NO: 73 | ag314 | tggatactttctcggcaggagcaaggtgag |
| SEQ ID NO: 74 | ag345 | ctagagtcgcggccgcctattaccgtttcacaaagacccaatagc |
| SEQ ID NO: 75 | ag346 | ctagagtcgcggccgcctattatttcacaaagacccaatagctgtcac |
| SEQ ID NO: 76 | ag347 | taataggcggccgcgactctag |
| SEQ ID NO: 77 | ag358 | ggtggcagatctgagtccggtag |
| SEQ ID NO: 78 | ag412 | caagtcctcttcagaaataagcttttgttc |
| SEQ ID NO: 79 | ag414 | gcttatttctgaagaggacttggtgagcaagggcgaggag |
| SEQ ID NO: 80 | ag415 | gaattcgaagcttgagctcgagatctgagtccggacttgtacagctcgtccatgc |
| SEQ ID NO: 81 | ag416 | ctcgagctcaagcttcgaattctg |
| SEQ ID NO: 82 | ag417 | ccgctgccgcctcctccggaagatctgtatcctggctggaatctag |

TABLE 1-continued list of oligonucleotides.

| SEQ ID NO: | Primer code | Sequence |
|---|---|---|
| SEQ ID NO: 83 | ag418 | gcagcggcggaggggggatccatgcccaagaagaagccgac |
| SEQ ID NO: 84 | ag419 | caagtcctcttcagaaataagcttttgttcgacgccagcagcatgg |
| SEQ ID NO: 85 | ag455 | gactgcgtgacctgtcttattccacttacgacgtgatgagtcgaccatgaattcc aagtcctcttcagaaataagc |
| SEQ ID NO: 86 | ag456 | ggaataagacaggtcacgcagtcagagctataggtcggctgagctcatccgg aggaggcg |
| SEQ ID NO: 87 | ag465 | caagtcctcttcagaaataagcttttgttcggatcccttcgctgtcatc |
| SEQ ID NO: 88 | ag466 | ggaggaggcggcagcggcggaggggggatccgaccaattgactgaagagca gatcgcag |
| SEQ ID NO: 89 | ag467 | gctgccgcctcctccggaccgtttcacaaagacccaatag |
| SEQ ID NO: 90 | ag468 | caagtccaagggcaaggactccgccgaacaaaagcttatttctgaagaggact tg |
| SEQ ID NO: 91 | ag469 | ggagtccttgcccttggacttgatgcagcccatggtggcagatctgagtcc |
| SEQ ID NO: 92 | ag474 | ctaccggactcagatctgccaccagtggtgacagctattgggtctttg |
| SEQ ID NO: 93 | ag475 | ctagagtcgcggccgcctattacataattacacactagtctttgacttctattc |
| SEQ ID NO: 94 | ag535 | atccaaaaaagaagagaaaggtagatccaaaaaagaagagaaaggtagatc caaaaaagaagagaaaggtaggtaccgcctccggcgatgaggtggatgg |
| SEQ ID NO: 95 | ag539 | ccttgaaattagcaggtcttgatatcgggagctaataggcggccgcgactctag |
| SEQ ID NO: 96 | ag541 | ctagagtcgcggccgcctattacacccgtttcacaaagaccc |
| SEQ ID NO: 97 | ag542 | ccggactcagatctgccaccatgggtcgtgcgcagtc |
| SEQ ID NO: 98 | ag543 | ctacctactcacttattggatcggaaagggctttcttcatgtgc |
| SEQ ID NO: 99 | ag544 | ccggactcagatctgccaccatgaaggcggagaggaagc |
| SEQ ID NO: 100 | ag545 | ctccggcgatgaggtggatggagtgagcaagggcgaggag |
| SEQ ID NO: 101 | ag546 | gatatcaagacctgctaatttcaaggctaaggatcccttgtacagctcgtccatg cc |
| SEQ ID NO: 102 | ag550 | tgctgaagcaggctggagacgtggaggagaaccctggacctgtgagcaagg gcgaggagg |
| SEQ ID NO: 103 | ag694 | taactcgaggactacaaggacgacg |
| SEQ ID NO: 104 | ag695 | ctcctcgcccagctcaccatgaattcagcgtaatctggaacatcgtatg |
| SEQ ID NO: 105 | ag696 | tggacgagctgtacaagtaataggcggccgcgactc |
| SEQ ID NO: 106 | ag697 | cgtcgtccagtagtcctcgagttaggaaagggctacttcatgtgcac |
| SEQ ID NO: 107 | ag698 | cgtcgtccagtagtcctcgagttacataattacacactagtctttgacttctattc |
| SEQ ID NO: 108 | ag700 | cgtcgtccagtagtcctcgagttaccgtttcacaaagacccaatagc |
| SEQ ID NO: 109 | ag701 | gataatatggccacaaccatgcgatcggtgagcaagggcgaggag |

TABLE 2 list of plasmids.

| Plasmid name | Open Reading Frame | Extended Description |
|---|---|---|
| pAG144 | CFAST11-FKBP | CMV-CFAST11-linker-FRB |
| pAG148 | FRB-NFAST | CMV-cmyc-FRB-linker-NFAST |
| pAG149 | FKBP-NFAST | CMV-cmyc-FKBP-linker-NFAST |
| pAG152 | FRB-CFAST11 | CMV-cmyc-FRB-linker-CFAST(115-125) |

TABLE 2-continued list of plasmids.

| Plasmid name | Open Reading Frame | Extended Description |
|---|---|---|
| pAG153 | FKBP-CFAST11 | CMV-cmyc-FKBP-linker-CFAST-11 |
| pAG179 | IAAL-E3-CFAST(65-125) + NFAST(1-64)-IAAL-K3 | T7-Histag-TEV-IAAL-E3-CFAST(65-125)-T7-NFAST(1-64)-IAAL-K3-TEV-Stag |
| pAG180 | IAAL-E3-CFAST(115-125) + NFAST(1-114)_IAAL-K3 | T7-Histag-TEV-IAAL-E3-CFAST(115-125)-T7-NFAST(1-114)-IAAL-K3-TEV-Stag |
| pAG181 | IAAL-K3_NFAST(1-64) + CFAST(65-125)_IAAL-E3 | T7-Histag-TEV-IAAL-K3-NFAST(1-64)-T7-CFAST(65-125)-IAAL-E3-TEV-Stag |
| pAG182 | IAAL-K3_NFAST(1-114) + CFAST(115-125)_IAAL-E3 | T7-Histag-TEV-IAAL-K3-NFAST(1-114)-T7-CFAST(115-125)-IAAL-E3-TEV-Stag |
| pAG209 | Histag-NFAST | pET28a-Histag-NFAST(1-114) |
| pAG241 | FKBP-CFAST10 | CMV-cmyc-FKBP-linker-CFAST-10 |
| pAG296 | mCherry-ERK2-CFAST10 | CMV-myc-mCherry-ERK-CFAST10 |
| pAG298 | NFAST-MEK1 | CMV-NFAST-MEK-myc |
| pAG301 | NFAST-MKP1 | CMV-NFAST-MKP1-myc |
| pAG334 | M13-NFAST | CMV-myc-M13-NFAST |
| pAG335 | CFAST10-CaM | CMV-CFAST10-CaM-myc |
| pAG336 | lyn11-FRB-NFAST | CMV-lyn11-cmyc-FRB-NFAST |
| pAG340 | CFAST10-Raf1-mCherry | CMV-CFAST10-Raf1-mCherry-myc |
| pAG341 | NFAST-KRas | CMV-NFAST-myc-KRas |
| pAG384 | bFos-CFAST11 | CMV-bFos-myc-CFAST11 |
| pAG385 | bJun-NFAST-NLS-DEVDG-mCherry-NES | CMV-bJun-myc-NFAST-NLSx3-DEVDG-mCherry-NES |
| pAG435 | FRB-NFAST-P2A-EGFP | CMV-myc-FRB-NFAST-P2A-EGFP-myc |
| pAG436 | FRB-NFAST(V107I)-P2A-EGFP | CMV-myc-FRB-NFAST(V107I)-P2A-EGFP-myc |
| pAG439 | FRB-NFAST-P2A-mCherry | CMV-myc-FRB-NFAST-P2A-mCherry-myc |
| pAG440 | FRB-NFAST(V107I)-P2A-mCherry | CMV-myc-FRB-NFAST(V107I)-P2A-mCherry-myc |
| pAG490 | FRB-NFAST-IRES-mTurquoise2 | CMV-cmyc-FRB-NFAST-IRES-HA-mTurquoise2 |
| pAG491 | lyn11-FRB-NFAST-IRES-mTurquoise2 | CMV-lyn11-cmyc-FRB-NFAST-IRES-HA-mTurquoise2 |
| pAG492 | NFAST-MEK1-IRES-mTurquoise2 | CMV-NFAST-MEK-myc-IRES-HA-mTurquoise2 |
| pAG493 | NFAST-MKP1-IRES-mTurquoise2 | CMV-NFAST-MKPl-myc-IRES-HA-mTurquoise2 |
| pAG494 | NFAST-KRas-IRES-mTurquoise2 | CMV-NFAST-myc-KRas-IRES-HA-mTurquoise2 |
| pAG496 | FKBP-CFAST10-IRES-mCherry | CMV-myc-FKBP-cfast10-IRES-mCherry-myc |

Molecular Cloning

Bacterial Expression Plasmids

The plasmid pAG209 was obtained by inserting the gene encoding for NFAST (amplified using primers ag126 and ag216) into plasmid pET28a using restriction enzymes Nhe I and Xho I.

FRB-FKBP Fusion Plasmids for Mammalian Expression

In general, fusion proteins were constructed by PCR assembly and contain an 11 amino acid linker, SGGGGSGGGGS (SEQ ID NO: 45), between the two proteins. The plasmid pAG148 was obtained by inserting the gene encoding FRB-NFAST (the sequence coding for FRB-NFAST was assembled by PCR from the sequences coding for FKBP-rapamycin binding domain of mTOR (FRB) and NFAST amplified with the primers ag181/ag182 and ag175/ag176) into plasmid pAG1042 using the restriction enzymes, Bgl II and Not I. The plasmid pAG149 was generated by inserting the gene encoding FKBP-NFAST (the sequence coding for FKBP-NFAST was assembled by PCR from the sequences coding for FK506 binding protein (FKBP) and NFAST amplified with the primers ag183/ag184 and ag175/ag176) into plasmid pAG104 using the restriction enzymes Bgl II and Not I. The plasmid pAG152 was obtained by inserting the gene encoding FRB-CFAST11 (synthesized by EUROFINS® Genomics) into pAG104 using restriction enzymes Bgl II and Not I. The plasmid pAG153 was generated by inserting the gene coding for FKBP (amplified using primers ag183 and ag184) into pAG152 using restriction enzymes Bgl II and BspE I.

The plasmid pAG241 was constructed by GIBSON ASSEMBLY® of two fragments obtained by amplification of the plasmid pAG153 with the primers ag345/ag313 and ag347/ag314. The plasmid pAG336 was cloned by GIBSON ASSEMBLY® of two fragments obtained by amplification of the plasmid pAG148 with the primers ag468/313 and ag469/314.

To determine the photostability of split-FAST in cells, the plasmid pAG439 encoding FRB-NFAST-P2A-mCherry was generated by GIBSON ASSEMBLY® of the sequences of FRB-NFAST (amplified from pAG148 with primers ag308 and ag313) and mCherry (amplified from pAG962 with ag412 and ag550) assembled with the plasmid backbone of pAG104 (amplified using primers and ag347 and ag314). The plasmid pAG496 encoding FKBP-CFAST10-IRESmCherry was cloned from the plasmid pAG241 (amplified using ag700 and ag313), mCherry (amplified using ag701 and ag314), and the IRES sequence amplified from the plasmid pIRES (using primers ag694 and ag695) via GIBSON ASSEMBLY®. The plasmid pAG490 encoding FRB-NFAST-IRES-mTurquoise2 was cloned from the plasmid pAG148 (amplified using ag697 and ag313), the IRES sequence amplified from the plasmid pIRES (using ag694 and ag695), and a g-block encoding mTurquoise2 (IDT®). The plasmid pAG491 encoding lyn11-FRB-NFAST-IRES-mTurquoise2 was cloned from the plasmid pAG336 (amplified using ag697 and ag313), the IRES sequence amplified from the plasmid pIRES (using ag694 and ag695), and a g-block encoding mTurquoise2 (IDT®).

Signaling Pathway Plasmids

The genes coding for NFAST-MKP1 (MKP1 GenBank accession number: NM_004417.3), NFAST-KRas (K-Ras GenBank accession number: NM_004985.4), and CFAST10-Raf1-mCherry (Raf1 GenBank accession number: NM_001354689.1) were synthesized by EUROFINS® genomics. The plasmids pAG301, pAG341 and pAG340 were generated via GIBSON ASSEMBLY® of the sequences of NFAST-MKP1 (amplified using ag357/ag412), NFAST-KRas (amplified using ag357/ag475), and CFAST10-Raf1-mCherry (amplified using ag474/ag412), and the backbone of pAG104 amplified in two fragments using primers ag311/ag314 and ag358/ag313. The genes coding for MEK1, ERK2, and mCherry were amplified using primers ag418/419, ag416/417, and ag414/415, respectively, and assembled via GIBSON ASSEMBLY® with the corresponding fragments of NFAST (amplified with primers 374/313) and CFAST0 (amplified with primers 413/314) to generate the plasmids pAG298 and pAG296 encoding NFAST-MEK1 and mCherry-ERK2-CFAST10, respectively. The plasmids pAG492, pAG493 and pAG494 were constructed by GIBSON ASSEMBLY® from the initial plasmid encoding the signaling pathway partner pAG298, pAG301, pAG341 (amplified with primers 697/313, 696/314, 699/313, 698/313), the IRES sequence (amplified from the plasmid pIRES using ag694 and ag695), and a g-block encoding mTurquoise2 (IDT®).

Sensor Construction

The plasmid pAG334 was generated from the plasmid pAG148 by GIBSON ASSEMBLY® by amplifying NFAST using primers ag455/ag456 with M13 encoded, and the backbone of pAG148 with primers ag313/ag314. The plasmid pAG335 was generated by GIBSON ASSEMBLY® by amplification of calmodulin using primers ag465 and ag466, and inserted into the plasmid pAG144 by amplifying CFAST10 with primers ag467 and ag313 and assembling with plasmid amplified with ag311 and ag314. The genes encoding bJun-NFAST (bJun GenBank accession number: NM_021835.3) and bFos-CFAST11 (bFos GenBank accession number: M34001.1) were synthesized by EUROFINS® genomics. The plasmid pAG384 was cloned by GIBSON ASSEMBLY® by amplification of the gene encoding bFos-CFAST11 (using primers ag541/542), and the backbone of pAG104 (using primers ag358/ag313 and ag347/314). The plasmid pAG385 was generated by amplifying the gene coding for bJun-NFAST using primers ag543/544, followed by a GIBSON ASSEMBLY® with the sequence of mCherry amplified with ag545/546, the primer ag535 for NLSx3 and the backbone of pAG104 amplified using the primers ag358/313 and ag539/ag314.

Protein Expression and Purification

Expression vectors were transformed in Rosetta (DE3) pLysS *E. coli* (NEW ENGLAND BIOLABS®). Cells were grown at 37° C. in LB medium complemented with 50 μg/mL kanamycin and 34 μg/mL chloramphenicol to $OD_{600\ nm}$ 0.6. Expression was induced for 4 hours by adding isopropyl β-D-1-thiogalactopyranoside (IPTG) to a final concentration of 1 mM. Cells were harvested by centrifugation (4,000×g for 20 min at 4° C.) and frozen. The cell pellet was resuspended in lysis buffer (phosphate buffer 50 mM, NaCl 150 mM, $MgCl_2$ 2.5 mM, protease inhibitor, DNase, pH 7.4) and sonicated (5 min at 20% of amplitude, 3 sec on, 1 sec off). The lysate was incubated for 2 hours at 4° C. to allow DNA digestion by DNase. Cellular fragments were removed by centrifugation (9200×g for 1 hour at 4° C.). The supernatant was incubated overnight at 4° C. under gentle agitation with Ni-NTA agarose beads in phosphate buffered saline (PBS) (sodium phosphate 50 mM, NaCl 150 mM, pH 7.4) complemented with 10 mM imidazole. Beads were washed with 20 volumes of PBS containing 20 mM imidazole, and with 5 volumes of PBS complemented with 40 mM imidazole. His-tagged proteins were eluted with 5 volumes of PBS complemented with 0.5 M imidazole. The buffer was exchanged to PBS (50 mM phosphate, 150 mM NaCl, pH 7.4) using PD-10 desalting columns.

Physico-Chemical Measurements

Steady state UV-Vis absorption spectra were recorded using a Cary 300 UV-Vis spectrometer (AGILENT TECHNOLOGIES®), equipped with a Versa20 Peltier-based temperature-controlled cuvette chamber (Quantum Northwest) and fluorescence data were recorded using a LPS 220 spectrofluorometer (PTI, Monmouth Junction, NJ), equipped with a TLC50™ Legacy/PTI Peltier-based temperature-controlled cuvette chamber (Quantum Northwest).

Thermodynamic dissociation constants for NFAST:CFASTn (n=8 to 11) couples were determined using peptides synthesized for CFASTn (n=8 to 11) and recombinantly purified NFAST. The affinity for NFAST:CFAST11 in the presence of 10 μM HMBR was determined independently from a minimum of three different purifications of NFAST. NFAST:CFAST11 was then run in parallel as an internal control for the determination of the other NFAST-CFAST combinations, which were all performed on the same day with the same preparation of NFAST. Thermodynamic dissociation constants were determined with a Spark 10M plate reader (TECAN®) and fit in Prism 6 to a one-site specific binding model.

Mammalian Cell Culture

HEK 293T cells were cultured in Dulbecco's Modified Eagle Medium (DMEM) supplemented with phenol red, GLUTAMAX® I, and 10% (vol/vol) fetal calf serum (FCS), at 37° C. in a 5% CO2 atmosphere. HeLa cells were cultured in Modified Eagle Medium (MEM) supplemented with phenol red, 1× non-essential amino acids, 1× sodium pyruvate, and 10% (vol/vol) fetal calf serum at 37° C. in a 5% CO2 atmosphere. For imaging, cells were seeded in μDish IBIDI® (Biovalley) coated with poly-L-lysine. Cells were transiently transfected using GENEJUICE® (MERCK®) or LIPOFECTAMINE® 2000 (INVITROGEN®) according to the manufacturer's protocol for 24 hours prior to imaging.

Fluorescence Microscopy

Confocal micrographs were acquired on a ZEISS® LSM 710 Laser Scanning Microscope equipped with a Plan Apochromat 63×/1.4 NA oil DIC M27 immersion objective, heated stage, and XL-LSM 710 S1 incubation chamber for temperature and CO2 control. Images were acquired using ZEN software and processed in Fiji (ImageJ).

Photobleaching measurements for HMBR were carried out at 10 μM fluorogen at 488 nm excitation (4.6 kW/cm2, 1.27 psec pixel dwell); FAST was used as a control. Samples were imaged continuously for 1000 images at a 1 frame per second frequency.

To image the rapamycin-mediated interaction between FRB and FKBP, the cells were imaged in DMEM without phenol red supplemented with 5 µM HMBR or 10 µM HBR-3,5DOM. Tile images were taken before rapamycin addition. A solution of rapamycin, prepared in fluorogen-containing DMEM in order to maintain fluorogen concentration constant, was added to obtain a final rapamycin concentration of 100 nM and images were taken every minute. A final tile image was taken after fluorescence saturation.

To image the AP1510-mediated interaction, AP1510 was added to a final concentration of 100 nM to the cells for 2 hours before imaging. The cells were rinsed and the media was replaced with DMEM without phenol red, supplemented with 5 µM HMBR or 10 µM HBR-3,5DOM. Tile images were taken before rapamycin addition. A solution of rapamycin (prepared in DMEM supplemented with fluorogen in order to maintain fluorogen concentration constant) was added to obtain a final rapamycin concentration of 1 µM and images were taken every 30 seconds. A final tile image was taken after fluorescence ceased changing.

To image the association and dissociation of FKBP-FKBP in the same sample, optiMEM (GIBCO®) was supplemented with 5 µM HMBR and AP1510 was added to a final concentration of 100 nM just before the beginning of imaging. The cells were maintained at 37° C. and 5% CO2 over the duration of the experiment. Images were taken every 5 minutes until the fluorescence signal saturated. The acquisition was then paused and the sample was washed with 1×DPBS (supplemented with HMBR in order to maintain fluorogen concentration constant) and the imaging solution was replaced. The acquisition frequency was reduced to 2 images per minute and 7-10 images were acquired before a solution of rapamycin, prepared in optiMEM (supplemented with HMBR in order to maintain fluorogen concentration constant), was added to obtain a final rapamycin concentration of 1 µM.

To image interactions in the Raf-MEK-ERK pathway, the cells were serum-starved for 24 hours before imaging after transfection. The cells were imaged in DMEM without phenol red supplemented with 10 µM HMBR. For time course experiments, the pathway was activated using purified EGF added to a final concentration of 200 ng/mL.

Calcium imaging was performed in HHBSS (HEPES-Buffered Hanks Balanced Salt Solution) supplemented with 5 µM HMBR. Calcium oscillations were triggered using 50 µM histamine in HHBSS (supplemented with HMBR in order to maintain fluorogen concentration constant) and images were acquired every 500 ms.

To image caspase activity, the cells were imaged at 37° C. in 5% CO2 in optiMEM supplemented with 5 µM HMBR. Just before the start of acquisition, staurosporine was added to a final concentration of 2 µM. Images were acquired every 5 minutes over 3 hours.

Influence of the Length of CFAST on in-Cell Brightness of Complexes

HEK 293T cells were seeded in ibidi µDish microscopy dishes and 24 hours prior to imaging were co-transfected with plasmids encoding CMV-FRB-NFAST (or NFAST (V107I))-P2A-mCherry (or EGFP)) and CMV-FKBP-CFASTn (n=11, 10 or 9). The cells were imaged before and after addition of 500 nM rapamycin.

Evaluation of Split Site Efficiency in *E. coli*

The de novo designed peptides IAAL-E3 and IAAL-K3 form antiparallel alpha helical coiled coils that interact constitutively with an affinity of 70 nM. The interacting system was expressed in a bis-cistronic vector with two T7 promoters for simultaneous expression in *E. coli*. The genes encoding IAAL-E3-CFAST(65-125)-T7p-NFAST(1-64)-IAAL-K3, IAAL-K3_NFAST(1-64)-T7p-CFAST(65-125)-IAAL-E3, IAAL-E3-CFAST(115-125)-T7p-NFAST(1-114)-IAAL-K3, IAAL-K3_NFAST(1-114)-T7p-CFAST (115-125)-IAAL-E3 were purchased (EUROFINS® genomics) and inserted using the restriction enzymes Nco I and Xho I into the plasmid, pET28a. The resulting plasmids were transformed into *E. coli* BL21 Rosetta cells. Overnight pre-cultures were used into inoculate 5 mL cultures, which were then grown to OD ~0.6 and induced with 1 mM IPTG for two hours. The cytometry samples were prepared using 1.5 mL of culture that was pelleted and then washed in 1×PBS+BSA (1 g/L). The samples were then resuspended in 1.5 mL PBS+BSA with HMBR and 50,000 events were analyzed on a BD ACCURI® c6 cytometer.

Example 1: Generation of the Split-FAST Fluorescence Complementation System

The complementation system split-FAST (FIG. 1A) was engineered from the PYP-derived Fluorescence-Activating and absorption Shifting Tag (FAST—amino acid sequence SEQ ID NO: 9), a small protein of 14 kDa that specifically and reversibly binds fluorogenic hydroxybenzylidene rhodanine (HBR) analogs displaying various spectral properties. Fluorogenic HBR analogs are weakly fluorescent in solution but strongly fluoresce when immobilized in the binding cavity of FAST. The design is based on the splitting of FAST in two fragments between amino acids 114 and 115 (FIG. 1B). The two fragments 1-114 (hereafter called NFAST—SEQ ID NO: 23) and 115-125 (hereafter called CFAST11—SEQ ID NO: 34) showed modest affinity in presence of HMBR (which provides green-yellow fluorescence) or HBR-3,5DOM (which provides orange-red fluorescence). The apparent affinity of the two fragments could be further decreased by the successive removal of residues at the C terminus of CFAST11, resulting in CFAST10—SEQ ID NO: 42; CFAST9—SEQ ID NO: 43 and CFAST8—SEQ ID NO: 44 (Table 3).

TABLE 3

| affinities of the split fragments in the presence of fluorogens | | |
| --- | --- | --- |
| CFASTn | $K_D$ of NFAST-CFASTn 10 µM HMBR | $K_D$ of NFAST-CFASTn 10 µM HBR-3,5-DOM |
| CFAST11 | 0.21 ± 0.05 | 1.4 ± 0.2 |
| CFAST10 | 0.95 ± 0.08 | 6.2 ± 0.5 |
| CFAST9 | 5.7 ± 0.06 | 25 ± 1 |
| CFAST8 | 21 ± 4 | Not determined |

Figures 2A, 2B, 2C:
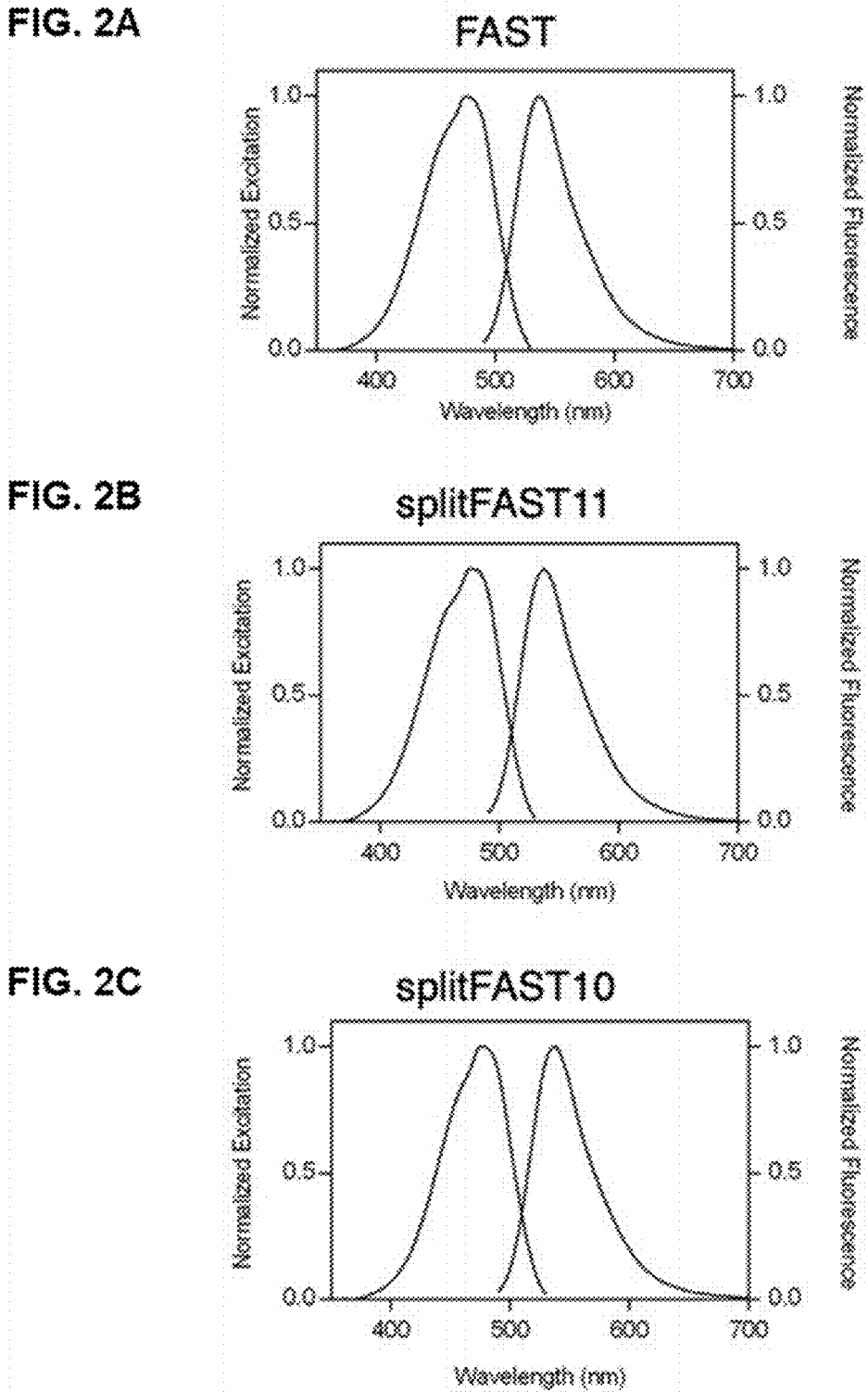
FIGS. 2A-2C are a set of graphs showing the normalized excitation and emission spectra of complexes formed of either FAST or split-FAST and the fluorogenic HBR analog HMBR: FAST:HMBR (2A), splitFAST11:HMBR (2B), and splitFAST10:HMBR (2C). split-FAST11 results from the complementation of NFAST and CFAST11; split-FAST10 results from the complementation of NFAST and CFAST10.

As shown in FIG. 2, the excitation and emission spectra of the complemented split-FAST:fluorogen assembly (resulting from the complementation of NFAST and CFAST11 (FIG. 2B), and of NFAST and CFAST10 (FIG. 2C)) were identical to those of the regular FAST:fluorogen complex (FIG. 2A).

The results of FIG. 2 thus demonstrate that, once complemented, the complementation system of the invention behaves as the full-length FAST in terms of binding of fluorogenic HBR analogs, induction of fluorescence following said binding and photophysical properties. The complementation system of the invention thus allows the reconstitution of a functional PYP (e.g., split-FAST11), or a functional truncated fragment thereof (e.g., split-FAST10).

Figures 3A, 3B, 3C, 3D:
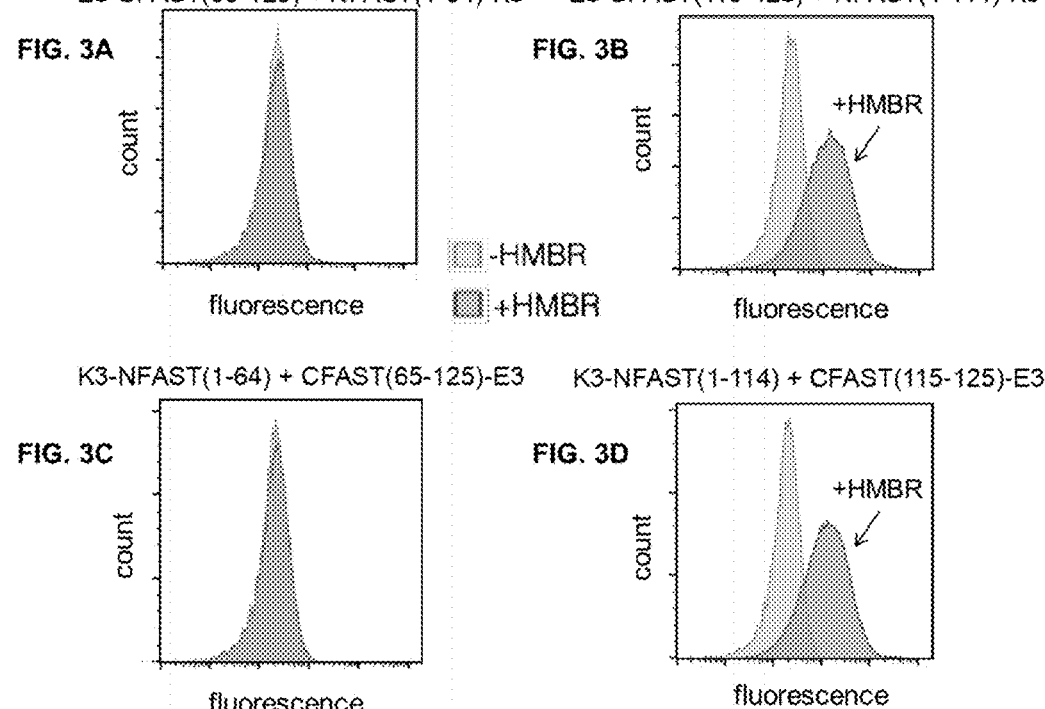
FIGS. 3A-3D are a set of graphs showing the flow cytometry analysis of *E. coli* cells expressing the indicated fusion proteins in absence or presence of the fluorogenic HBR analog HMBR: E3-CFAST(65-125)+NFAST(1-64)— K3 (3A), E3-CFAST(115-125)+NFAST(1-114)—K3 (3B), K3-NFAST(1-64)+CFAST(65-125)-E3 (3C), and K3-NFAST(1-114)+CFAST(115-125)-E3 (3D). K3 and E3 are two proteins interacting with high affinity.

The design of the fluorescence complementation system of the invention was validated by comparing the fluorescence intensity obtained in *E. coli* cells when a pair of proteins interacting with high affinity (i.e., E3 and K3) were fused to different fragments of the PYP-derived FAST (FIG. 3). A first PYP fragment, i.e., NFAST, was fused to K3 and a second PYP fragment, i.e., CFAST, was fused to E3. FAST was split in two fragments between amino acids 114 and 115 and the resulting fragments FAST1-114 (i.e., NFAST) and FAST115-125 (i.e., CFAST11) were fused to K3 and E3, respectively (either NFAST-K3 or K3-NFAST, and E3-CFAST or CFAST-E3). The combinations of either NFAST-K3 and E3-CFAST11 (FIG. 3B) or K3-NFAST and CFAST11-E3 (FIG. 3D) led to an increase in fluorescence intensity in the presence of HMBR compared to the fluorescence intensity obtained without HMBR. By contrast, when FAST was split in two fragments between amino acids 64 and 65 and the resulting fragments FAST1-64 and FAST65-125 were fused to K3 or E3, no such increase was observed for any of the combinations tested (FIG. 3A & 3C).

An alternative N-terminal fragment was also developed using a variant of FAST (referred to as improved FAST or iFAST—amino acid sequence SEQ ID NO: 16), wherein the valine at position 107 is replaced by an isoleucine. Using different fluorogenic HBR analogs, the relative in-cell brightness of various split-FAST was assessed (FIG. 4).

As shown in FIG. 4, with any of the fluorogenic HBR analogs tested: HMBR (FIG. 4A), HBR-3,5DM (FIG. 4B), HBR-30M (FIG. 4C) and HBR-3,5DOM (FIG. 4D), the fluorescence observed was highest with CFAST11, lower with CFAST10 and lowest with CFAST9. The lower affinity between the two fragments (see Table 3 above) coincides with a lower in-cell brightness.

As shown in FIG. 4, the fluorescence observed with a system comprising NFAST (SEQ ID NO: 23) and CFAST is similar to that observed with a system comprising the corresponding Nter fragment of iFAST (SEQ ID NO: 30) and CFAST. These data thus demonstrate the suitability of iFAST in a complementation system according to the invention.

Example 2: Split-FAST Allows the Characterization of Dynamic and Reversible Protein Interactions To test the ability of split-FAST to detect protein interactions in mammalian cells (pretreated with fluorogenic HBR analogs), NFAST and CFASTn (n=10 or 11) were fused to the FK506 binding protein (FKBP) and to the FKBP-rapamycin binding domain of mTOR (FRB), respectively. FKBP and FRB interact together in the presence of rapamycin.

Figures 5A, 5B, 5C, 5D, 5E:
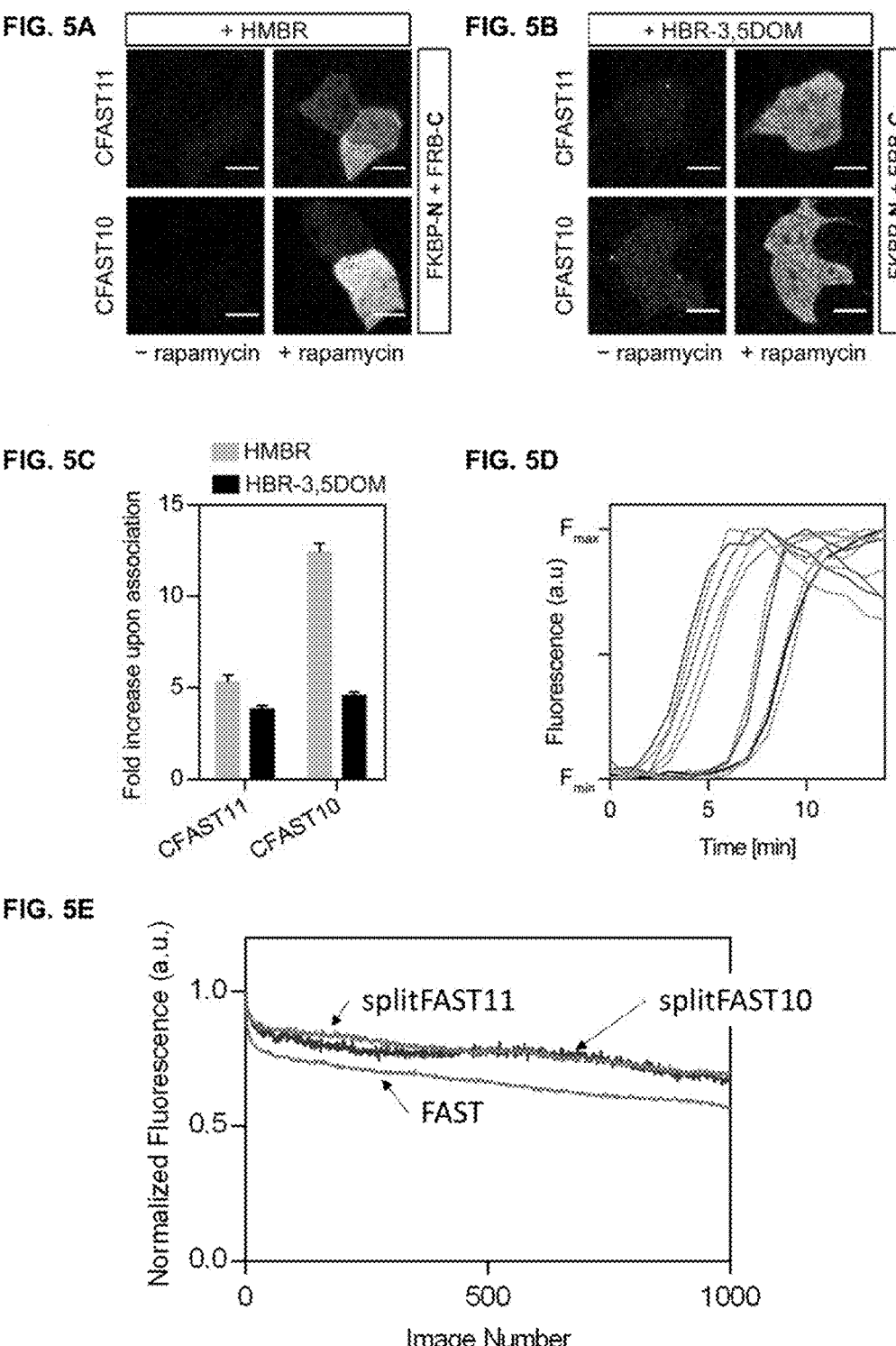
Figures 7A, 7B:
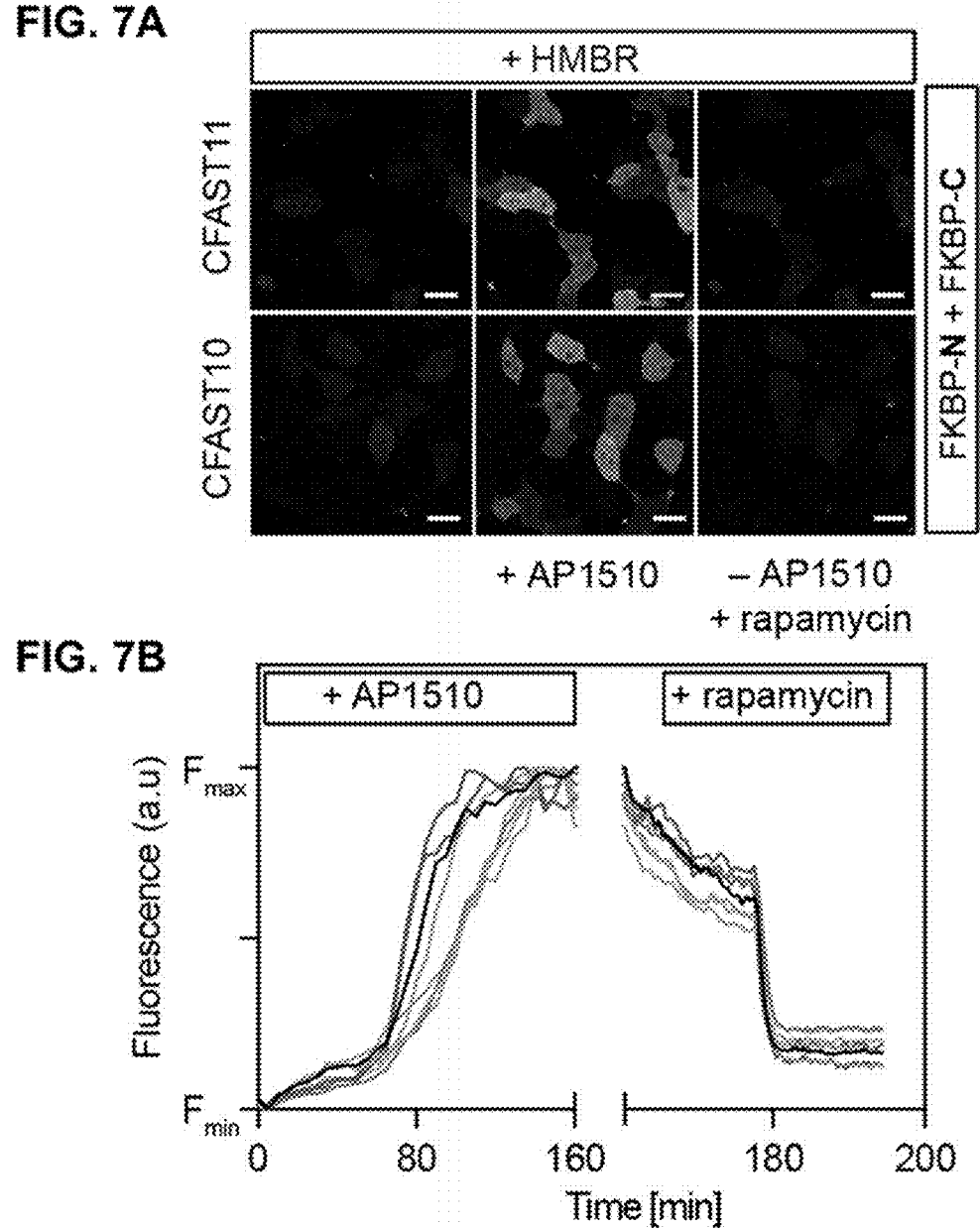
FIGS. 7A-7D illustrate the detection of the dimerization of FKBP-FKBP homodimer and the dissociation of said FKBP-FKBP homodimer with the complementation system of the invention. 7A shows HMBR-labeled cells co-expressing FKBP-NFAST and FKBP-CFASTn (n=11 or 10) which were first treated with 100 nM AP1510 for 160 min, then AP1510 was removed, and 1 μM rapamycin was added. Selected frames are shown, scale bars: 30 μm. 7B shows the temporal evolution of the fluorescence intensity upon sequential treatment of HMBR-labeled cells co-expressing FKBP-NFAST and FKBP-CFAST11 with AP1510 and then rapamycin (n=8 cells). 7C and 7D show HMBR-labeled cells co-expressing FKBP-NFAST and FKBP-CFASTn (n=11 (7C) or n=10 (7D)) which were first treated with 100 nM AP1510 for 160 min (association phase), then AP1510 was removed, and 1 μM rapamycin was added (dissociation phase). Selected frames are shown, scale bars 30 μm.
Figures 7C, 7D:
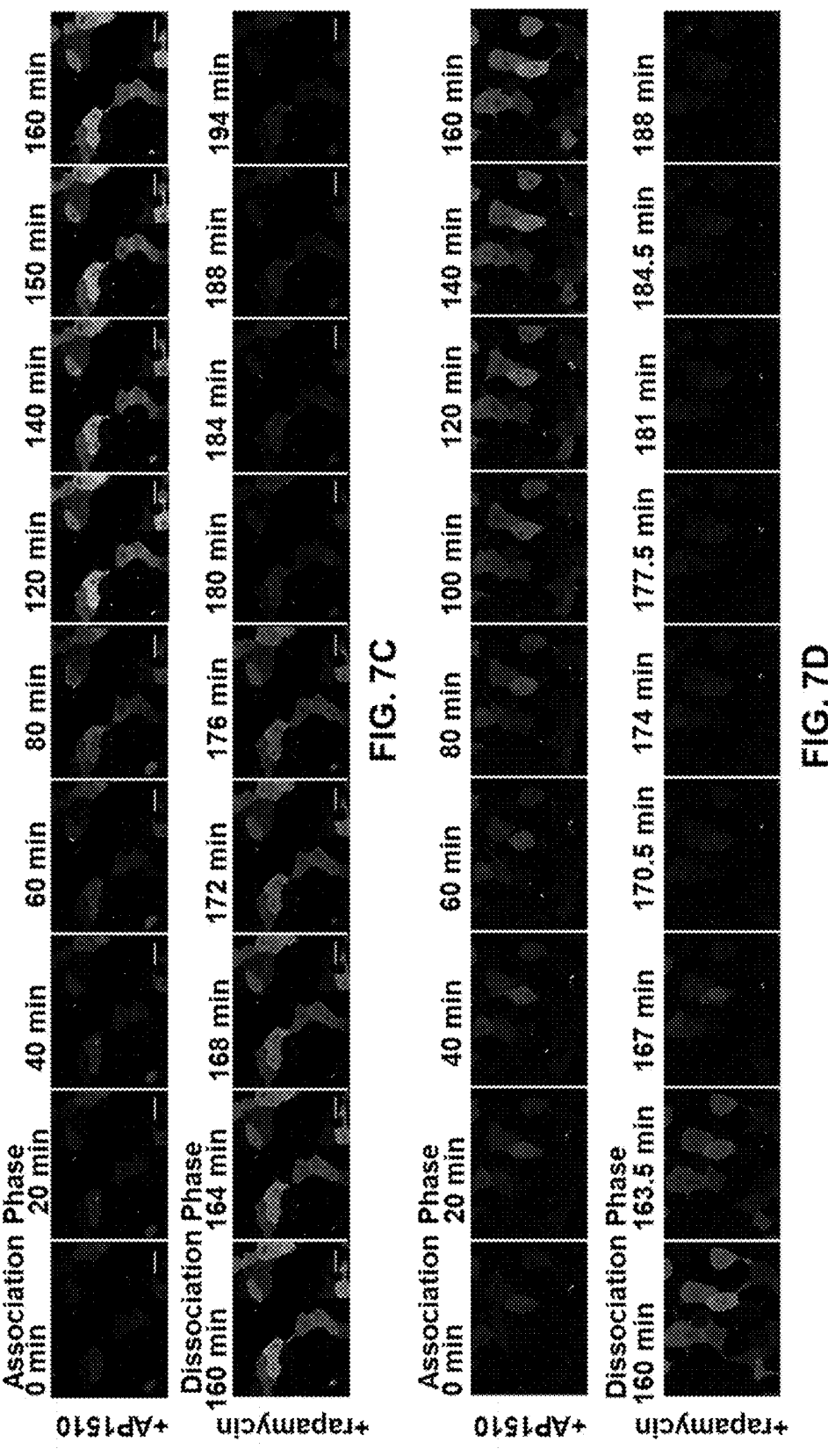

As shown in FIG. 5, rapamycin-induced FRB-FKBP dimerization led to a large fluorescence increase, in accordance with interaction-dependent complementation of split-FAST. The use of either HMBR or HBR-3,5DOM gave similar results (FIG. 5A-C), demonstrating that the color of split-FAST can be tuned by changing the nature of the fluorogen added.

Time lapse imaging after rapamycin addition showed fluorescence saturation within a few minutes, in agreement with the rapid formation of the FRB-FKBP-rapamycin complex (FIGS. 5D, F and G). These results thus demonstrate that split-FAST can monitor protein complex formation in real-time. In cells, split-FAST:fluorogen assemblies (with either CFAST11 or CFAST10) were furthermore shown to be as photostable as the regular FAST:fluorogen complex (FIG. 5E).

The ability of rapamycin to dissociate AP1510-induced FKBP homodimers was used to test the reversibility of split-FAST. Cells co-expressing FKBP-NFAST and FKBP-CFASTn (n=10 or 11) were incubated with AP1510 for two hours to pre-form FKBP homodimers and treated with HMBR. Addition of rapamycin led to a significant loss of split-FAST:fluorogen fluorescence in agreement with FKBP homodimer dissociation (FIG. 6A-C). These results thus demonstrate that the split-FAST:fluorogen assembly is reversible. Rapid loss of fluorescence within a few minutes was observed after rapamycin addition, demonstrating the rapid disassembly of split-FAST when two proteins dissociate (FIGS. 6D, E and F). The ability of split-FAST to image dynamic and reversible protein interactions was further demonstrated by monitoring in a single experiment, first, the association of FKBP-NFAST and FKBP-CFASTn (n=11 or 10) upon addition of AP1510, and then, the dissociation of the FKBP-FKBP homodimer by removal of AP1510 and addition of rapamycin (FIG. 7A-D).

In conclusion, the data presented hereinabove demonstrate that split-FAST is a reversible complementation system that allows the real-time monitoring of both the association and the dissociation of proteins of interest. Moreover, the NFAST and CFAST fragments are characterized by a low affinity, resulting in a limited self-assembly and thus in a low unspecific fluorescence background.

Figures 8A, 8B:
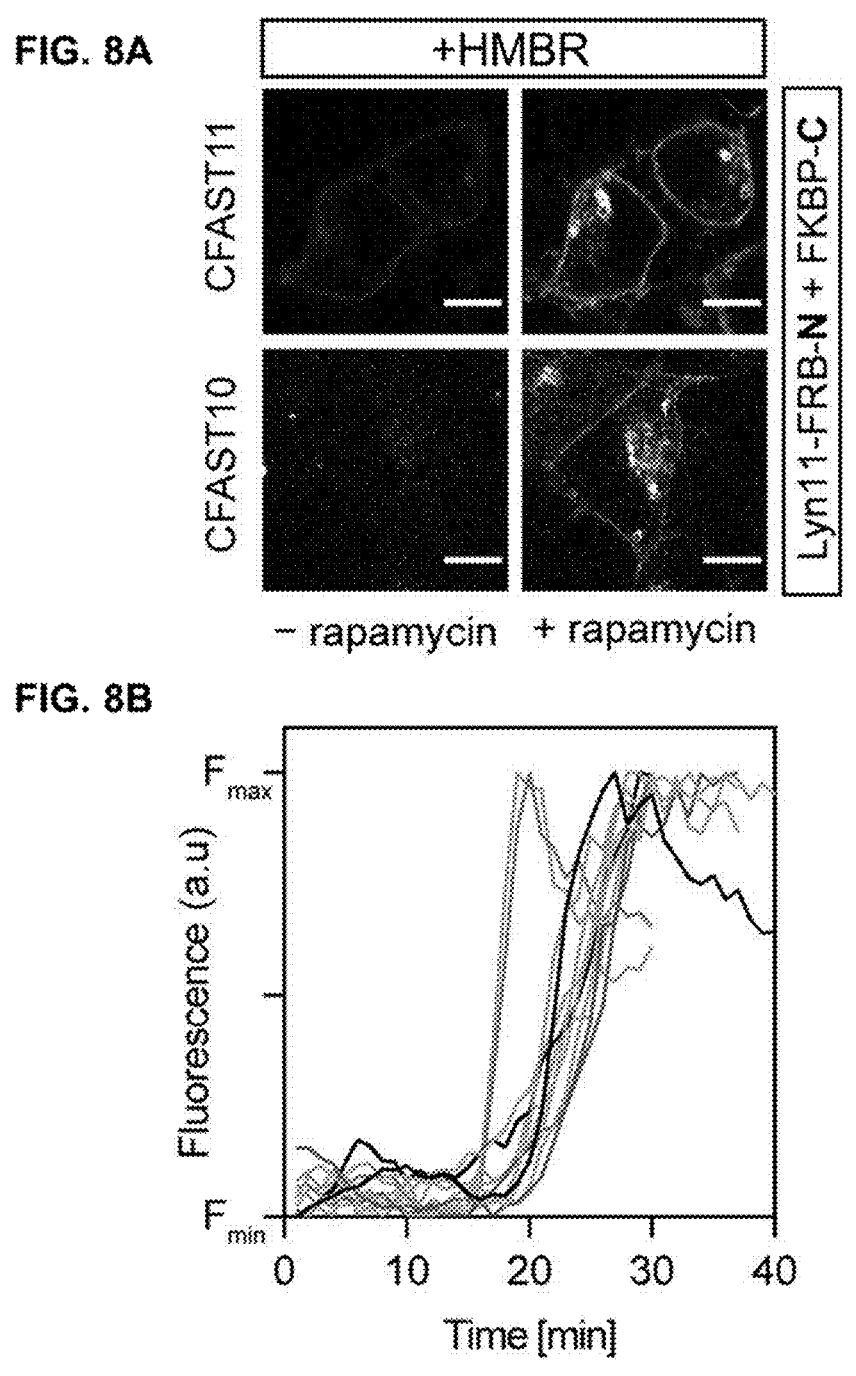

Example 3: Split-FAST Allows the Detection of the Interaction Between a Membrane Protein and a Cytosolic Protein As many protein interactions occur at the plasma membrane, the use of split-FAST to detect the interaction between a membrane protein and a cytosolic protein was next tested. FKBP-CFASTn (n=11 or 10) was expressed in the cytosol and FRB-NFAST at the plasma membrane using a Lyn11 membrane-anchoring sequence (Lyn11-FRB-NFAST). Addition of rapamycin led to the rapid formation of fluorescent split-FAST:fluorogen assemblies at the plasma membrane in HMBR-treated cells (FIG. 8A-B), demonstrating the ability of split-FAST to detect proteins interactions at the plasma membrane in real-time.

Figure 9:
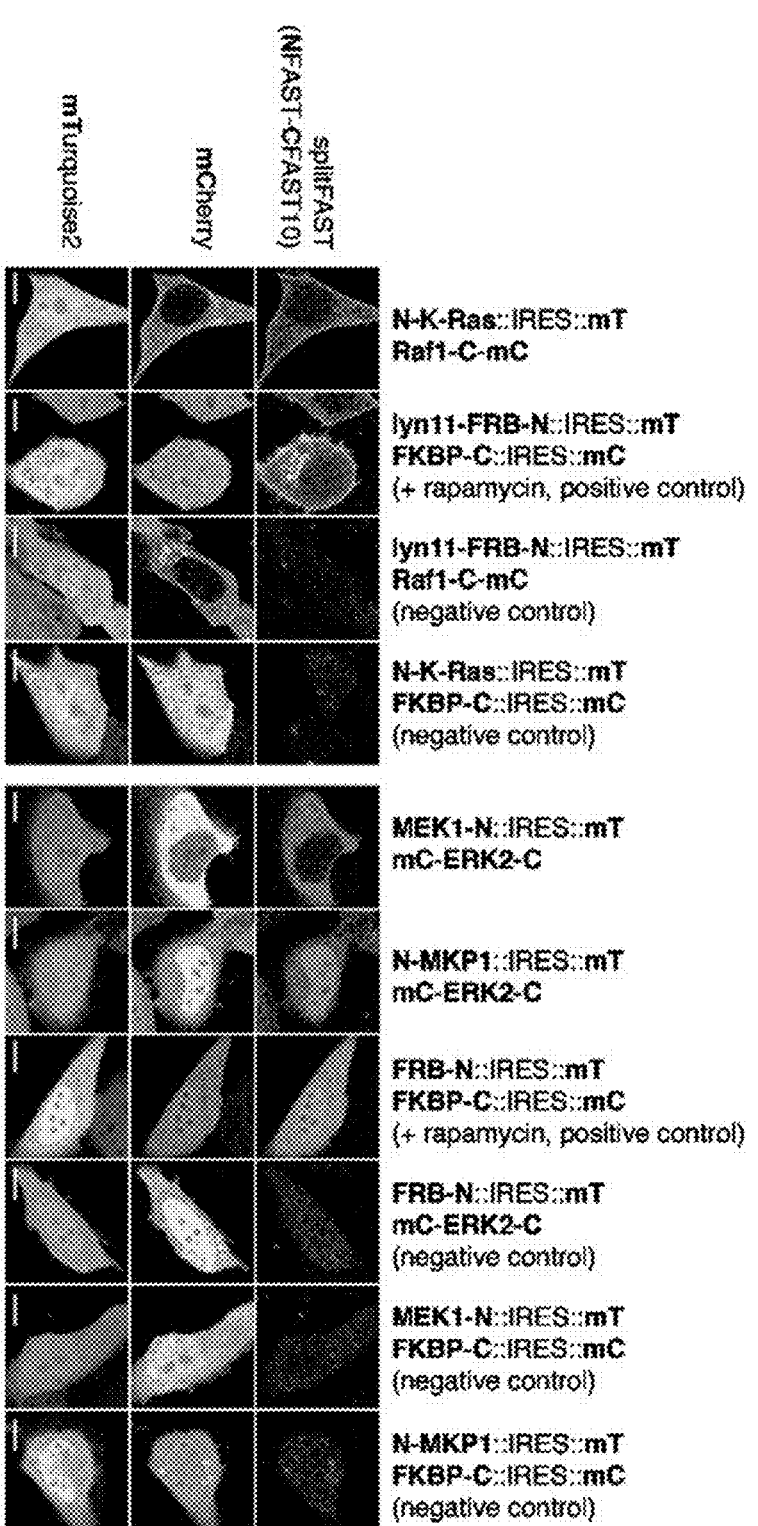
FIGS. 9A-9D are a set of images illustrating the use of split-FAST for imaging K-Ras/Raf1 (9A), MEK1/ERK2 (9B) and ERK2/MKP1 (9C) interactions. Representative images of cells co-expressing the indicated constructs were imaged in presence of 10 μM HMBR. Scale bar 20 μm. 9D shows controls relating to the use of split-FAST for imaging K-Ras/Raf1, MEK1/ERK2 and ERK2/MKP1 interactions. Representative cells co-expressing the indicated constructs were imaged in presence of 10 μM HMBR. Positive and negative controls are shown. Scale bars 10 μm. Split-FAST corresponds to the reconstituted functional PYP, i.e., FAST, resulting from the complementation of the two FAST fragments, NFAST and CFAST10.

Example 4: Split-FAST Enables the Observation of Dynamic Protein Interactions in a Signaling Pathway in Real Time Split-FAST was then benchmarked with known, physiologically relevant protein interactions from the mitogen-activated protein kinase (MAPK) signaling pathway. NFAST was fused to K-Ras, a small GTPase downstream of growth factor receptors, and CFAST10 was fused to an mCherry fusion of Raf1, known to be recruited to the membrane by interaction with K-Ras. The fluorescence of split-FAST:HMBR was colocalized with that of mCherry and concentrated at the membrane, in agreement with a specific recruitment of Raf1 at the plasma membrane by K-Ras (FIG. 9A). Next, the interaction between the MAP kinase kinase MEK1, and the downstream extracellular signal-regulated protein kinase ERK2, one of the central interactions in the Raf/MEK/ERK signaling pathway was assessed using split-FAST. When MEK1 was fused to NFAST (MEK1-NFAST) and a mCherry fusion of ERK2 was fused to CFAST10 (mCherry-ERK2-CFAST10), a specific, cytosolic split-FAST:HMBR fluorescence was observed in accordance with MEK1 anchoring ERK2 in the cytosol (FIG. 9B). Finally, split-FAST allowed to detect the nuclear interaction between ERK2 and MKP1 (DUSP1), which is a phosphatase localized in the nucleus responsible for deactivating ERK2 after its activation and subsequent translocation to the nucleus (FIG. 9C). Controls relating to the use of split-FAST for imaging the K-Ras/Raf1, MEK1/ERK2 and ERK2/MKP1 interactions are shown in FIG. 9D.

Figure 10A:
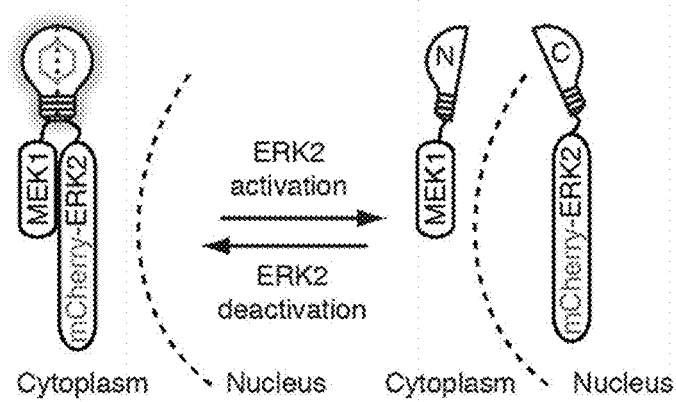
FIGS. 10A and 10B illustrate the use of split-FAST for imaging the evolution of MEK1/ERK2 interaction upon EGF stimulation. HMBR-labeled Hela cells co-expressing MEK1-NFAST and mCherry-ERK2-CFAST10 were imaged after stimulation with EGF. 10A depicts the experimental design. N and C represent the first and second PYP fragments according to the invention, respectively, able to interact and thus to reconstitute a functional PYP that can reversibly bind a fluorogen and turn on its fluorescence. 10B shows the temporal evolution of split-FAST fluorescence, cytoplasmic mCherry fluorescence and nuclear mCherry fluorescence intensities (mean±sem, n=6 cells, 5 experiments). Data were synchronized using the beginning of the nuclear import of mCherry-ERK2-CFAST10 as reference.
Figure 10B:
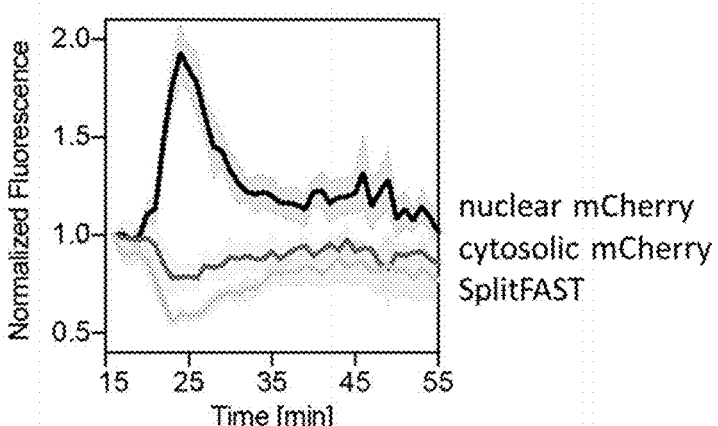

To explore the applicability of split-FAST to study dynamic protein interactions, interaction between MEK1 and ERK2 upon activation of the MAPK signaling pathway was followed. Upon cell stimulation, MEK1 phosphorylates ERK2, which detaches from MEK1 and translocates to the nucleus, where it regulates the activity of transcription factors. Dephosphorylation by nuclear phosphatases deactivates ERK2, returning it to the cytoplasm. In resting HMBR-treated cells expressing MEK1-NFAST and mCherry-ERK2-CFAST10, mCherry and split-FAST:HMBR fluorescence were cytoplasmic, in agreement with MEK1 anchoring ERK2 in the cytoplasm. Upon cell stimulation with epidermal growth factor (EGF), mCherry-ERK2-CFAST10 dissociated from MEK1-NFAST and translocated to the nucleus, as shown by the simultaneous loss of split-FAST:HMBR fluorescence and the nuclear accumulation of mCherry fluorescence. The nuclear accumulation of mCherry-ERK2-CFAST10 was transitory: desensitized mCherry-ERK2-CFAST10 returned to the cytoplasm and re-assembled with MEK1-NFAST, as revealed by the simultaneous increase of split-FAST:HMBR fluorescence and cytosolic mCherry fluorescence (FIG. 10A-B).

This experiment illustrates how split-FAST can be used to observe dynamic protein interactions in signaling pathways in real-time.

Figure 11A:
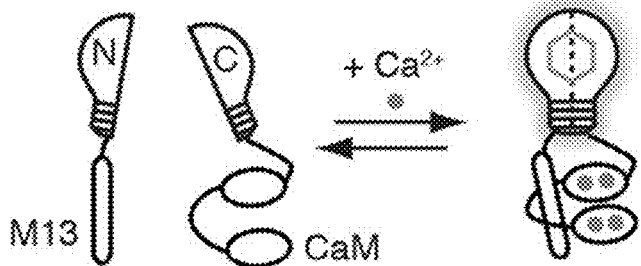
FIGS. 11A and 11B illustrate the use of split-FAST for imaging of the Ca$^{2+}$-dependent interaction of calmodulin (CaM) and the Ca$^{2+}$-CaM-interacting peptide M13. 11A depicts the experimental design. N and C represent the first and second PYP fragments according to the invention (NFAST and CFAST10, respectively) able to interact and thus to reconstitute a functional PYP that can reversibly bind a fluorogen and turn on its fluorescence. The sensor is composed of M13-NFAST and CFAST10-CaM. 11B shows the temporal evolution of the intracellular fluorescence intensity for a representative HMBR-treated HeLa cell (n=14 cells from 2 experiments) treated with histamine (histamine addition is shown by the arrow).
Figure 11B:
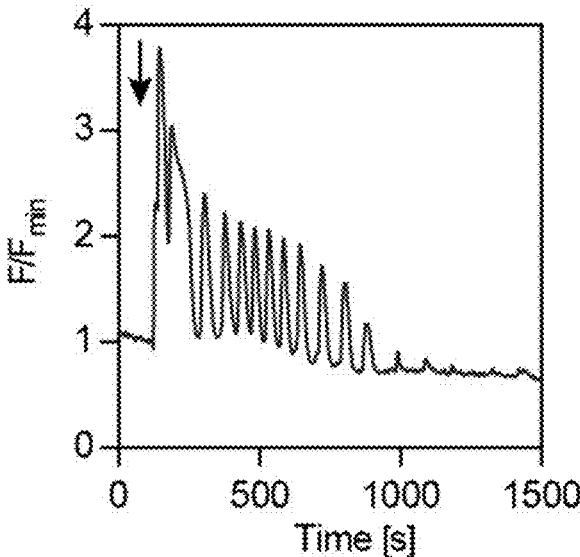
Figure 13A:
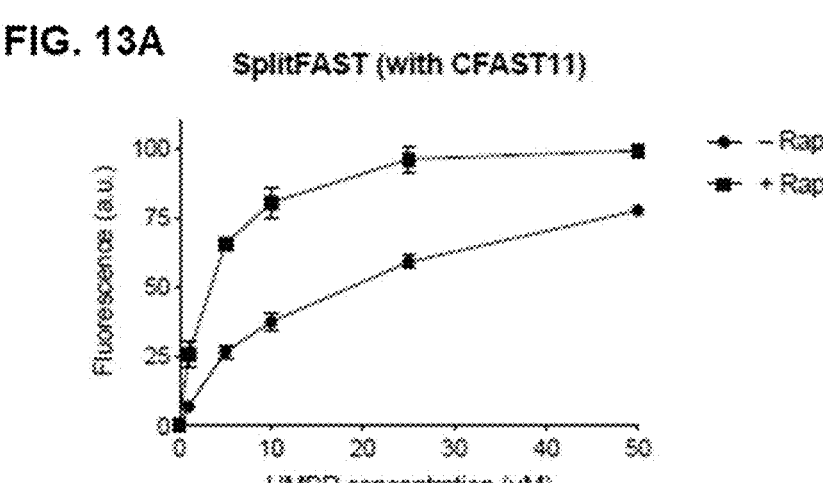
FIGS. 13A and 13I are a combination of graphs illustrating the use of complementation systems comprising PYP fragments of FAST or orthologs of FAST for detecting the rapamycin-induced dimerization of FRB and FKBP. Human embryonic kidney (HEK) 293T cells expressing FRB fused to a N-terminal PYP fragment (i.e., first PYP fragment of the invention) and FKBP fused to a C-terminal PYP fragment (i.e., second PYP fragment of the invention) of different complementation systems according to the present invention were incubated with the fluorogen HMBR at the following concentrations: 0, 1, 5, 10, 25, 50 μM. Cell fluorescence was analyzed in absence and in presence of 500 nM rapamycin by flow cytometry. The graphs show the fluorescence mean of split-FAST (with CFAST11) (13A), split-FAST (with CFAST10) (13B), split-iFAST (13C), O₁-splitFAST derived from *Halomonas boliviensis* LC1 PYP (13D), O₂-splitFAST derived from *Halomonas* sp. GFAJ-1 PYP (13E), O₃-splitFAST derived from *Rheinheimera* sp. A13L PYP (13F), O₄-splitFAST derived from *Idiomarina loihiensis* PYP (13G), O₅-splitFAST derived from *Thiorhodospira sibirica* ATCC 700588 PYP (13H), and O₆-splitFAST derived from *Rhodothalassium salexigens* PYP (13I) at the indicated HMBR concentrations in presence and absence of rapamycin.
Figure 13B:
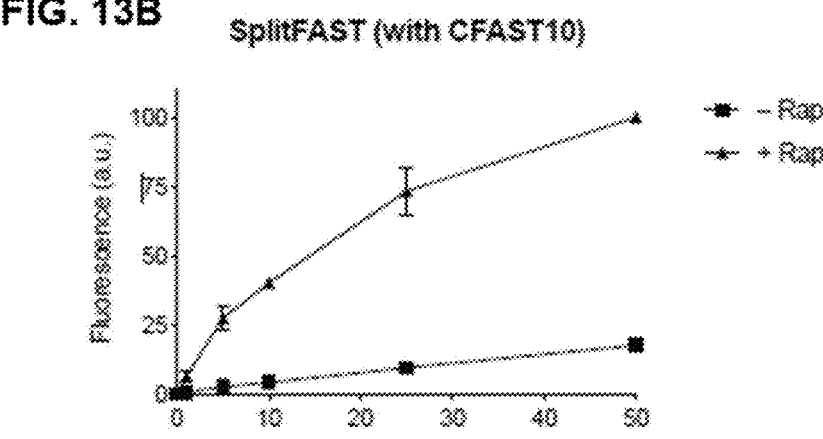
Figure 13C:
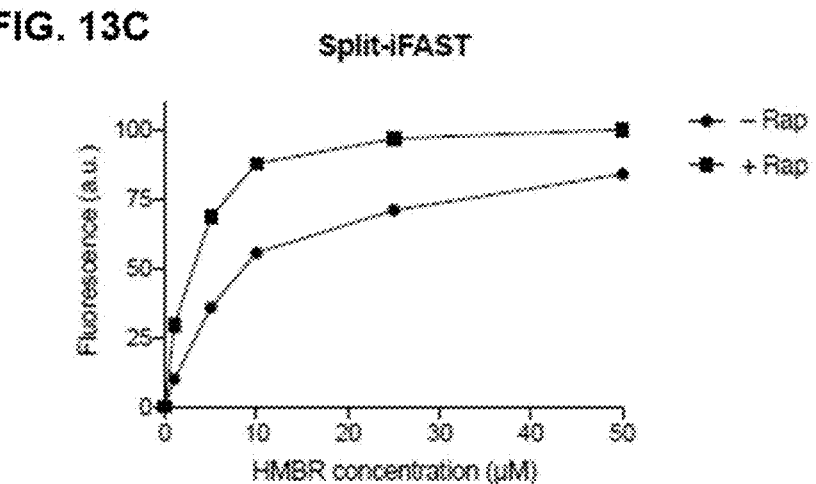
Figure 13D:
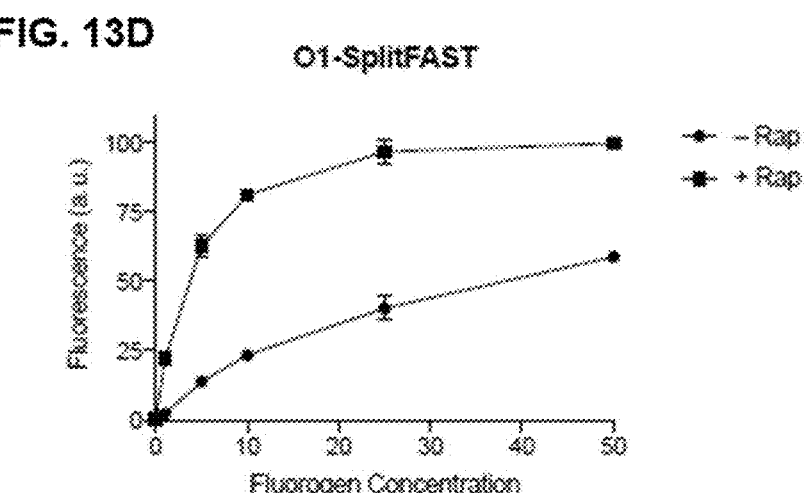
Figure 13E:
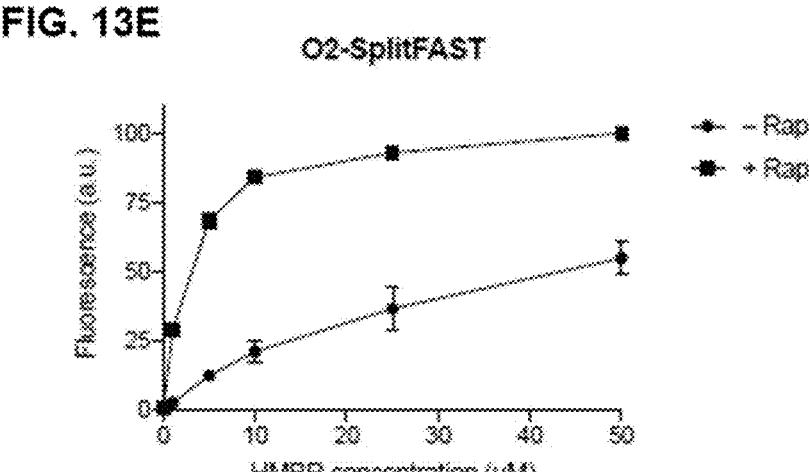
Figure 13F:
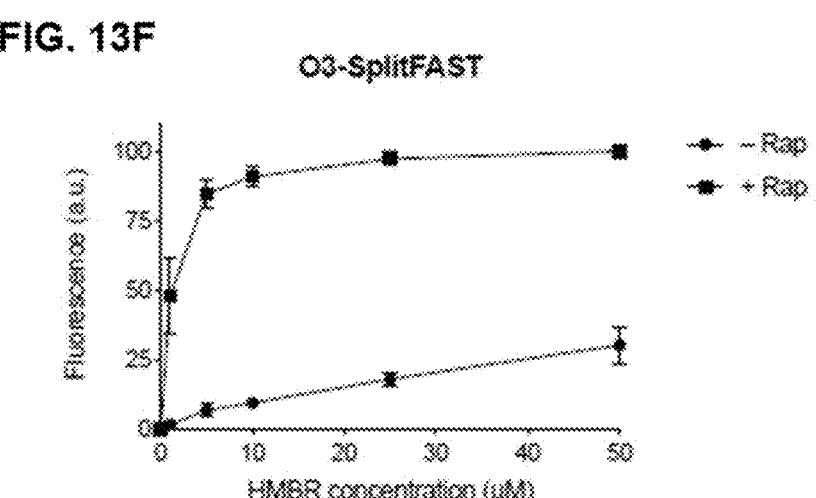
Figure 13G:
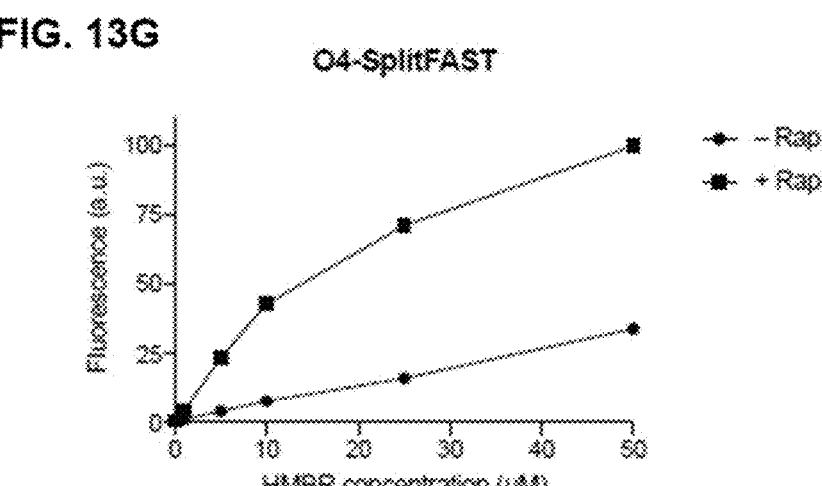
Figure 13H:
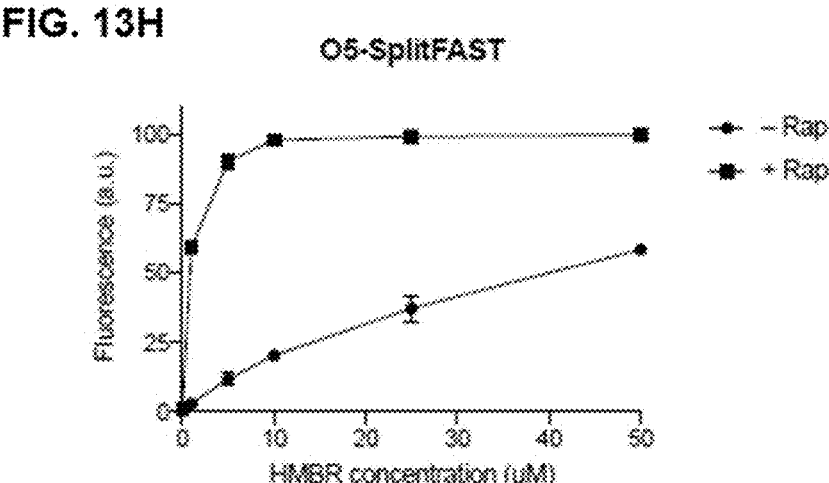
Figure 13I:
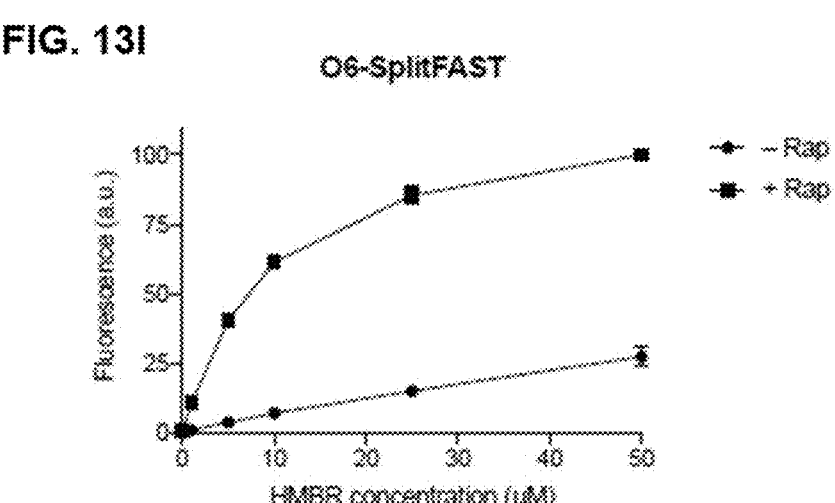

Example 5: Split-FAST Enables the Observation of Transient and Short-Lived Interactions To further demonstrate the use of split-FAST for the detection of rapid and transient interactions, the $Ca^{2+}$-dependent interaction between calmodulin (CaM) and the $Ca^{2+}$-CaM-interacting peptide M13 was monitored. In HMBR-treated HeLa cells expressing CFAST10-CaM and M13-NFAST, addition of histamine led to a large increase of split-FAST-HMBR fluorescence followed by rapid oscillations of the fluorescence signals and eventually desensitization (FIG. 11A-B). This response was in agreement with the known change in $Ca^{2+}$ concentration in mammalian cells upon histamine stimulation, and demonstrated the ability of split-FAST to image transient, short-lived interactions.

Example 6: Split-FAST Enables the Generation of Cellular Sensors

Figures 12A, 12B:
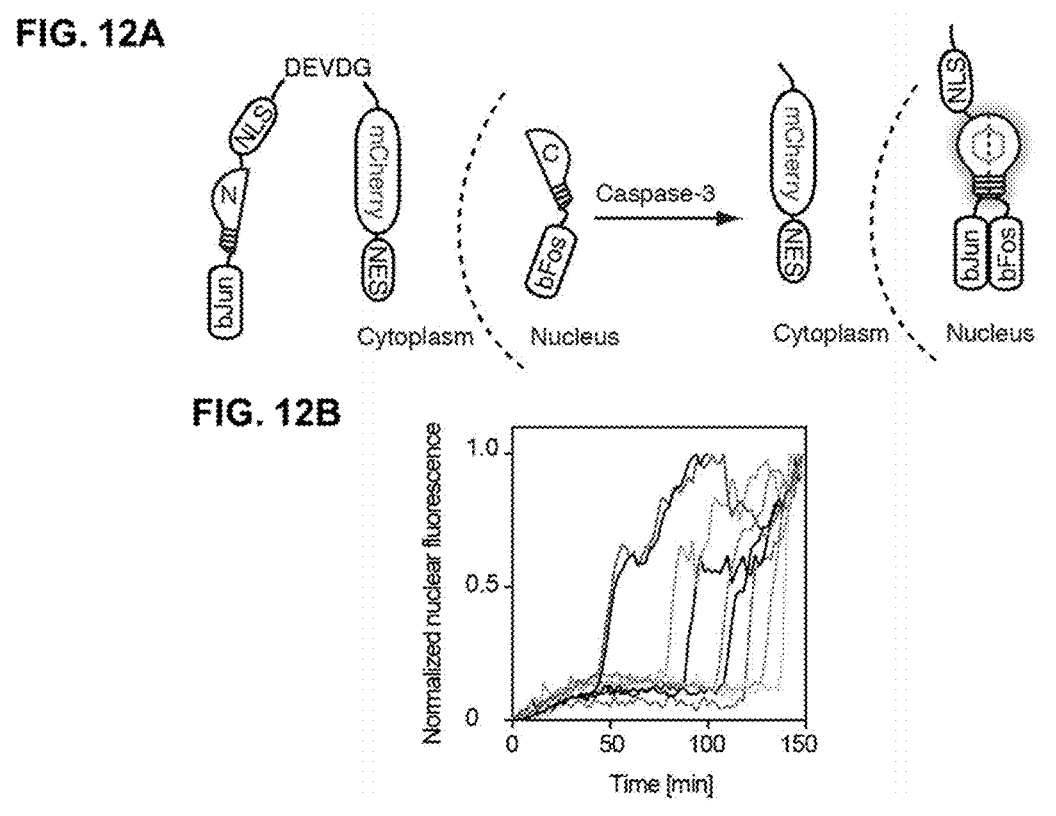

To examine the utility of split-FAST for imaging other signaling processes, a caspase biosensor was created. The transcriptional regulator bFos was fused to CFAST (bFos-CFAST11), and a gene encoding bJun-NFAST-NLS3-DEVDG-mCherry-NES was constructed, where NES is a genetically fused nuclear export signal, DEVD is the caspase-3 substrate sequence Asp-Glu-Val-Asp, NLS is a nuclear localization signal, and bJun is a peptide known to form a heterodimer with bFos (FIG. 12A). Induction of apoptosis (and thus caspase-3 activity) by treatment with staurosporine released bJun-NFAST from mCherry-NES, resulting in the translocation of bJun-NFAST to the nucleus, and the subsequent complementation of split-FAST by interaction of bJun and bFos. Approximately 1-2 hour(s) after the induction of apoptosis, the red fluorescence of mCherry was segregated in the cytoplasm and the bright green fluorescence of complemented split-FAST:HMBR appeared in the nucleus (FIG. 12B). Beyond further demonstrating the potential of split-FAST to monitor protein interactions formation in real-time, this experiment showed the great potential of split-FAST for the design of cellular sensors.

To conclude, the data presented hereinabove demonstrate that split-FAST, a split reporter displaying rapid and reversible complementation, allows one to observe transient protein interactions in real-time. Split-FAST:fluorogen fluoresces green-yellow or orange-red light depending on the fluorogen used, thus providing a system adaptable to multicolor imaging. Split-FAST allows the observation of protein interactions in various cellular compartments (cytosol, nucleus, plasma membrane) and, in contrast to traditional BiFC systems, allows the monitoring of both the formation and dissociation of protein assembly in real-time. This unprecedented behavior can be exploited to study the role and function of protein interactions in various cellular processes and dissect complex interaction networks.

Example 7: Complementation Systems with Orthologs of FAST

FAST, iFAST and 6 functional PYP deriving from the orthologs $O_n$ (n=1-6) were split into two complementary fragments in their last loop between residues 114 and 115 as indicated above. The 6 functional PYP deriving from the orthologs $O_{1-6}$ have an amino acid sequence with at least 70% identity with the amino acid sequence of FAST (SEQ ID NO: 9).

As used hereinafter:

$O_1$ refers to a functional PYP deriving from *Halomonas boliviensis* LC1 PYP and having the sequence set forth in SEQ ID NO: 10;

$O_2$ refers to a functional PYP deriving from *Halomonas* sp. GFAJ-1 PYP and having the amino acid sequence set forth in SEQ ID NO: 11;

$O_3$ refers to a functional PYP deriving from Rheinheimera sp. A13L PYP and having the amino acid sequence set forth in SEQ ID NO: 12;

$O_4$ refers to a functional PYP deriving from *Idiomarina loihiensis* PYP and having the amino acid sequence set forth in SEQ ID NO: 13;

$O_5$ refers to a functional PYP deriving from *Thiorhodospira sibirica* ATCC 700588 PYP and having the amino acid sequence set forth in SEQ ID NO: 14; and $O_6$ refers to a functional PYP deriving from *Rhodothalassium salexigens* PYP and having the amino acid sequence set forth in SEQ ID NO: 15.

The N-terminal fragments (corresponding to residues 1-114) obtained from FAST, iFAST and the 6 orthologs $O_{1-6}$ were called NFAST, N-iFAST and $O_{1-6}$NFAST, respectively. As previously indicated, the NFAST and N-iFAST fragments have the amino acid sequences as set forth in SEQ ID NO: 23 and SEQ ID NO: 30, respectively. $O_{1-6}$NFAST have the amino acid sequences as set forth in SEQ ID NO:24 ($O_1$NFAST), SEQ ID NO: 25 ($O_2$NFAST), SEQ ID NO: 26 ($O_3$NFAST), SEQ ID NO: 27 ($O_4$NFAST), SEQ ID NO: 28 ($O_5$NFAST) and SEQ ID NO: 29 ($O_6$NFAST).

The C-terminal fragments (corresponding to residues 115-125) obtained from FAST and iFAST were identical and called CFAST11, the C-terminal fragments (corresponding to residues 115-125) obtained from the 6 orthologs $O_{1-6}$ were called $O_{1-6}$CFAST. For split-FAST, a truncated C-terminal fragment (residues 115-124, named CFAST10) was also tested. As previously indicated, the CFAST11 and CFAST10 fragments have the amino acid sequences as set forth in SEQ ID NO: 34 and SEQ ID NO: 42, respectively. $O_{1-6}$CFAST have the amino acid sequences as set forth in SEQ ID NO:35 ($O_1$CFAST), SEQ ID NO: 36 ($O_2$CFAST), SEQ ID NO: 37 ($O_3$CFAST), SEQ ID NO: 38 ($O_4$CFAST), SEQ ID NO: 39 ($O_5$CFAST) and SEQ ID NO: 40 ($O_6$CFAST).

To test the ability of the split-FAST, split-iFAST and split-$O_{1-6}$FAST complementation systems to detect protein-protein interactions in mammalian cells, their N-terminal fragment (i.e., first PYP fragment according to the present invention) was fused to the C-terminus of the FKBP-rapamycin-binding domain of mammalian target of rapamycin (FRB) and their C-terminal fragment (i.e., second PYP fragment according to the present invention) was fused at the C-terminus of the FK506-binding protein (FKBP). FKBP and FRB are known to interact together upon the addition of rapamycin. Addition of rapamycin is thus expected to induce the complementation of the split-FAST, split-iFAST and split-$O_{1-6}$FAST systems.

The following transfection reporters were used to easily detect doubly transfected cells: mTurquoise2 (which provides cyan fluorescence) and iRFP670 (which provides far-red fluorescence). Internal ribosome entry site (IRES)-containing bi-cistronic vectors were generated, allowing the simultaneous expression of FKBP fusions and iRFP670 separately from a single RNA transcript. Internal ribosome entry site (IRES)-containing bi-cistronic vectors were generated, allowing the simultaneous expression of FRB fusions and mTurquoise2 separately from a single RNA transcript.

Human embryonic kidney (HEK) 293T cells were transfected with the two bi-cistronic vectors. The transfected cells were incubated with the fluorogen HMBR at the following concentrations: 0, 1, 5, 10, 25, and 50 μM. Cell fluorescence was analyzed in absence and in presence of 500 nM rapamycin by flow cytometry. The mean fluorescence of doubly transfected cells was extracted for the different conditions.

As shown on FIG. 13, at a given HMBR concentration, with each of the complementation system tested, an increase of the mean cell fluorescence was observed upon addition of rapamycin, in accordance with an interaction-dependent complementation of the PYP fragments. The data thus demonstrate that the split-FAST (FIG. 13A-B), split-iFAST (FIG. 13C) and split-$O_{1-6}$FAST (FIG. 13D-I) complementation systems can be successfully used to detect protein-protein interactions. FIG. 13 also shows that increasing HMBR concentration increased the self-assembly of the PYP fragments (i.e., fluorescence detected in the absence of rapamycin). However, the self-assembly of the PYP fragments remained low and little fluorescence was detected in the absence of rapamycin at lower concentration of HMBR, notably at HMBR concentrations of 25 μM or less, and in particular at HMBR concentrations of 10 μM or less.

---

The invention claimed is:

1. A complementation system comprising a first photoactive yellow protein (PYP) fragment and a second photoactive yellow protein (PYP) fragment, wherein:

the first PYP fragment comprises an amino acid sequence of SEQ ID NO: 23, or an amino acid sequence having at least 70% identity with SEQ ID NO: 23, wherein said first PYP fragment has substitutions Y94W, T95M, F96I, D97P, Y98T, Q99S, M100R, and T101G with reference to SEQ ID NO: 22; and the second PYP fragment comprises an amino acid sequence selected from the group consisting of SEQ ID NO: 34, SEQ ID NO: 35, SEQ ID NO: 36, SEQ ID NO: 37, SEQ ID NO: 38, SEQ ID NO: 39, and SEQ ID NO: 40, or a truncated fragment thereof, wherein said truncated fragment comprises 9 or 10 consecutive amino acids from the N-terminal end of the amino acid sequence of any one of SEQ ID NOs: 34-40;

wherein the first PYP fragment and the second PYP fragment or a functional fragment thereof reconstitute a functional PYP that can bind a fluorogenic hydroxybenzylidene rhodanine (HBR) analog.

2. The complementation system according to claim 1, wherein the first PYP fragment comprises an amino acid sequence selected from the group consisting of SEQ ID NO: 23, SEQ ID NO: 24, SEQ ID NO: 25, SEQ ID NO: 26, SEQ ID NO: 27, SEQ ID NO: 28, and SEQ ID NO: 29.

3. The complementation system according to claim 1, wherein the second PYP fragment comprises the amino acid sequence of SEQ ID NO: 34, or a truncated fragments thereof comprising 9 or 10 consecutive amino acids from the N-terminal end of SEQ ID NO: 34.

4. The complementation system according to claim 1, wherein the first PYP fragment comprises the amino acid sequence of SEQ ID NO: 23, and the second PYP fragment comprises an amino acid sequence selected from the group consisting of SEQ ID NO: 34, SEQ ID NO: 42, and SEQ ID NO: 43.

5. The complementation system according to claim 1, wherein (a) the first PYP fragment further comprises at least one substitutions that corresponds to a substitution in the amino acid sequence of SEQ ID NO: 23 selected from the group consisting of D19N, F62L, P68C, P68E, D71R, P73S, and V107I; and/or (b) the second PYP fragment or the truncated fragment thereof further comprises a substitution that corresponds to the substitution V8I in the amino acid sequence of SEQ ID NO: 34.

6. The complementation system according to claim 1, further comprising a fluorogenic hydroxybenzylidene rhodanine (HBR) analog of formula (I):

formula (I)

wherein
R1, R2, R5 and R6 may be identical or different and each represents H, halo, hydroxyl, aryl, saturated or unsaturated alkyl, saturated or unsaturated cycloalkyl, saturated or unsaturated heteroalkyl, or saturated or unsaturated heterocycloalkyl, wherein the aryl, alkyl, cycloalkyl, heteroalkyl, or heterocycloalkyl is optionally substituted by at least one group selected from halo, hydroxyl, oxo, nitro, amido, carboxy, amino, cyano, haloalkoxy, and haloalkyl;

R3 represents a non-binding doublet, H, halo, hydroxyl, aryl, saturated or unsaturated alkyl, saturated or unsaturated cycloalkyl, saturated or unsaturated heteroalkyl, or saturated or unsaturated heterocycloalkyl, wherein the aryl, alkyl, cycloalkyl, heteroalkyl, or heterocycloalkyl is optionally substituted by at least one group selected from halo, hydroxyl, oxo, nitro, amido, carboxy, amino, cyano, haloalkoxy, and haloalkyl;

R4 is $=$S, $=$O, $=$NH, $=$NR8, $-$SR8, $-$OR8, $-$NHR8, or $-$N(R8)$_2$, wherein R8 is H, hydroxyl, aryl, saturated or unsaturated alkyl, saturated or unsaturated cycloalkyl, saturated or unsaturated heteroalkyl, or saturated or unsaturated heterocycloalkyl, wherein the aryl, alkyl, cycloalkyl, heteroalkyl, or heterocycloalkyl is optionally substituted by at least one group selected from halo, hydroxyl, oxo, nitro, amido, carboxy, amino, cyano, haloalkoxy, and haloalkyl;

X is OH, SH, NHR7, or N(R7)$_2$, wherein R7 is H, halo, hydroxyl, aryl, saturated or unsaturated alkyl, saturated or unsaturated cycloalkyl, saturated or unsaturated heteroalkyl, or saturated or unsaturated heterocycloalkyl, wherein the aryl, alkyl, cycloalkyl, heteroalkyl, or heterocycloalkyl is optionally substituted by at least one group selected from halo, hydroxyl, oxo, nitro, amido, carboxy, amino, cyano, haloalkoxy, and haloalkyl;

Y is O, NH or S.

7. The complementation system according to claim 6, wherein the fluorogenic hydroxybenzylidene rhodanine (HBR) analog is selected from the group consisting of 4-hydroxy-3-methylbenzylidene rhodanine (HMBR), (Z)-2-(5-(4-hydroxy-3-methoxybenzylidene)-4-oxo-2-thioxothi-azolidin-3-yl) acetic acid (HBR-3OM), (Z)-2-(5-(4-hy-droxy-3, 5-dimethylbenzylidene)-4-oxo-2-thioxothiazolidin-3-yl) acetic acid (HBR-3,5DM), and (Z)-

123

2-(5-(4-hydroxy-3, 5-dimethoxybenzylidene)-4-oxo-2-thioxothiazolidin-3-yl) acetic acid (HBR-3,5DOM).

8. A kit comprising at least one vector comprising:
a first nucleic acid sequence encoding a first photoactive yellow protein (PYP) fragment; and
a second nucleic acid sequence encoding a second photoactive yellow protein (PYP) fragment, or a truncated fragment thereof,
wherein the first photoactive yellow protein (PYP) fragment and the second photoactive yellow protein (PYP) fragment, or truncated fragment thereof, are as defined in claim 1.

9. The kit according to claim 8, wherein the kit comprises two vectors with:
the first vector comprising the first nucleic acid sequence encoding the first photoactive yellow protein (PYP) fragment; and
the second vector comprising the second nucleic acid sequence encoding the second photoactive yellow protein (PYP) fragment, or the truncated fragment thereof.

10. The kit according to claim 8, further comprising a fluorogenic hydroxybenzylidene rhodanine (HBR) analog of formula (I):

formula (I)

wherein
R1, R2, R5 and R6 may be identical or different and each represents H, halo, hydroxyl, aryl, saturated or unsaturated alkyl, saturated or unsaturated cycloalkyl, saturated or unsaturated heteroalkyl, or saturated or unsaturated heterocycloalkyl, wherein the aryl, alkyl, cycloalkyl, heteroalkyl, or heterocycloalkyl is optionally substituted by at least one group selected from halo, hydroxyl, oxo, nitro, amido, carboxy, amino, cyano, haloalkoxy, and haloalkyl;
R3 represents a non-binding doublet, H, halo, hydroxyl, aryl, saturated or unsaturated alkyl, saturated or unsaturated cycloalkyl, saturated or unsaturated heteroalkyl, or saturated or unsaturated heterocycloalkyl, wherein the aryl, alkyl, cycloalkyl, heteroalkyl, or heterocycloalkyl is optionally substituted by at least one group selected from halo, hydroxyl, oxo, nitro, amido, carboxy, amino, cyano, haloalkoxy, and haloalkyl;
R4 is =S, =O, =NH, =NR8, —SR8, —OR8, —NHR8, or —N(R8)$_2$, wherein R8 is H, hydroxyl, aryl, saturated or unsaturated alkyl, saturated or unsaturated cycloalkyl, saturated or unsaturated heteroalkyl, or saturated or unsaturated heterocycloalkyl, wherein the aryl, alkyl, cycloalkyl, heteroalkyl, or heterocycloalkyl is optionally substituted by at least one group selected from halo, hydroxyl, oxo, nitro, amido, carboxy, amino, cyano, haloalkoxy, and haloalkyl;
X is OH, SH, NHR7, or N(R7)$_2$, wherein R7 is H, halo, hydroxyl, aryl, saturated or unsaturated alkyl, saturated or unsaturated cycloalkyl, saturated or unsaturated heteroalkyl, or saturated or unsaturated heterocycloalkyl, wherein the aryl, alkyl, cycloalkyl, heteroalkyl, or heterocycloalkyl is optionally substituted by at least one group selected from halo, hydroxyl, oxo, nitro, amido, carboxy, amino, cyano, haloalkoxy, and haloalkyl;
Y is O, NH or S.

11. The kit according to claim 10, wherein the fluorogenic hydroxybenzylidene rhodanine (HBR) analog is selected from the group consisting of 4-hydroxy-3-methylbenzylidene rhodanine (HMBR), (Z)-2-(5-(4-hydroxy-3-methoxybenzylidene)-4-oxo-2-thioxothiazolidin-3-yl) acetic acid (HBR-3OM), (Z)-2-(5-(4-hydroxy-3, 5-dimethylbenzylidene)-4-oxo-2-thioxothiazolidin-3-yl) acetic acid (HBR-3,5DM), and (Z)-2-(5-(4-hydroxy-3, 5-dimethoxybenzylidene)-4-oxo-2-thioxothiazolidin-3-yl) acetic acid (HBR-3,5DOM).

12. A method for detecting an interaction between two biological molecules of interest in a sample, comprising the steps of:
fusing a first photoactive yellow protein (PYP) fragment to a first biological molecule of interest, thereby tagging the first biological molecule of interest with said first PYP fragment;
fusing a second photoactive yellow protein (PYP) fragment, or a truncated fragment thereof, to a second biological molecule of interest, thereby tagging the second biological molecule of interest with said second PYP fragment, or truncated fragment thereof;
contacting the sample with a fluorogenic hydroxybenzylidene rhodanine (HBR) analog; and
detecting a fluorescence resulting from the binding of the fluorogenic HBR analog to a functional PYP, or a functional truncated fragment thereof, reconstituted upon interaction of the two biological molecules of interest;
thereby detecting the interaction of the two biological molecules of interest present in the sample through the binding of the fluorogenic HBR analog to the functional PYP, or the functional truncated fragment thereof, reconstituted upon interaction of the two biological molecules of interest, and
wherein the first photoactive yellow protein (PYP) fragment and the second photoactive yellow protein (PYP) fragment, or truncated fragment thereof, are as defined in claim 1.

13. The method according to claim 12, wherein the two biological molecules of interest are two proteins of interest.

14. The method according to claim 12, for monitoring over time and/or space the association and dissociation of the two biological molecules of interest, through the detection of the interaction between said biological molecules of interest.

15. The method according to claim 14, wherein the two biological molecules of interest are two proteins of interest.

16. A screening method for identifying a new protein-protein interaction between two protein candidates of interest in a sample, comprising the steps of:
fusing a first photoactive yellow protein (PYP) fragment to a first protein candidate of interest, thereby tagging the first protein candidate of interest with said first PYP fragment;
fusing a second photoactive yellow protein (PYP) fragment, or a truncated fragment thereof, to a second protein candidate of interest, thereby tagging the second protein candidate of interest with said second PYP fragment, or truncated fragment thereof;

contacting the sample with a fluorogenic hydroxyben-zylidene rhodanine (HBR) analog; and detecting a fluorescence resulting from the binding of the fluorogenic HBR analog to a functional PYP, or a functional truncated fragment thereof, reconstituted upon interaction of the two protein candidates of interest;

thereby identifying a new protein-protein interaction between the two protein candidates of interest present in the sample, through the binding of the fluorogenic HBR analog to the functional PYP, or the functional truncated fragment thereof, reconstituted upon interaction of the two protein candidates of interest, and wherein the first photoactive yellow protein (PYP) fragment and the second photoactive yellow protein (PYP) fragment, or truncated fragment thereof, are as defined in claim 1.

17. An assay relying on the detection of an interaction between two proteins in a sample, said assay comprising the steps of:

obtaining a first tagged protein, wherein the protein is tagged with a first photoactive yellow protein (PYP) fragment;

obtaining a second tagged protein, wherein the protein is tagged with a second photoactive yellow protein (PYP) fragment, or a truncated fragment thereof;

contacting the sample with a fluorogenic hydroxyben-zylidene rhodanine (HBR) analog; and detecting a fluorescence resulting from the binding of the fluorogenic HBR analog to a functional PYP, or a functional truncated fragment thereof, reconstituted upon interaction of the two proteins;

thereby detecting the interaction of the two proteins present in the sample, through the binding of the fluorogenic HBR analog to the functional PYP, or the functional truncated fragment thereof, reconstituted upon interaction of the two proteins, and wherein the first photoactive yellow protein (PYP) fragment, and the second photoactive yellow protein (PYP) fragment, or truncated fragment thereof, are as defined in claim 1.

18. The assay according to claim 17, wherein said assay is for assessing the capacity of a molecule of interest to stabilize or to inhibit protein-protein interactions.

19. The assay according to claim 17, wherein said assay is for assessing a signaling pathway of interest, with the interaction of the two proteins depending on the activation of the signaling pathway of interest; or is for assessing the capacity of a molecule of interest to modulate said signaling pathway of interest.

* * * * *